(12) United States Patent
Bystrom et al.

US009233946B2

(10) Patent No.: US 9,233,946 B2
(45) Date of Patent: Jan. 12, 2016

(54) SULFONAMIDE COMPOUNDS

(75) Inventors: Styrbjorn Bystrom, Taby (SE); Charles Hedgecock, Uppsala (SE); Evert Homan, Sollentuna (SE); Thomas Lundback, Trangsund (SE); Jessica Martinsson, Sollentuna (SE); Meral Sari, Jarfalla (SE); Katarina Farnegardh, Ekero (SE); Mattias Jonsson, Knivsta (SE)

(73) Assignee: KANCERA AB, Solna (SE)

( * ) Notice: Subject to any disclaimer, the term of this patent is extended or adjusted under 35 U.S.C. 154(b) by 127 days.

(21) Appl. No.: 13/823,810

(22) PCT Filed: Sep. 19, 2011

(86) PCT No.: PCT/EP2011/066250
§ 371 (c)(1),
(2), (4) Date: Mar. 15, 2013

(87) PCT Pub. No.: WO2012/035171
PCT Pub. Date: Mar. 22, 2012

(65) Prior Publication Data
US 2013/0172339 A1 Jul. 4, 2013

Related U.S. Application Data

(60) Provisional application No. 61/383,952, filed on Sep. 17, 2010.

(30) Foreign Application Priority Data
Sep. 17, 2010 (EP) .................. 10177376.0

(51) Int. Cl.
| C07D 417/12 | (2006.01) |
| C07D 409/12 | (2006.01) |
| C07D 333/04 | (2006.01) |
| C07D 333/62 | (2006.01) |
| C07C 311/21 | (2006.01) |
| C07C 311/29 | (2006.01) |
| C07D 257/04 | (2006.01) |
| C07D 307/82 | (2006.01) |
| C07D 333/34 | (2006.01) |
| C07D 405/12 | (2006.01) |
| C07D 409/04 | (2006.01) |
| C07D 409/14 | (2006.01) |
| C07D 413/04 | (2006.01) |
| C07D 413/12 | (2006.01) |
| C07D 413/14 | (2006.01) |
| C07D 417/04 | (2006.01) |
| C07D 417/14 | (2006.01) |
| C07D 409/10 | (2006.01) |
| C07D 413/10 | (2006.01) |

(52) U.S. Cl.
CPC ............ *C07D 333/62* (2013.01); *C07C 311/21* (2013.01); *C07C 311/29* (2013.01); *C07D 257/04* (2013.01); *C07D 307/82* (2013.01); *C07D 333/04* (2013.01); *C07D 333/34* (2013.01); *C07D 405/12* (2013.01); *C07D 409/04* (2013.01); *C07D 409/10* (2013.01); *C07D 409/12* (2013.01); *C07D 409/14* (2013.01); *C07D 413/04* (2013.01); *C07D 413/10* (2013.01); *C07D 413/12* (2013.01); *C07D 413/14* (2013.01); *C07D 417/04* (2013.01); *C07D 417/12* (2013.01); *C07D 417/14* (2013.01)

(58) Field of Classification Search
CPC ... C07D 333/04; C07D 409/12; C07D 417/12
See application file for complete search history.

(56) References Cited

U.S. PATENT DOCUMENTS

| 2004/0167128 A1 | 8/2004 | Comess et al. |
| 2010/0267815 A1 | 10/2010 | Telang et al. |

FOREIGN PATENT DOCUMENTS

| DE | 278 091 C | 9/1914 |
| GB | 458 417 A | 12/1936 |
| WO | 2005/060963 A1 | 7/2005 |
| WO | 2006/051270 A1 | 5/2006 |
| WO | 2007/054623 A2 | 5/2007 |
| WO | 2007/076055 A2 | 7/2007 |
| WO | 2010/075869 A1 | 7/2007 |
| WO | 2008/074132 A1 | 6/2008 |
| WO | 2008/114022 A1 | 9/2008 |
| WO | 2008/156783 A2 | 12/2008 |
| WO | 2010/076034 A1 | 7/2010 |
| WO | 2011103557 A1 | 8/2011 |

OTHER PUBLICATIONS

Ando et al., "Interleukin 6 Enhances Glycolysis through Expression of the Glycolytic Enzymes Hexokinase 2 and 6-Phosphofructo-2-kinase/Fructose-2,6-bisphosphatase-3", J. Nippon Med. Sch, 2010, vol. 77, No. 2, pp. 97-105.

Bache et al., "Detection and Specific Targeting of Hypoxic Regions within Solid Tumors: Current Preclinical and Clinical Strategies", Current Medicinal Chemistry, 2008, vol. 15, pp. 322-338.

Bobarykina et al., "Hypoxic regulation of PFKFB-3 and PFKFB-4 gene expression in gastric and pancreatic cancer cell lines and expression of PFKFB genes in gastric cancers", Acta Biochimica Polonica, 2006, vol. 53, No. 4, pp. 789-799.

Brown, J. Martin, "The Hypoxic Cell: A Target for Selective Cancer Therapy—Eighteenth Bruce F. Cain Memorial Award Lecture", Cancer Research, Special Lecture, 1999, vol. 59, pp. 5863-5870.

(Continued)

*Primary Examiner* — Samira Jean-Louis
(74) *Attorney, Agent, or Firm* — Young & Thompson

(57) ABSTRACT

A compound of formula (I), wherein A is S, O or a double bond, and L is a substituted thiazolyl, phenyl or pyridyl. The compound is useful for the treatment of inflammation and cancer.

16 Claims, 1 Drawing Sheet

(56) References Cited

OTHER PUBLICATIONS

Bruni et al., "An Endpoint Enzymatic Assay for Fructose 2,6-Bisphosphate Performed in 96-Well Plates", Analytical Biochemistry, 1989, vol. 178, pp. 324-326.
Chesney et al., "An inducible gene product for 6-phosphofructo-2-kinase with an AU-rich instability element: Role in tumor cell glycolysis and the Warburg effect", Proc. Natl. Acad. Sci. USA, 1999, vol. 96, pp. 3047-3052.
Clem et al., "Small-molecule inhibition of 6-phosphofructo-2-kinase activity suppresses glycolytic flux and tumor growth", Mol. Cancer Ther., 2008, vol. 7, No. 1, pp. 110-120.
Del Rey et al., "The transcriptional Response of Normal and Rheumatoid Arthritis Synovial Fibroblasts to Hypoxia", Arthritis & Rheumatism, 2010, vol. 62, No. 12, pp. 3584-3594.
Graham et al., "Topically Active Carbonic Anhydrase Inhibitors. 3. Benzofuran- and Indole-2-sulfonamides", J. Med. Chem., 1990, vol. 33, pp. 749-754.
Hirata et al., "Inhibition of Tumor Cell Growth by a Specific 6-Phosphofructo-2-kinase Inhibitor, N-Bromoacetylethanolamine Phosphate, and Its Analogues", Biosci. Biotechnol. Biochem., 2000, vol. 64, No. 10, pp. 2047-2052.
Huang et al., "New Ammonia Equivalents for the Pd-Catalyzed Amination of Aryl Halides", Organic Letters, 2001, vol. 3, No. 21, pp. 3417-3419.
Jiang et al., "Environmentally friendly synthesis of biaryls: Suzuki reaction of aryl bromides in water at low catalyst loadings", Tetrahedron Letters, 2006, vol. 47, pp. 197-200.
Kim et al., "A Direct Substrate-Substrate Interaction Found in the Kinase Domain of the Difunctional Enzyme, 6-Phosphofructo-2-kinase/Fructose-2,6-bisphosphatase", J. Mol. Biol., 2007, vol. 370, pp. 14-26.
Kothari et al., "Synthesis of some Newer 5-(5-Aryl-2H-tetrazol-2-ylmethyl)-4-substituted-s-triazole-3-thiols as Possible Antiinflammatory Agents", J. Heterocyclic Chem., 1980, vol. 17, pp. 1393-1398.
Liu et al., "Hypoxia increases tumor cell sensitivity to glycolytic Inhibitors: a strategy for solid tumor therapy (Model C)", Biochemical Pharmacology, 2002, vol. 64, pp. 1745-1751.
Liu et al., "Hypersensitization of Tumor Cells to Glycolytic Inhibitors", Biochemistry, 2001, vol. 40, pp. 5542-5547.
Minchenko et al., "Overexpression of 6-phosphofructo-2-kinase/fructose-2,6-bisphosphatase-4 in the human breast and colon malignant tumors", Biochimie, 2005, vol. 87, pp. 1005-1010.
Michenko et al., "Hypoxia induces transcription of 6-phosphofructo-2-kinase/fructose-2,6-biphosphatase-4 gene via hypoxia-inducible factor-1 α activation", FEBS Letters, 2004, vol. 576, pp. 14-20.
Okar et al., "PFK-2/FBPase-2:maker and breaker of the essential biofactor fructose-2, 6-bisphosphate", Trends in Biochemical Sciences, 2001, vol. 26, No. 1, pp. 30-35.
Pan et al., "Metabolic Targeting as an Anticancer Strategy: Dawn of a New Era?", Science STKE, 2007, vol. 381, pp. 1-4.
Pilkis et al., "6-Phosphofructo-2-Kinase/Fructose-2,6-Bisphosphatase: A Metabolic Signaling Enzyme", Annu. Rev. Biochem., 1995, vol. 64, pp. 799-835.
Ple et al., "Synthesis of Substituted Benzo[b]thiophenes by Acid-Catalyzed Cyclization of Thiophenylacetals and Ketones", J. Heterocyclic. Chem., 1988, vol. 25, pp. 1271-1272.
Ramanathan et al., "Perturbational profiling of a cell-line model of tumorigenesis by using metabolic measurements", PNAS, 2005, vol. 102, No. 17, pp. 5992-5997.
Rider et al., "6-Phosphofructo-2-kinase/fructose-2,6-bisphosphatase: head-to-head with a bifunctional enzyme that controls glycolysis", Biochem. J., 2004, vol. 381, pp. 561-579.
Sakakibara et al., "Hexose Phosphate Binding Sites of Fructose-6-phosphate, 2-kinase_Fructose-2, 6-bisphosphatase", The Journal of Biological Chemistry, 1984, vol. 259, No. 22, pp. 14023-14028.
Telang et al., "Ras transformation requires metabolic control by 6-phosphofructo-2-kinase", Oncogene, 2006, vol. 25, pp. 7225-7234.
Schaftingen et al., "A Kinetic Study of Pyrophosphate: Fructose-6-Phosphate Phosphotransferase from Potato Tubers", Eur. J. Biochem. 1982, vol. 129, pp. 191-195.
Heiden et al., "Understanding the Warburg Effect: The Metabolic Requirements of Cell Proliferation", Science, 2009, vol. 324, pp. 1029-1033.
Walenta et al., "Lactate: Mirror and Motor of Tumor Malignancy", Seminars in Radiation Oncology, 2004, vol. 14, No. 3, pp. 267-274.
Walenta et al., "Lactate in Solid Malignant Tumors: Potential Basis of a Metabolic Classification in Clinical Oncology", Current Medicinal Chemistry, 2004, vol. 11, pp. 2195-2204.
Warburg, Otto, "On the Origin of Cancer Cells", Science, 1956, vol. 123, No. 3191, pp. 309-314.
Xie et al., "Synthesis of benzofurans in ionic liquid by a PdCl2-catalyzed intramolecular Heck reaction", Tetrahedron Letters, 2004, vol. 45, pp. 6235-6237.
Xu et al., "Inhibition of Glycolysis in Cancer Cells: A Novel Strategy to Overcome Drug Resistance Associated with Mitochondrial Respiratory Defect and Hypoxia", Cancer Res., 2005, vol. 65, No. 2, pp. 613-621.
Desai et al.: "Studies in Sulphonamides: Part IV. Some N-Heterocyclic Sulphonamides from 2-Naphthylamine as possible Antibacterial Agents", Journal of the Indian Chemical Society, vol. 46., No. 5., 1969, pp. 411-414, XP002969906.
Roffey J: "Maybridge MedChem Bioisosteres in Medicinal Chemistry", vol. 1, Internet Citation, 2004, XP002448278, Retrieved from the Internet: URL:http://www.maybridge.com/Images/pdfs/medchem_vol1.pdf [retrieved on Aug. 27, 2007] pp. 6-9.
Database Registry [Online] Chemical Abstracts Service, Columbus, Ohio; Jan. 19, 2006, XP002674783, retrieved from STN Database accession No. 872192-82-0 (RN).
Database Registry [Online] Chemical Abstracts Service, Columbus, Ohio; Nov. 7, 2008, XP002674784, retrieved from STN Database accession No. 1071304-17-0 (RN).
Database Registry [Online] Chemical Abstracts Service, Columbus, Ohio; Apr. 13, 2011, XP002674785, retrieved from STN Database accession No. 1278711-64-0 (RN).
Database Registry [Online] Chemical Abstracts Service, Columbus, Ohio; May 1, 2011, XP002674786, retrieved from STN Database accession No. 1288407-56-6 (RN).
Database Registry [Online] Chemical Abstracts Service, Columbus, Ohio; Aug. 15, 2011, XP002674787, retrieved from STN Database accession No. 1318121-74-2 (RN).
International Search Report, dated May 9, 2012, from corresponding PCT application.

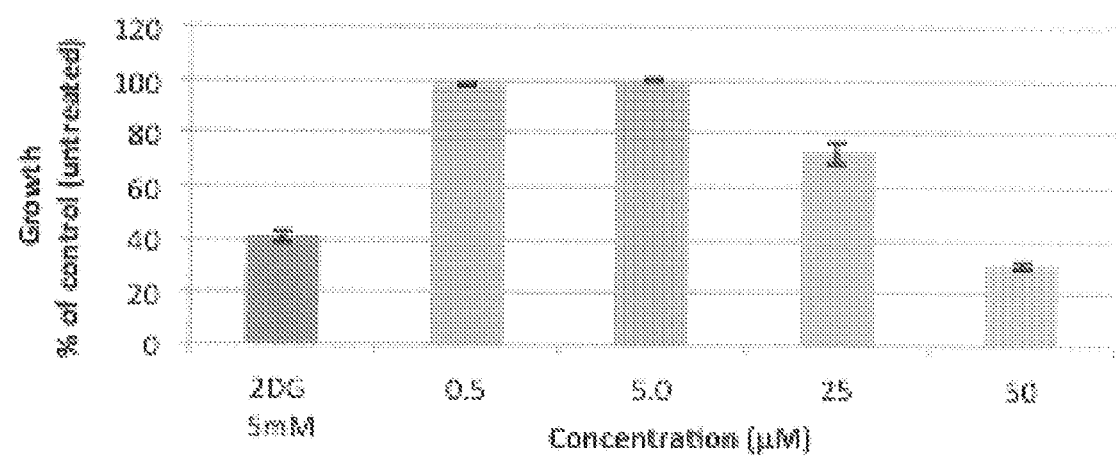

SULFONAMIDE COMPOUNDS

TECHNICAL FIELD

This invention relates to new sulfonamide derivatives, to pharmaceutical compositions comprising these compounds, to processes for their preparation, as well as their use for the preparation of a medicament for use in therapy, e.g. for the treatment of cancer and inflammation, as well as methods of treatment of these disorders.

BACKGROUND OF THE INVENTION

In the 1920s Otto Warburg first proposed non-oxidative metabolism of glucose as a unique feature of tumors (Warburg, (1930) Ueber den stoffwechsel der tumoren (London: Constable); Warburg, (1956) Science 123, 309-314). This hypothesis has since caused significant interest and although mechanistic links are still, almost 100 years later, under investigation, a high glucose flux of tumor is today exploited clinically, using PET imaging of $^{18}$F-2-deoxyglucose uptake as a diagnostic tool for solid tumors.

Lately abnormal energy processing of cancer cells has been given new attention (Vander Heiden, et al. (2009) Science 324, 1029). The hypoxic microenvironment and consequential lactate accumulation resulting from altered tumor metabolism are predictive for both metastatic potential and therapy resistance, and thus survival of cancer patients (Brown, (1999) Cancer Res. 59, 5863-5870; Walenta & Mueller-Klieser, (2004) Semin. Radiat. Oncol. 14, 267-274; Walenta et al., (2004) Curr. Med. Chem. 11, 2195-2204). Targeting of these hypoxic and acidotic tumor areas, has therefore drawn attention as a complement to anti-proliferative treatments (see e.g. Pan & Mak, (2007) Sci. STKE 381, pe14; Bache et al., (2008) Curr. Med. Chem. 15, 322-338 for reviews).

Known inhibitors of glycolysis are 2-deoxyglucose and 2-bromo-pyruvate targeting hexokinase (Liu et al., (2001) Biochemistry 40, 5542-5547; Liu et al. (2002) Biochem. Pharmacol. 64, 1745-1751; Xu et al., (2005) Cancer Res. 65, 613-621; Ramanathan et al., (2005) Proc. Natl. Acad. Sci. USA 102, 5992-5997). Fructose-2,6-bisphosphate (F-2,6-P$_2$) plays a regulatory role in glucose metabolism by relieving ATP inhibition of phosphofructokinase-1. The levels of F-2, 6-P$_2$ are regulated by the bifunctional enzyme family 6-phosphofructo-2-kinase/fructose-2,6-bisphosphatase (PFKFB1-4).

Of these four isozymes, mainly PFKFB3 and PFKFB4 are of particular interest for playing a role in cancer. Anti-sense treatment against PFKFB3 was shown to reduce tumor growth rate in vivo (Chesney et al., (1999) Proc. Natl. Acad. Sci. USA 96, 3047-3052) Also, a decreased anchorage independent growth was shown for siRNA treated fibroblasts (Telang et al., (2006) Oncogene 25, 7225-7234). It has recently been demonstrated that the proinflammatory cytokine interleukin (IL)-6 enhances glycolysis in mouse embryonic fibroblasts and human cell lines (Ando et al. J Nippon Med Sch (2010), 77, (2), 97-105) indicating the potential for PFKFB3 inhibitors as anti-inflammatory agents. Hypoxia is a prominent feature in rheumatoid arthritis (RA) synovium, and induce significant changes in the expression of PFKFB3 and PFKFB 4 (Del Rey et al., (2010) Arthritis & Rheumatism 62, 3584-3594).

Minchenko et al. showed increased expression of PFKFB4 mRNA in breast and colon malignant tumors as compared to corresponding non-malignant tissue counterparts as well as in several cancer cell lines. PFKFB4 was reported to be strongly responsive to hypoxia (Minchenko et al., (2004) FEBS Lett. 576, 14-20); Minchenko et al., (2005), Biochemie 87, 1005-1010; Bobarykina et al., (2006), Acta Biochemica Polonica 3, 789-799). Recently, Telang et al. showed decreased levels of F-2,6-P$_2$ and lactate as well as decreased tumor growth following siRNA silencing of PFKFB4 (Telang, S. et al, (2010) US2010/0267815 A1).

Only a small number of specific inhibitors of the kinase activities of PFKFB3 and PFKFB4 have been identified. In one study, an alkylating inhibitor, N-bromoacetylethanolamine phosphate, was used as a tool to investigate the binding sites of the kinase and phosphatase domains of PFKFB3 and was demonstrated to irreversibly inactivate PFK-2 (Sakakibara et al. (1984), J. Biol. Chem 259, 14023-14028). The compound is a competitive inhibitor of PFK-2 with respect to F6P but a noncompetitive inhibitor with respect to ATP. Analogues of this compound, N-(2-methoxyethyl)-bromoacetamide, N-(2-ethoxyethyl)-bromoacetamide and N-(3-methoxypropyl)-bromoacetamide, have demonstrated in vivo activity with increased survival rate of P388 transplant BDF$_1$ mice (Hirata et al. (2000) Biosci. Biotechnol. Biochem. 64, 2047-2052).

A crystal structure of the PFKFB3*ADP*phosphoenolpyruvate complex was described by Kim et al. (Kim et al. (2007), J. Mol. Biol. 370, 14-26). This paper also described the crystal structures of PFKFB3*AMPPCP*fructose-6 phosphate complex where β,γ-methylene-adenosine 5'-triphosphate (AMPPCP) constituted a non-hydrolysable ATP-analogue.

A drug-like compound was described (Clem et al. (2008) Mol. Cancer Ther. 7, 110-120; Chesney et al. (2008) WO 2008/156783) where 3-(3-pyridinyl)-1-(4-pyridinyl)-2-propen-1-one (3PO), by computational methods, was identified as a PFKFB3 inhibitor. Administration of 3PO reduced the intracellular concentration of F-2,6-P$_2$, glucose uptake, and growth of established tumors in vivo. Recently, substituted benzindoles were described as inhibitors of PFKFB3. The benzindoles were shown to inhibit proliferation in several cancer cell lines, inhibit glucose uptake as well as to reduce tumor growth in vivo in tumor models (Chand et al. (2011) WO2011/103557A1).

SUMMARY OF THE INVENTION

One object of the present invention is to provide small molecule inhibitors of the kinase activities of PFKFB3 and/or PFKFB4.

Another object of the present invention is to provide compounds for use in the treatment of inflammation or cancer.

According to a first aspect the present invention provides a compound of formula (I)

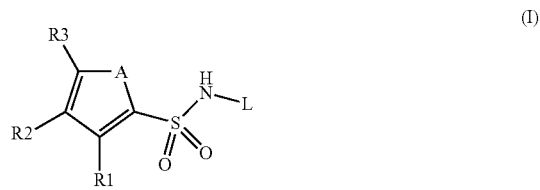

wherein:
(i) A is O or S; and
R$^1$ is selected from H; halogen; and C1-C6 alkyl optionally substituted with at least one halogen; or R¹ and R² form, together with the carbon atoms to which they are attached, a benzene ring optionally substituted with at least one R⁶; or a 5- or 6-membered heteroaromatic or heterocyclic ring, optionally substituted with at least one R⁶;

R² and R³ are independently selected from H; halogen; C1-C6 alkyl optionally substituted with at least one halogen; phenyl optionally substituted with at least one R⁶; 5- or 6-membered heteroaryl optionally substituted with at least one R⁶; and 5- or 6-membered arylsulfonyl or heteroarylsulfonyl, optionally substituted with at least one R⁶; provided that at least one of R² and R³ is selected from said phenyl, heteroaryl, arylsulfonyl and heteroarylsulfonyl, and when L is (a), neither R² nor R³ is unsubstituted phenyl; or R² and R³ form, together with the carbon atoms to which they are attached, a benzene ring optionally substituted with at least one R⁶; or a 5- or 6-membered heteroaromatic or heterocyclic ring, optionally substituted with at least one R⁶; or (ii) A is CR'=CR';
each R' is independently selected from H; halogen; and C1-C6 alkyl optionally substituted with at least one halogen;
R¹ is selected from H; halogen; and C1-C6 alkyl optionally substituted with at least one halogen; or
R¹ and R² form, together with the carbon atoms to which they are attached, a benzene ring optionally substituted with at least one R⁶; or a 5- or 6-membered heteroaromatic or heterocyclic ring, optionally substituted with at least one R⁶;
R² and R³ are independently selected from H, halogen, C1-C6 alkyl optionally substituted with at least one halogen; phenyl optionally substituted with at least one R⁶; 5- or 6-membered heteroaryl optionally substituted with at least one R⁶; and 5- or 6-membered arylsulfonyl or heteroarylsulfonyl, optionally substituted with at least one R⁶; provided that:

when both R² and R³ are selected from H, halogen and C1-C6 alkyl optionally substituted with at least one halogen, the ring containing A is substituted in ortho position relative to the sulphonamide bond with at least one substituent selected from halogen and C1-C6 alkyl optionally substituted with at least one halogen;
when L is (a), neither R² nor R³ is unsubstituted phenyl; and
when L is (c), R³ is optionally substituted phenyl only when R⁵ is tetrazol-5-yl, and R² is unsubstituted phenyl only when R⁴ is not hydroxy; or R² and R³ form, together with the carbon atoms to which they are attached, a benzene ring optionally substituted with at least one R⁶, provided that said benzene ring is unsubstituted only when R⁵ is tetrazolyl or oxazolyl; or a 5- or 6-membered heteroaromatic or heterocyclic ring, optionally substituted with at least one R⁶;
L is (a)
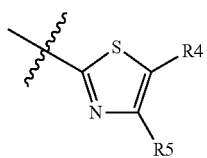

wherein
R⁴ is COOR¹²; and R⁵ is selected from H and C1-C6 alkyl; or
R⁴ is selected from H and C1-C6 alkyl; and R⁵ is COOR¹²; or (b)
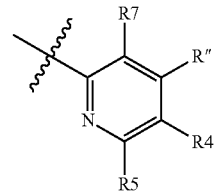

wherein
R⁴ is selected from H and C1-C6 alkyl;
R⁵ is selected from H and C1-C6 alkyl; and R" is selected from C0-C1 alkyl-COOR¹²; or
R⁵ is selected from COOR¹²; and R" is selected from H and C1-C6 alkyl; and
R⁷ is selected from H, C1-C6 alkyl, and nitro; or (c)
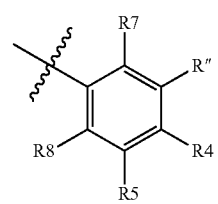

wherein
R⁴ is selected from H, hydroxy and C1-C6 alkyl;
R⁵ is selected from H, C1-C6 alkyl; and R" is selected from C0-C1 alkyl-COOR¹²; or
R⁵ is selected from COOR¹², oxazol-5-yl and tetrazol-5-yl, said oxazol-5-yl and tetrazol-5-yl optionally being substituted by R⁹; and R" is selected from H, C1-C6 alkyl, and nitro;
R⁷ is selected from H, C1-C6 alkyl, and nitro; and
R⁸ is selected from H, hydroxy, and C1-C6 alkyl; or (d)
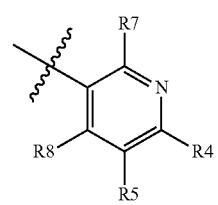

wherein
R⁴ is selected from H and C1-C6 alkyl; and
R⁵ is COOR¹²;
R⁷ is selected from H, C1-C6 alkyl, and nitro; and
R⁸ is selected from H, hydroxy, and C1-C6 alkyl;
provided that in any of (a), (b), (c) and (d), R⁴, R⁵ and R" are selected from C0-C1 alkyl-COOR¹² only when at least one of R² or R³ is optionally substituted phenyl or optionally substituted heteroaryl; or when R² and R³ together with the carbon atoms to which they are attached form a benzene ring optionally substituted by at least one R⁶;
R⁶ is selected from C1-C6 alkyl, cyano, halogen, hydroxy, C1-C6 alkoxy, C1-C6 alkylthio, tetrahydropyrrolyl, R¹⁰R¹¹N, carbamoyl, and C1-C6 alkylcarbonylamino, or is an ethyleneoxy biradical forming, together with the atoms to which it is attached, a five-membered oxygen containing cycle; wherein any alkyl is optionally substituted with at least one halogen;

$R^9$ is selected from C0-C1 alkyl-COOR¹²;

$R^{10}$ and $R^{11}$ are independently selected from H and C1-C6 alkyl or form, together with the nitrogen to which they are attached, a 5- or 6-membered cyclic amino optionally containing one other cyclic heteroatom;

$R^{12}$ is selected from H, C1-C6 alkyl; heteroaryl-C0-C2 alkyl; (C1-C3 alkoxy)$_p$C1-C3 alkyl; aryl-C0-C2 alkyl; heterocyclyl-C0-C2 alkyl; and C1-C6 dialkylamino-C1-C6 alkyl, wherein any cyclic moiety is optionally substituted with C1-C6 alkyl;

p is 1 or 2;

or a pharmaceutically acceptable salt thereof;

provided that the compound is not:

ethyl 2-(benzofuran-2-sulfonamido)thiazole-4-carboxylate;
ethyl 2-(5-methylbenzo[b]thiophene-2-sulfonamido)thiazole-4-carboxylate;
ethyl 2-(benzo[b]thiophene-2-sulfonamido)thiazole-4-carboxylate;
ethyl 2-(6-acetamidonaphthalene-2-sulfonamido)-4-methylthiazole-5-carboxylate;
ethyl 2-(6-aminonaphthalene-2-sulfonamido)-4-methylthiazole-5-carboxylate;
methyl 6-(4'-cyano-[1,1'-biphenyl]-4-ylsulfonamido)picolinate;
2-(3-(benzo[b]thiophene-2-sulfonamido)phenyl)acetic acid;
methyl 2-(3-(benzo[b]thiophene-2-sulfonamido)phenyl)acetate;
ethyl 3-(5-(6-oxo-1,6-dihydropyridazin-3-yl)furan-2-sulfonamido)benzoate;
ethyl 3-(5-(5-(trifluoromethyl)isoxazol-3-yl)furan-2-sulfonamido)benzoate;
ethyl 3-(5-(4,5-dimethyl-1H-pyrazol-3-yl)thiophene-2-sulfonamido)benzoate;
ethyl 3-(5-(5-methyl-1H-pyrazol-3-yl)thiophene-2-sulfonamido)benzoate;
ethyl 3-(5-(5-(trifluoromethyl)isoxazol-3-yl)thiophene-2-sulfonamido)benzoate;
ethyl 3-(5-(3-(trifluoromethyl)isoxazol-5-yl)thiophene-2-sulfonamido)benzoate;
ethyl 3-(5-(3-methylisoxazol-5-yl)thiophene-2-sulfonamido)benzoate;
ethyl 3-(4-(4-(tert-butyl)thiazol-2-yl)thiophene-2-sulfonamido)benzoate;
methyl 3-(4-(4-(tert-butyl)thiazol-2-yl)thiophene-2-sulfonamido)benzoate;
methyl 3-(3-(1H-tetrazol-1-yl)phenylsulfonamido)benzoate;
ethyl 3-(2-ethyl-5-(5-(trifluoromethyl)isoxazol-3-yl)phenylsulfonamido)benzoate;
ethyl 3-(2-methyl-5-(5-methyl-1,2,4-oxadiazol-3-yl)phenylsulfonamido)benzoate;
ethyl 3-(3-(5-methyl-1,2,4-oxadiazol-3-yl)phenylsulfonamido)benzoate;
ethyl 3-(2-methyl-5-(5-methyl-1H-pyrazol-3-yl)phenylsulfonamido)benzoate;
ethyl 3-(2-methyl-5-(2-methylthiazol-4-yl)phenylsulfonamido)benzoate;
ethyl 3-(2-isopropyl-5-(3-methylisoxazol-5-yl)phenylsulfonamido)benzoate;
ethyl 3-(2-methyl-5-(2-methyloxazol-5-yl)phenylsulfonamido)benzoate;
ethyl 3-(2-ethyl-5-(3-methylisoxazol-5-yl)phenylsulfonamido)benzoate;
ethyl 3-(4-(2-methyloxazol-4-yl)phenylsulfonamido)benzoate;
ethyl 3-(4-(2-methyloxazol-5-yl)phenylsulfonamido)benzoate;
methyl 3-(4-(2,5-dimethyloxazol-4-yl)phenylsulfonamido)benzoate;
ethyl 3-(2-methyl-5-(6-oxo-1,6-dihydropyridazin-3-yl)phenylsulfonamido)benzoate;
3-(6-butoxynaphthalene-2-sulfonamido)benzoic acid;
3-(6-methoxynaphthalene-2-sulfonamido)benzoic acid;
3-(6-propoxynaphthalene-2-sulfonamido)benzoic acid;
3-(6-methylnaphthalene-2-sulfonamido)benzoic acid;
3-(4-(3,5-dimethyl-1H-pyrazol-1-yl)phenyl sulfonamido) benzoic acid;
N-(3-(2H-tetrazol-5-yl)phenyl)benzo[c][1,2,5]thiadiazole-4-sulfonamide;
N-(3-(2H-tetrazol-5-yl)phenyl)-2,3,5,6-tetramethylbenzenesulfonamide;
N-(3-(2H-tetrazol-5-yl)phenyl)-2,4,5-trichlorobenzenesulfonamide;
N-(3-(2H-tetrazol-5-yl)phenyl)-5-(tert-butyl)-2-methylbenzenesulfonamide;
3-methyl-N-(3-(oxazol-5-yl)phenyl)quinoline-8-sulfonamide;
5-bromo-2-methyl-N-(3-(oxazol-5-yl)phenyl)benzenesulfonamide;
2,5-dichloro-3,6-dimethyl-N-(3-(oxazol-5-yl)phenyl)benzenesulfonamide;
N-(3-(oxazol-5-yl)phenyl)-2,3-dihydrobenzofuran-5-sulfonamide;
2-chloro-4-methyl-N-(3-(oxazol-5-yl)phenyl)benzenesulfonamide;
2-chloro-4-fluoro-N-(3-(oxazol-5-yl)phenyl)benzenesulfonamide;
2-fluoro-N-(3-(oxazol-5-yl)phenyl)benzenesulfonamide;
N-(3-(oxazol-5-yl)phenyl)quinoline-8-sulfonamide;
N-(3-(oxazol-5-yl)phenyl)naphthalene-2-sulfonamide;
2-bromo-N-(3-(oxazol-5-yl)phenyl)benzenesulfonamide;
5-(dimethylamino)-N-(3-(oxazol-5-yl)phenyl)naphthalene-1-sulfonamide;
2,3,5,6-tetramethyl-N-(3-(oxazol-5-yl)phenyl)benzenesulfonamide;
2,5-dichloro-N-(3-(oxazol-5-yl)phenyl)benzenesulfonamide; or
2,3,4-trifluoro-N-(3-(oxazol-5-yl)phenyl)benzenesulfonamide.

The above disclaimed compounds within the scope of formula (I) were found in a database search using the Internet search tool SciFinder. However, for most of these compounds, no particular use was found to be indicated; in particular, there was no indication that they had ever been used in therapy, with a few exceptions:

The compound methyl 6-(4'-cyano-[1,1'-biphenyl]-4-ylsulfonamido)picolinate is disclosed in patent application WO2005060963A1, directed to treatment of e.g. diabetes, metabolic syndrome and inflammatory disorders.

The compounds ethyl 3-(5-(4,5-dimethyl-1H-pyrazol-3-yl)thiophene-2-sulfonamido)benzoate, and ethyl 3-(5-(5-methyl-1H-pyrazol-3-yl)thiophene-2-sulfonamido)benzoate are disclosed in patent application WO 2010126002 A1, directed to treatment of Alzheimer's disease.

Therefore, another object of the invention is to provide a compound of formula (I) as defined herein above, for use in therapy, provided that the compound is not:

methyl 6-(4'-cyano-[1,1'-biphenyl]-4-ylsulfonamido)picolinate;

ethyl 3-(5-(4,5-dimethyl-1H-pyrazol-3-yl)thiophene-2-sulfonamido)benzoate; or ethyl 3-(5-(5-methyl-1H-pyrazol-3-yl)thiophene-2-sulfonamido)benzoate.

In one embodiment, there is provided a compound according to formula (I) as defined herein above, for use in therapy, provided that the compound is not:

methyl 6-(4'-cyano-[1,1'-biphenyl]-4-ylsulfonamido)picolinate;

ethyl 3-(5-(4,5-dimethyl-1H-pyrazol-3-yl)thiophene-2-sulfonamido)benzoate;

ethyl 3-(5-(5-methyl-1H-pyrazol-3-yl)thiophene-2-sulfonamido)benzoate;

3-(4-(3,5-dimethyl-1H-pyrazol-1-yl)phenylsulfonamido) benzoic acid;

ethyl 2-(6-acetamidonaphthalene-2-sulfonamido)-4-methylthiazole-5-carboxylate; or ethyl 2-(6-aminonaphthalene-2-sulfonamido)-4-methylthiazole-5-carboxylate.

Another object of the invention is to provide a compound of formula (I) as defined herein above, for use in the treatment of inflammation, inflammatory disorders or cancer, provided that the compound is not methyl 6-(4'-cyano-[1,1'-biphenyl]-4-ylsulfonamido)picolinate.

Another object of the present invention relates to inhibition of the PFKFB3 and/or PFKFB4 protein with the compound as defined herein.

Thus, in one aspect, a compound as defined herein is provided for use in the treatment of a disorder related to or mediated by the PFKFB3 protein.

In another aspect, a compound as defined herein is provided, for use in the treatment of a disorder related to or mediated by the PFKFB4 protein.

Thus, the present invention provides a method of treatment of cancer and inflammation, by the inhibition of PFKFB3 and/or PFKFB4, and a compound for use in such a method. This is achieved by either a single molecule inhibiting both PFKFB3 and PFKFB4 or by separate molecules with selective specificities for either PFKFB3 or PFKFB4.

The compounds of the present invention may act as inhibitors of the PFKFB3 and/or PFKFB4 protein. In some embodiments, the compounds of the above formula can exhibit a PFKFB3 and/or PFKFB4 inhibiting activity corresponding to an $IC_{50}$ of from about 1 nM to about 15 μM; e.g., from about 2 nM to about 10 μM, from about 5 nM to about 5 μM, from about 10 nM to about 1 μM, or from about 20 nM to about 100 nM) or a lower concentration as tested in an conventional assay as will be described below.

While not wishing to be bound by theory, it is believed that the compounds described herein, by virtue of their PFKFB3 and/or PFKFB4 inhibitory activity, can be used, e.g., for the treatment or prevention of cancer and inflammation, and/or in treatment of disorders related to cancer and inflammation.

Of particular interest are tumors with elevated glucose uptake compared to normal nontumor tissues, identified by for example PET studies. These tumors include, but are not limited to breast cancer, lung cancer, prostate cancer, colorectal cancers, haematological cancers and malignant melanoma.

A further object of this invention relates to compounds of formula (I) for use as a medicament, especially for the treatment of cancer and inflammation.

In a further aspect the present invention relates to a method for the treatment or prophylaxis of a disease, disorder, or condition related to undesired activity of PFKFB3 and/or PFKFB4 (e.g., inflammatory disorder and cancer). The method includes administering to a subject (e.g., a subject in need thereof, e.g., a mammal; e.g., a human; e.g., a human having, identified as having, at risk of having, or identified as being at risk of having one or more of the diseases or disorders described herein) an effective amount of a compound of formula I or a pharmaceutically acceptable salt or prodrug thereof.

In one aspect, this invention relates to a method for the treatment or prophylaxis of cancer and inflammation, which includes administering to a subject (e.g., a subject in need of such treatment as described herein) an effective amount of a compound of formula I or a pharmaceutically acceptable salt or prodrug thereof.

In another aspect, this invention relates to a method for the treatment or prophylaxis (e.g., treatment) of cancer, which includes administering to a subject (e.g., a subject in need of such treatment as described herein) an effective amount of a compound of formula I or a pharmaceutically acceptable salt or prodrug thereof.

In some embodiments, the subject can be a subject in need of such treatment as described herein. Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject is a human.

In a further aspect, this invention relates to the use of a compound of formula I (e.g., as a medicament) or in the manufacture of a medicament containing a compound of formula I for the treatment or prophylaxis (e.g., treatment) of a disease, disorder, or condition related to undesired activity of PFKFB3 and/or PFKFB4 as described herein.

In one aspect, the invention relates to a compound (including a pharmaceutically acceptable salt thereof) of any of the formulae delineated herein (e.g., a compound having formula I, or subgenera thereof), including the specific compounds described herein); or a composition or formulation (e.g., a pharmaceutical composition or formulation) comprising a compound (including a pharmaceutically acceptable salt thereof) of any of the formulae delineated herein (e.g., a compound having formula I, or subgenera thereof), including the specific compounds described herein). In some embodiments, the composition or formulation can further include a pharmaceutically acceptable adjuvant, carrier or diluent. Any such compound can be used in the methods described herein.

BRIEF DESCRIPTION OF THE DRAWING

FIG. 1 is a bar chart representing the effect of the compound of Example 74 on cell proliferation in NUGC-3.

DETAILED DESCRIPTION OF THE INVENTION

The following definitions shall apply throughout the specification and the appended claims.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

Reference to compounds of "formula I" in embodiments herein also includes compounds of any of the formulae delineated herein.

Combinations of substituents and variables envisioned by this invention are only those that result in the formation of stable compounds. The term "stable" as used herein, refers to compounds which possess stability sufficient to allow manufacture and which maintains the integrity of the compound for a sufficient period of time to be useful for the purposes detailed herein (e.g., therapeutic administration to a subject for the treatment of cancer and inflammation). The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Unless otherwise stated or indicated, the term "$C_{1-6}$ alkyl" denotes a straight or branched alkyl group having from 1 to 6 carbon atoms. Examples of said $C_{1-6}$ alkyl include methyl, ethyl, n-propyl, iso-propyl, n-butyl, iso-butyl, sec-butyl, t-butyl and straight- and branched-chain pentyl and hexyl. Derived expressions such as "$C_{1-6}$alkoxy", "$C_{1-6}$ alkylthio" and "$C_{1-6}$ alkylamino" are to be construed accordingly where an oxy group, thio group or an amino group, respectively, is bridging the $C_{1-6}$ alkyl group to the node at which that substituent is substituted. Examples of said $C_{1-6}$ alkoxy include methoxy, ethoxy, n-propoxy, iso-propoxy, n-butoxy, iso-butoxy, sec-butoxy, t-butoxy and straight- and branched-chain pentoxy and hexoxy.

By "alkyl substituted with at least one halogen" is meant an alkyl radical of the formula $C_nX_pH_{(2n+1-p)}$—, wherein $X_p$ refers to p independently selected halogen atoms, replacing p hydrogen atoms of the alkyl radical $C_nH_{2n+1}$— at the same or different carbon atoms. An example of an alkyl substituted with at least one halogen is trifluoromethyl. The alkyl substituted with at least one halogen may be a moiety forming a part of another radical, such as in trifluoromethoxy or difluoromethoxy.

Unless otherwise stated or indicated, the term "carbamoyl" shall mean the monoacyl derivative of ammonia that corresponds to —$CONH_2$.

Unless otherwise stated or indicated, the term "halogen" (or "halo") shall mean fluorine, chlorine, bromine or iodine.

Unless otherwise stated or indicated, the term "aryl" refers to a hydrocarbon ring system having at least one aromatic ring.

The term "heteroaryl" refers to a hydrocarbon cyclic radical having at least one aromatic ring which contains at least one heteroatom such as O, N, or S. Examples of heteroaryl groups include furyl, pyrrolyl, thienyl, oxazolyl, imidazolyl, thiazolyl, pyridinyl, pyrimidinyl, quinazolinyl, and indolyl groups.

The term "heteroaromatic ring" refers to a hydrocarbon ring system having at least one aromatic ring which contains at least one heteroatom such as O, N, or S. Examples of heteroaromatic rings include furane, pyrrole, thiophene, oxazole, imidazole, thiazole, pyridine, pyrimidine, quinazoline, and indole.

The term "heterocyclyl" refers to a saturated or unsaturated hydrocarbon cyclic radical having at least one ring which contains at least one heteroatom such as O, N, or S. Examples of heterocyclyl groups include morpholinyl, pyrrolidinyl, piperazinyl and tetrahydrofuryl groups.

The term "heterocyclic ring" refers to a saturated or unsaturated hydrocarbon ring system having at least one ring which contains at least one heteroatom such as O, N, or S. Examples of heterocyclic rings include morpholine, pyrrolidine, piperazine and tetrahydrofurane.

The term "arylsulfonyl" refers to a radical of the type R—$S(O)_2$— wherein R is aryl.

The term "heteroarylsulfonyl" refers to a radical of the type R—$S(O)_2$— wherein R is heteroaryl.

The term "CO alkyl-COOR" refers to the radical —COOR, whereas the term C1 alkyl-COOR refers to the radical —$CH_2$—COOR.

The term "alkylcarbonylamino" refers to a radical of the type RC(O)NH—, wherein R is an alkyl moiety.

The term "cyclic amino" refers to a radical of the type RR'N—, wherein R and R' together with the nitrogen atom to which they are attached form a nitrogen-containing cycle.

The term "hydroxy" refer s to the radical HO—.

The term "cyano" refers to the radical NC—.

The term "C0 alkyl", as present in the expression "C0-C2 alkyl", refers to a direct, covalent bond.

The term "C0-C2 alkyl" encompasses C0 alkyl, i.e. a direct covalent bond, C1 alkyl, i.e. a methylene group —$CH_2$—, and C2 alkyl, i.e. an ethylene group —$CH_2CH_2$—.

The term dialkylamino refers to a radical RR'N—, wherein R and R' are independently selected alkyl groups.

The term "nitro" refers to the radical —$NO_2$.

The term "ethyleneoxy biradical" refers to the moiety —$CH_2$—$CH_2$—O—.

Depending on the process conditions the end products of formula (I) are obtained either in neutral or salt form. Both the free base, free acid and the salts of these end products are within the scope of the invention. Acid addition salts of the inventive compounds may in a manner known per se be transformed into the free base using basic agents such as alkali or by ion exchange. The free base obtained may also form salts with organic or inorganic acids. Alkali addition salts of the inventive compounds may in a manner known per se be transformed into the free acid by using acidic agents such as acid or by ion exchange. The free acid obtained may also form salts with organic or inorganic bases.

In the preparation of acid or base addition salts, preferably such acids or bases are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Examples of bases useful in preparing salts of the present invention include sodium hydroxide, potassium hydroxide, ammonium hydroxide, potassium carbonate, and the like.

Throughout the specification and the appended claims, a given chemical formula or name shall also encompass all salts, hydrates, solvates, N-oxides and prodrug forms thereof. Further, a given chemical formula or name shall encompass all stereoisomeric forms thereof. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometric isomers, which can be present in their pure cis or trans forms or as mixtures of those.

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, 8th ed., McGraw-Hill, Int. Ed. 1992, "Biotransformation of Drugs", p. 13-15.

Pharmaceutical formulations are usually prepared by mixing the active substance, i.e. a compound of the invention, or a pharmaceutically acceptable salt thereof, with conventional pharmaceutical excipients. The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

For clinical use, the compounds of the invention are formulated into pharmaceutical formulations for oral, rectal, parenteral or other mode of administration. These pharmaceutical preparations are a further object of the invention.

For cancer therapy administration of the compounds of the present invention may be by in Usually the amount of active compounds is between 0.1-95% by weight of the preparation, preferably between 0.2-20% by weight in preparations for parenteral use and preferably between 1 and 50% by weight in preparations for oral administration.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral, e.g. intravenous, administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The compounds of the present invention may also be used or administered in combination with one or more additional therapeutically active agents, e.g. drugs useful in the treatment of inflammation and inflammatory diseases or cancer. The components may be in the same formulation or in separate formulations for administration simultaneously or sequentially.

Accordingly, in a further aspect of the invention, there is provided a combination product comprising:
(A) a compound of the invention, as defined herein; and
(B) another therapeutic agent, e.g. one that is useful in the treatment of, inflammation, inflammatory diseases, or cancer; whereby (A) and (B) is formulated in admixture with a pharmaceutically acceptable excipient.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent, and a pharmaceutically acceptable excipient, e.g. an adjuvant, diluent or carrier; and
(2) a kit of parts comprising, as components:
(a) a pharmaceutical formulation including a compound of the invention, as defined herein, in admixture with a pharmaceutically acceptable excipient, e.g. an adjuvant, diluent or carrier; and
(b) a pharmaceutical formulation including another therapeutic agent in admixture with a pharmaceutically acceptable excipient, e.g. an adjuvant, diluent or carrier, which components (a) and (b) are each provided in a form that is suitable for administration in conjunction with the other.

The compounds of the present invention may also be used or administered in combination with other treatment such as irradiation for the treatment of cancer.

As noted herein above, according to one aspect, a compound of formula (I)

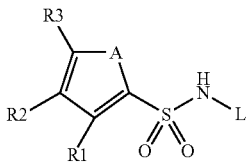
(I)

as defined herein, is provided.

In a compound of the general formula (I), $R^1$ is selected from H; halogen, e.g. F and Cl; and C1-C6 alkyl, e.g. C1-C3 alkyl, optionally substituted with at least one halogen, e.g. F. In some embodiments, $R^1$ is selected from H and C1-C6 alkyl, e.g. C1-C3 alkyl, optionally substituted with at least one halogen. In some other embodiments, $R^1$ is selected from H and halogen.

In some embodiments, $R^1$ is selected from H, halogen, and methyl, optionally substituted with at least one halogen, e.g. F. For example $R^1$ may be selected from H, F, Cl, $CH_3$ and $CF_3$. In some embodiments, $R^1$ is H. In some other embodiments, $R^1$ is $CH_3$, optionally substituted with at least one halogen, e.g. $R^1$ is selected from $CH_3$ and $CF_3$. In some other embodiments, $R^1$ is $CH_3$.

In some embodiments, $R^1$ is selected from halogen, e.g. F and Cl; and C1-C6 alkyl, e.g. C1-C3 alkyl, optionally substituted with at least one halogen. For example, R1 may be selected from F, Cl, $CH_3$ and $CF_3$.

In other embodiments $R^1$ and $R^2$ together with the carbon atoms to which they are attached form a benzene ring optionally substituted with at least one $R^6$; or a 5- or 6-membered heteroaromatic or heterocyclic ring, optionally substituted with at least one $R^6$.

For example, $R^1$ and $R^2$ together with the carbon atoms to which they are attached may form a a 5- or 6-membered heteroaromatic or heterocyclic ring, optionally substituted with at least one $R^6$, e.g. a 5-membered heteroaromatic or heterocyclic ring, such as 1,2,5-oxadiazole. In some embodiments, $R^1$ and $R^2$ form a 5- or 6-membered heteroaromatic ring optionally substituted by $R^6$.

In a compound of formula (I) as defined herein above, $R^2$ and $R^3$ are independently selected from H; halogen; C1-C6 alkyl, optionally substituted with at least one halogen; phenyl optionally substituted with at least one $R^6$; 5- or 6-membered heteroaryl optionally substituted with at least one $R^6$; and 5- or 6-membered arylsulfonyl or heteroarylsulfonyl optionally substituted with at least one $R^6$; or $R^2$ and $R^3$ form, together with the carbon atoms to which they are attached, a benzene ring, optionally substituted with at least one $R^6$; or a 5- or 6-membered heteroaromatic or heterocyclic ring, optionally substituted with at least one $R^6$.

In some embodiments, one of $R^2$ and $R^3$ is a non-cyclic moiety selected from H; halogen; and C1-C6 alkyl optionally substituted with at least one halogen, e.g. F; and the other one is a cyclic moiety selected from phenyl optionally substituted with at least one $R^6$; 5- or 6-membered heteroaryl optionally substituted with at least one $R^6$; and 5- or 6-membered arylsulfonyl or heteroarylsulfonyl optionally substituted with at least one $R^6$.

For example, the non-cyclic moiety may be selected from H and halogen, e.g. H, F, Cl, and Br, in particular H, F and Cl, e.g. H and Cl; or may be selected from H and C1-C6 alkyl optionally substituted with at least one halogen, e.g. from H and C1-C3 alkyl optionally substituted with at least one halogen, such as H, CH3 and CF3.

When one of $R^2$ and $R^3$ is a cyclic moiety, this moiety is selected from phenyl optionally substituted with at least one $R^6$; 5- or 6-membered heteroaryl optionally substituted with at least one $R^6$; and 5- or 6-membered arylsulfonyl or heteroarylsulfonyl optionally substituted with at least one $R^6$.

In some embodiments, the cyclic moiety is selected from phenyl optionally substituted with at least one $R^6$; and 5- or 6-membered heteroaryl optionally substituted with at least one $R^6$.

For example, the cyclic moiety may be phenyl optionally substituted with at least one $R^6$.

When the cyclic moiety is a heteroaryl or heterocyclyl, this e.g. may contain 1-5, or 1-4, or 1, 2 or 3 heteroatoms selected from N, O and S. For example, the cyclic moiety may be a heteroaryl, e.g. selected from oxazolyl, pyrimidinyl, thiazolyl, thiadiazolyl, isoxazolyl and pyrimidinyl.

In some embodiments, one of $R^2$ and $R^3$ is H and the other one is selected from phenyl optionally substituted with at least one $R^6$; 5- or 6-membered heteroaryl optionally substituted with at least one $R^6$; and 5- or 6-membered arylsulfonyl or heteroarylsulfonyl optionally substituted with at least one $R^6$. For example, $R^2$ is H and $R^3$ is phenyl optionally substituted with at least one $R^6$. In some other embodiments, $R^2$ is phenyl optionally substituted with at least one $R^6$ and $R^3$ is H.

In other embodiments, $R^2$ is a cyclic moiety as defined herein above and $R^3$ is selected from H; halogen and optionally substituted C1-C6 alkyl, e.g. H, halogen and optionally substituted C1-C3 alkyl; e.g. H, F, Cl, Br, CH3 and CF3, in particular H and halogen, and more particularly H.

In other embodiments, $R^3$ is a cyclic moiety as defined herein above and $R^2$ is selected from H; halogen and optionally substituted C1-C6 alkyl, e.g. H, halogen and optionally substituted C1-C3 alkyl; e.g. H, F, Cl, Br, CH3 and CF3, in particular H and halogen, and more particularly H.

In some embodiments, both $R^2$ and $R^3$ are independently selected from H, halogen and C1-C6 alkyl optionally substituted with at least one halogen. In these embodiments, A is a double bond, and they will be described more fully herein below.

In some embodiments, $R^2$ and $R^3$ together with the carbon atoms to which they are attached form a benzene ring, which ring is optionally substituted with at least one $R^6$, e.g. 1-3 or 1-2 $R^6$. In this case, the moiety containing A may be represented by the formula (II)

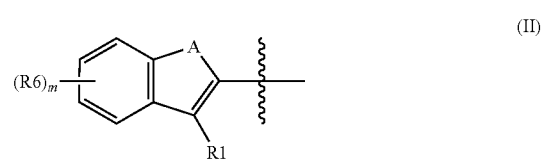
(II)

wherein A, $R^1$ and $R^6$ are as defined herein, and m is an integer of e.g. from 0 to 3, or from 0 to 2, in particular 0 or 1, representing the number of substituents $R^6$ attached to the benzene ring.

In some embodiments, m is 0; in some other embodiments m is an integer of from 1 to 3, e.g. m is 1 or 2, or m is 1.

When the moiety containing A is represented by the formula (II), the compound of formula (I) may be represented by formula (Ia)

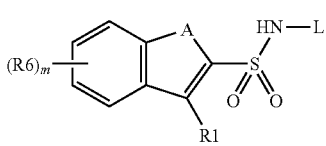

(Ia)

wherein $R^1$, $R^6$, A, L and m are as defined herein.

In some embodiments, where m in formula (II) is 1, the moiety of formula (II) more specifically may be according to formula (IIa)

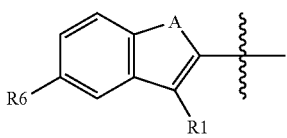

(IIa)

in which case the compound of formula (Ia) may be represented by formula (Iaa)

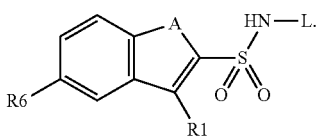

(Iaa)

In some other embodiments, where m is 1 in formula (II) is 1, the moiety of formula (II) may be according to formula (IIb)

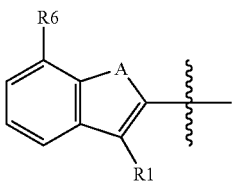

(IIb)

in which case the compound of formula (Ia) may be represented by formula (Iab)

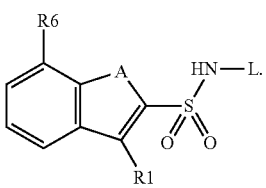

(Iab)

Any substituent $R^6$, when present in a compound of formula (I), is independently selected from C1-C6 alkyl, e.g. C1-C3 alkyl, such as methyl or isopropyl; halogen, e.g. F, Cl or Br; hydroxy, C1-C6 alkoxy, e.g. C1-C3 alkoxy, e.g. methoxy; C1-C6 alkylthio, e.g. C1-C3 alkylthio, e.g. methylthio; $R^{10}R^{11}N$, carbamoyl, and C1-C6 alkylcarbonylamino, e.g. C1-C3 alkylcarbonylamino, e.g. methylcarbonylamino; or from an ethyleneoxy biradical; wherein any alkyl, alone or as part of any of the aforementioned groups, is optionally substituted with at least one halogen, e.g. F, such as in trifluoromethyl; and wherein $R^{10}$ and $R^{11}$ are independently selected from H and C1-C6 alkyl, e.g. C1-C3 alkyl, such as methyl, or $R^{10}$ and $R^{11}$ form, together with the nitrogen to which they are attached, a 5- or 6-membered cyclic amino, optionally containing one other heteroatom, e.g. tetrahydropyrrol-1-yl, morpholinyl, or piperazin-1-yl.

In some embodiments, each $R^6$ is independently selected from C1-C6 alkyl, e.g. C1-C3 alkyl, such as methyl or isopropyl; halogen, e.g. F, Cl or Br; C1-C6 alkoxy, e.g. C1-C3 alkoxy, e.g. methoxy; and C1-C6 alkylthio, e.g. C1-C3 alkylthio, e.g. methylthio; wherein any alkyl, alone or as part of any of the aforementioned groups, is optionally substituted with at least one halogen, e.g. F, such as in trifluoromethyl.

In some embodiments, each $R^6$ is independently selected from C1-C6 alkyl, e.g. C1-C3 alkyl, such as methyl or isopropyl and halogen, e.g. F, Cl or Br.

In some embodiments, each $R^6$ is selected from C1-C6 alkyl, e.g. C1-C3 alkyl, such as methyl or isopropyl; halogen; C1-C6 alkoxy, e.g. C1-C3 alkoxy, such as methoxy; $R^{10}R^{11}N$, e.g. $NH_2$, and C1-C6 alkylcarbonylamino, e.g. C1-C3 alkylcarbonylamino, e.g. methylcarbonylamino. In some embodiments, each $R^6$ is selected from halogen and C1-C6 alkoxy, e.g. C1-C3 alkoxy, such as methoxy.

One moiety of the compound of formula (I) is the 5- or 6-membered ring represented by L (a) to (d):

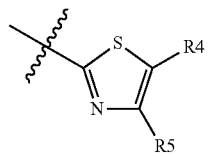

(a)

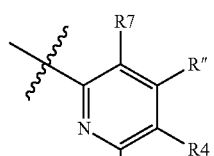

(b)

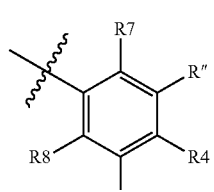

(c)

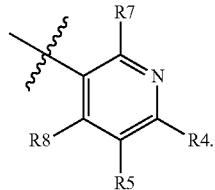

(d)

In some embodiments, L is substituted with a group C0-C1 alkyl-$COOR^{12}$, wherein $R^{12}$ is as defined herein above, i.e. $R^{12}$ is selected from H, C1-C6 alkyl; heteroaryl-C0-C2 alkyl; (C1-C3 alkoxy)$_p$C1-C3 alkyl, wherein p is 1 or 2; aryl-C0-C2 alkyl, e.g. phenyl and benzyl; heterocyclyl-C0-C2 alkyl; and C1-C6 dialkylamino-C1-C6 alkyl, wherein any cyclic moiety is optionally substituted with C1-C6 alkyl, e.g. C1-C3 alkyl, such as methyl.

For example, $R^{12}$ may be selected from H, methyl, ethyl, n-propyl, isopropyl, n-butyl, n-pentyl, n-hexyl, 2-(1H-pyrrol-1-yl)ethyl, 2-methoxyethyl, phenyl, benzyl, tetrahydrofuran-3-yl, (tetrahydrofuran-3-yl)methyl, and 3-(dimethylamino)propyl.

In some embodiments, $R^{12}$ is selected from H and C1-C6 alkyl.

In some embodiments, $R^{12}$ is H. In some other embodiments, $R^{12}$ is as defined herein above, but is not H.

In some embodiments, L is selected from a thiazolyl ring and a phenyl ring, as defined herein above under (a) and (c), respectively.

In some other embodiments, L is selected from a pyridinyl ring, as defined herein above under (b) and (d), respectively.

In some embodiments L is a thiazolyl ring (a)

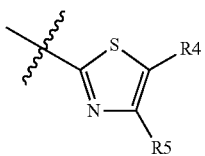

wherein
$R^4$ is $COOR^{12}$; and $R^5$ is selected from H and C1-C6 alkyl; or
$R^4$ is selected from H and C1-C6 alkyl; and $R^5$ is $COOR^{12}$.

In these embodiments, when $R^4$ or $R^5$ is a C1-C6 alkyl group, said group e.g. may be a C1-C3 alkyl, e.g. methyl.

When $R^4$ or $R^5$ is $COOR^{12}$, $R^{12}$ is as generally defined herein above. In some embodiments, when L is (a), $R^{12}$ is selected from H and C1-C6 alkyl, or H and C1-C3 alkyl, e.g. H, methyl and ethyl. In some embodiments, $R^{12}$ is H; i.e. $R^4$ or $R^5$ is a carboxy functionality; in others $R^{12}$ is different from H, i.e. $R^4$ or $R^5$ is an ester functionality.

In some embodiments, $R^4$ is $COOR^{12}$ and $R^5$ is selected from H and C1-C6 alkyl, in which which case L is (a1)

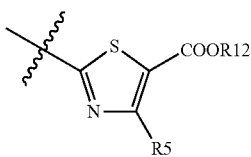

wherein $R^5$ and $R^{12}$ are as defined herein above.

In some other embodiments, $R^4$ is selected from H and C1-C6 alkyl and $R^5$ is $COOR^{12}$; in which case L is a thiazolyl (a2)

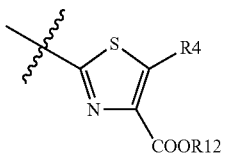

wherein $R^5$ and $R^{12}$ are as defined herein above.

In some embodiments, L is a 2-pyridinyl (b)

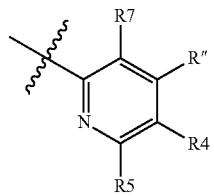

wherein
$R^4$ is selected from H and C1-C6 alkyl;
$R^5$ is selected from H and C1-C6 alkyl; and R" is selected from C0-C1 alkyl-$COOR^{12}$; or
$R^5$ is $COOR^{12}$; and R" is selected from H and C1-C6 alkyl; and
$R^7$ is selected from H, C1-C6 alkyl, and nitro.

In some other embodiments, L is a 2-pyridinyl (b) wherein
$R^4$ is selected from H and C1-C6 alkyl;
$R^5$ is selected from H and C1-C6 alkyl; and R" is selected from C0-C1 alkyl-$COOR^{12}$; or
$R^5$ is selected from $COOR^{12}$; and R" is selected from H and C1-C6 alkyl; and
$R^7$ is selected from H and C1-C6 alkyl.

In some embodiments, $R^5$ is selected from H and C1-C6 alkyl; and R" is selected from C0-C1 alkyl-$COOR^{12}$, e.g. from $COOR^{12}$.

In some other embodiments, $R^5$ is $COOR^{12}$; and R" is selected from H and C1-C6 alkyl.

In any of these embodiments, when either of $R^4$, $R^5$, R" and $R^7$ is a C1-C6 alkyl group, said group e.g. may be a C1-C3 alkyl group, such as methyl.

In some embodiments, $R^4$ is H, and $R^5$, R" and $R^7$ are as defined in any of the above embodiments.

In some embodiments, $R^5$ is H, and $R^4$, R" and $R^7$ are as defined in any of the above embodiments.

In some embodiments, $R^7$ is H, and $R^4$, $R^5$ and R" are as defined in any of the above embodiments.

In some embodiments, $R^4$ is H; $R^5$ is H and R" is selected from C0-C1 alkyl-$COOR^{12}$; or $R^5$ is $COOR^{12}$ and R" is H; and $R^7$ is H.

When, in a pyridine as defined in (b), $R^5$ or R" is $COOR^{12}$ or C0-C1 alkyl-$COOR^{12}$, respectively, $R^{12}$ is as generally defined herein above. In some embodiments, $R^{12}$ is selected from H and C1-C6 alkyl, or H and C1-C3 alkyl, e.g. H, methyl and ethyl. In some embodiments, $R^{12}$ is H, in others $R^{12}$ is different from H. For example, $R^4$ is H; $R^5$ is H; R" is COOH and $R^7$ is H; or $R^4$ is H, $R^5$ is COOH, R" is H; and $R^7$ is H.

In some embodiments, L is a phenyl ring (c)

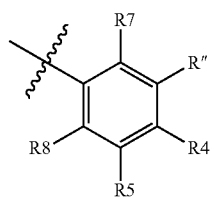

wherein
$R^4$ is selected from H, hydroxy and C1-C6 alkyl;
$R^5$ is selected from H, C1-C6 alkyl; and R" is selected from C0-C1 alkyl-$COOR^{12}$; or
$R^5$ is selected from $COOR^{12}$, oxazol-5-yl and tetrazol-5-yl, said oxazol-5-yl and tetrazol-5-yl optionally being substituted by $R^9$; and R" is selected from H, C1-C6 alkyl, and nitro;

R$^7$ is selected from H, C1-C6 alkyl, and nitro; and
R$^8$ is selected from H, hydroxy, and C1-C6 alkyl.
In some of these embodiments,
R$^4$ is selected from H and C1-C6 alkyl;
R$^5$ is selected from oxazol-5-yl and tetrazol-5-yl, said oxazol-5-yl and tetrazol-5-yl optionally being substituted by R$^9$;
R" is selected from H and C1-C6 alkyl;
R$^7$ is selected from H and C1-C6 alkyl; and
R$^8$ is selected from H and C1-C6 alkyl.
For example
R$^4$ is H;
R$^5$ is selected from oxazol-5-yl and tetrazol-5-yl, said oxazol-5-yl and tetrazol-5-yl optionally being substituted by R$^9$; more preferably, R$^5$ is tetrazol-5-yl, such as 1H-tetrazol-5-yl;
R" is H;
R$^7$ is H; and
R$^8$ is H.
When R$^5$ is tetrazol-5-yl it may be 1H-tetrazol-5-yl or 2H-tetrazol-5-yl, but preferably is 1H-tetrazol-5-yl.
When R$^5$ is tetrazolyl substituted by at least one R$^9$, it e.g. may be 2H-tetrazol-5-yl substituted by at least one R$^9$.
In some embodiments,
R$^4$ is selected from H and C1-C6 alkyl;
R$^5$ is 1H-tetrazol-5-yl
R" is selected from H and C1-C6 alkyl;
R$^7$ is selected from H and C1-C6 alkyl; and
R$^8$ is selected from H and C1-C6 alkyl;
and L may then be represented as a phenyl ring (c1)

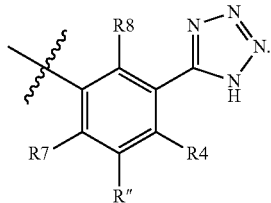

For example
R$^4$ is H;
R$^5$ is 1H-tetrazol-5-yl;
R" is H;
R$^7$ is H; and
R$^8$ is H; i.e. L may be represented as a phenyl ring (c2)

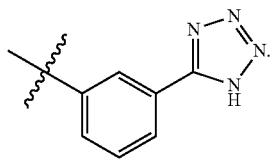 [SMILES: *c1cccc(-c2nnn[nH]2)c1]

In some other of those embodiments where L is (c),
R$^4$ is selected from H, hydroxy and C1-C6 alkyl;
R$^5$ is selected from H and C1-C6 alkyl; and R" is selected from C0-C1 alkyl-COOR$^{12}$; or
R$^5$ is COOR$^{12}$; and R" is selected from H, C1-C6 alkyl, and nitro;
R$^7$ is selected from H, C1-C6 alkyl, and nitro; and
R$^8$ is selected from H, hydroxy, and C1-C6 alkyl.

Preferably, in these embodiments, R$^4$ and R$^8$ are not both hydroxy, i.e.
R$^4$ is selected from H, hydroxy and C1-C6 alkyl; and R$^8$ is selected from H and C1-C6 alkyl;
or R$^4$ is selected from H and C1-C6 alkyl; and R$^8$ is selected from H and C1-C6 alkyl.
In some of these embodiments
R$^4$ is selected from H and C1-C6 alkyl;
R$^5$ is selected from H and C1-C6 alkyl; and R" is selected from C0-C1 alkyl-COOR$^{12}$; or
R$^5$ is COOR$^{12}$; and R" is selected from H and C1-C6 alkyl;
R$^7$ is selected from H and C1-C6 alkyl; and
R$^8$ is selected from H and C1-C6 alkyl.
In some other of these embodiments.
R$^4$ is selected from H and hydroxy;
R$^5$ is selected from H and C1-C6 alkyl; and R" is selected from C0-C1 alkyl-COOR$^{12}$; or
R$^5$ is COOR$^{12}$; and R" is selected from H, C1-C6 alkyl, and nitro;
R$^7$ is H; and
R$^8$ is selected from H and hydroxy.
For example,
R$^4$ is selected from H and hydroxy; and R$^8$ is H; or
R$^4$ is H; and R$^8$ is selected from H and hydroxy;
R$^5$ is selected from H and C1-C6 alkyl; and R" is selected from C0-C1 alkyl-COOR$^{12}$; or
R$^5$ is COOR$^{12}$; and R" is selected from H, C1-C6 alkyl, and nitro; and
R$^7$ is H.
In some of the above embodiments, R$^5$ is COOR$^{12}$.
For example, in some embodiments,
R$^4$ is selected from H, hydroxy and C1-C6 alkyl; e.g. from H and hydroxy; in particular H;
R$^5$ is COOR$^{12}$;
R" is selected from H, C1-C6 alkyl, and nitro; e.g. from H and C1-C6 alkyl;
R$^7$ is selected from H, C1-C6 alkyl, and nitro; e.g. from H and C1-C6 alkyl; and
R$^8$ is selected from H, hydroxy, and C1-C6 alkyl; e.g. from H and hydroxy; in particular H;
L may then be represented as a phenyl ring (c3)

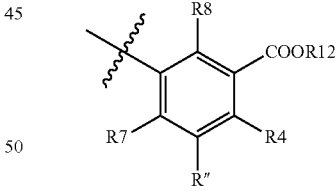

wherein R$^4$, R$^7$, R$^8$, R$^{12}$ and R" is as defined herein above.
In those embodiments where R$^4$, R$^7$, R$^8$ and R" are all H, L may be represented as a phenyl ring (c4)

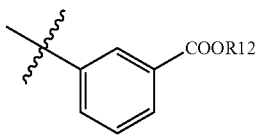

wherein R$^{12}$ is as defined herein above.
In some embodiments, R" is C0-C1 alkyl-COOR$^{12}$. For example, R" may be COOR$^{12}$.

When either $R^5$ or R", but preferably $R^5$, is $COOR^{12}$ or, in the case of R", —$CH_2COOR^{12}$, $R^{12}$ may be as defined herein above, i.e. selected from H, C1-C6 alkyl; heteroaryl-C0-C2 alkyl; (C1-C3 alkoxy)$_p$C1-C3 alkyl, wherein p is 1 or 2; aryl-C0-C2 alkyl, e.g. phenyl and benzyl; heterocyclyl-C0-C2 alkyl; and C1-C6 dialkylamino-C1-C6 alkyl, wherein any cyclic moiety is optionally substituted with C1-C6 alkyl, e.g. C1-C3 alkyl, such as methyl. In some embodiments, $R^{12}$ is H, in others $R^{12}$ is different from H.

In some embodiments, L is a 3-pyridinyl (d)

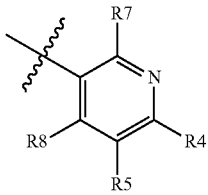

wherein $R^4$ is selected from H and C1-C6 alkyl; and $R^5$ is $COOR^{12}$;

$R^7$ is selected from H, C1-C6 alkyl, and nitro; and $R^8$ is selected from H, hydroxy, and C1-C6 alkyl.

Thus, when L is a 3-pyridinyl group, this group may be represented as (d1)

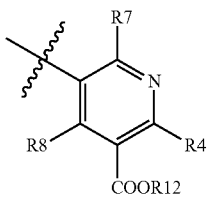

wherein $R^4$, $R^7$, $R^8$ and $R^{12}$ are as defined herein above.

In some of the embodiments wherein L is (d1), $R^4$ is selected from H and C1-C6 alkyl;

$R^7$ is selected from H and C1-C6 alkyl;

$R^8$ is selected from H and C1-C6 alkyl; and and $R^{12}$ is as defined herein above.

In some of the embodiments wherein L is (d1), $R^4$ is selected from H and C1-C6 alkyl;

$R^7$ is selected from H and C1-C6 alkyl;

$R^8$ is selected from H and hydroxy; and $R^{12}$ is as defined herein above.

For example, $R^4$, $R^7$ and $R^8$ may all be H.

In (d1), $R^{12}$ is as generally defined herein above. In some embodiments, $R^{12}$ is selected from H and C1-C6 alkyl, or H and C1-C3 alkyl, e.g. H and methyl. In some embodiments, $R^{12}$ is H, in others $R^{12}$ is different from H.

Embodiments Wherein a in Formula (I) is CR'=CR'

In some embodiments, A in formula (I) is CR'=CR'. The compound of formula (I) may then be represented by formula (Ib)

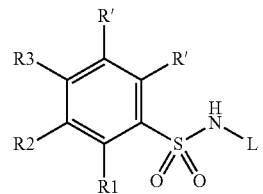

wherein R', $R^1$, $R^2$, $R^3$, and L are as defined herein above.

In a compound of formula (Ib) as defined herein above, each R' is independently selected from H; halogen; and C1-C6 alkyl optionally substituted with at least one halogen. In some embodiments, each R' is selected from H; halogen; and C1-C3 alkyl, e.g. methyl, optionally substituted with at least one halogen, e.g. F. For example, each R' may be independently selected from H, F, Cl, $CH_3$ and $CF_3$; e.g. each R' may be independently selected from H, Cl and $CH_3$. In some embodiments, the R' that is in meta position, on the phenyl ring, which may be termed $R'^{meta}$, is hydrogen. In some embodiments, the R' that is in ortho position on the phenyl ring, which may be termed $R'^{ortho}$, is different from hydrogen.

In a compound of formula (Ib), $R^2$ may form a ring with either $R^1$ or $R^3$, or may be a radical selected from H, halogen, C1-C6 alkyl optionally substituted with at least one halogen; phenyl optionally substituted with at least one $R^6$; 5- or 6-membered heteroaryl optionally substituted with at least one $R^6$; and 5- or 6-membered arylsulfonyl or heteroarylsulfonyl, optionally substituted with at least one $R^6$.

In some embodiments, $R^2$ is a radical selected from H, halogen, C1-C6 alkyl optionally substituted with at least one halogen; phenyl optionally substituted with at least one $R^6$; and 5- or 6-membered heteroaryl optionally substituted with at least one $R^6$.

In some embodiments $R^2$ is selected from H; halogen, such as Cl; C1-C6 alkyl, e.g. C1-C3 alkyl, such as $CH_3$, optionally substituted with at least one halogen; and phenyl, optionally substituted with at least one $R^6$, e.g. 1 or 2 $R^6$, such as one $R^6$ in 4-position (para position) or two $R^6$, in 3- and 5-position (meta, meta' position). For example, $R^2$ may be selected from H, Cl, phenyl, 4-fluorophenyl, 4-chlorophenyl, 4-methylphenyl, 4-trifluorophenyl, 4-methoxyphenyl, 3,4-dichlorophenyl and 3,5-dichlorophenyl.

In some embodiments, $R^2$ is selected from H and phenyl optionally substituted with at least one $R^6$; 5- or 6-membered heteroaryl optionally substituted with at least one $R^6$; and 5- or 6-membered arylsulfonyl or heteroarylsulfonyl, optionally substituted with at least one $R^6$.

In some embodiments, $R^2$ is selected from H and phenyl optionally substituted with at least one $R^6$; and 5- or 6-membered heteroaryl optionally substituted with at least one $R^6$.

In some embodiments, $R^2$ is selected from phenyl optionally substituted with at least one $R^6$; and 5- or 6-membered heteroaryl optionally substituted with at least one $R^6$, in particular phenyl optionally substituted with at least one $R^6$, e.g. phenyl substituted with 1 or 2 $R^6$.

In a compound of formula (Ib), $R^3$ may form a ring with $R^2$, or may be a radical selected from H, halogen, C1-C6 alkyl optionally substituted with at least one halogen; phenyl optionally substituted with at least one $R^6$; 5- or 6-membered heteroaryl optionally substituted with at least one $R^6$; and 5- or 6-membered arylsulfonyl or heteroarylsulfonyl, optionally substituted with at least one $R^6$.

In some embodiments of a compound of formula (Ib), $R^3$ is a radical selected from H, halogen, C1-C6 alkyl optionally substituted with at least one halogen; phenyl optionally substituted with at least one $R^6$; and 5- or 6-membered heteroaryl optionally substituted with at least one $R^6$.

In some particular embodiments of a compound of formula (Ib), $R^3$ is a radical selected from H, halogen, C1-C6 alkyl optionally substituted with at least one halogen; phenyl optionally substituted with at least one $R^6$; 5- or 6-membered heteroaryl, such as oxazol-5-yl, optionally substituted with at least one $R^6$. For example, $R^3$ may be a radical selected from H, halogen, such as F, Cl or Br; and phenyl optionally substituted with at least one $R^6$.

As an example, $R^3$ may be selected from H, F, Cl, Br, $CH_3$, $CF_3$, phenyl, oxazol-5-yl, 4-methoxyphenyl and 3,4-dichlorophenyl.

In some embodiments, when $R^3$ is a phenyl radical, it is substituted with at least one $R^6$, e.g. 1 or 2 $R^6$.

Preferably, in a compound of formula (Ib) at least one of $R^2$ and $R^3$ is selected from H, halogen and C1-C6 alkyl optionally substituted with at least one halogen.

Thus in one embodiment of a compound of formula (Ib), $R^2$ is selected from H, halogen and C1-C6 alkyl optionally substituted with at least one halogen, e.g. $R^2$ is H, and $R^3$ is as defined herein above.

In another embodiment of a compound of formula (Ib), $R^3$ is selected from H, halogen and C1-C6 alkyl, optionally substituted with at least one halogen, e.g. $R^3$ is H, and $R^2$ is as defined herein above.

In some embodiments, L is a phenyl ring (c), as described herein above, and the compound of formula (b) may then be represented by formula (Iba)

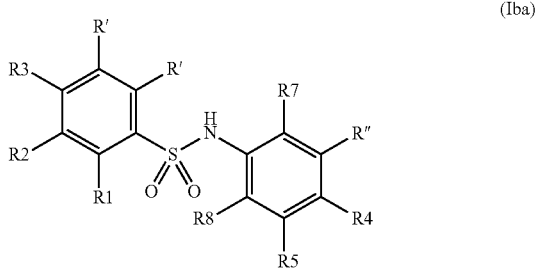

(Iba)

wherein $R^1$, $R^2$, $R^3$, $R^4$, $R^5$, $R^7$, $R^8$ and R" are as defined herein above.

In some embodiments, L is a phenyl ring (c1) as described herein above, and the compound of formula (Ib) may then be represented by formula (Ibb)

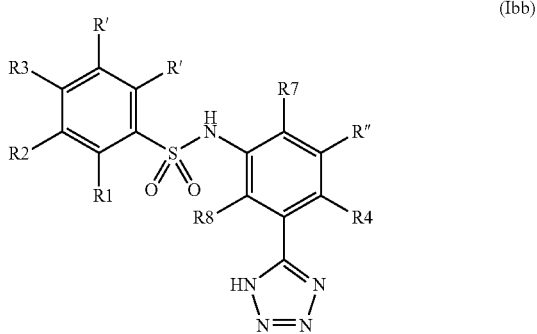

(Ibb)

wherein R', $R^1$, $R^2$, $R^3$, $R^4$, $R^7$, $R^8$ and R" are as defined herein above.

In some other embodiments, L is a phenyl ring (c3) as described herein above, and the compound of formula (Ib) may then be represented by formula (Ibc)

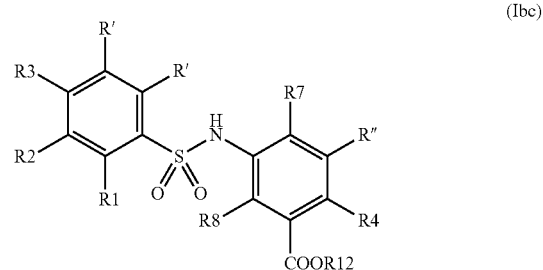

(Ibc)

wherein R', $R^1$, $R^2$, $R^3$, $R^4$, $R^7$, $R^8$, $R^{12}$ and R" are as defined herein above.

In some embodiments of a compound of formula (Ib), either $R^1$ and $R^2$, or $R^2$ and $R^3$, together with the carbon atoms to which they are attached, form a benzene ring optionally substituted with at least one $R^6$, or a 5- or 6-membered heterocyclic ring or heteroaromatic ring, optionally substituted with at least one $R^6$.

In some embodiments of a compound of formula (Ib), in particular in those embodiments where the compound is according to formula (Ibb), both $R^2$ and $R^3$ are selected from H, halogen, and C1-C6 alkyl optionally substituted with at least one halogen. In these embodiments, at least one of $R^1$ and the R' that is attached to the carbon atom adjacent to the sulphonamide bond, i.e. $R'^{ortho}$, is different from H.

For example, in some embodiments, either $R^1$ and $R^2$ or $R^2$ and $R^3$, e.g. $R^2$ and $R^3$, may form a benzene ring, optionally substituted with at least one $R^6$. In some embodiments, $R^1$ and $R^2$ or $R^2$ and $R^3$, e.g. $R^2$ and $R^3$, form a benzene ring, optionally substituted with at least one $R^6$.

In some embodiments, when $R^1$ and $R^2$ or $R^2$ and $R^3$, e.g. $R^2$ and $R^3$, form a benzene ring, said ring is substituted with 1 or 2 $R^6$.

Embodiments Wherein a in Formula (I) is Either O or S

In some embodiments, A in formula (I) is either O or S, in particular S.

In these embodiments $R^1$ is selected from H; halogen; and C1-C6 alkyl optionally substituted with at least one halogen; or $R^1$ and $R^2$ form, together with the carbon atoms to which they are attached, a benzene ring optionally substituted with at least one $R^6$; or a 5- or 6-membered heteroaromatic or heterocyclic ring, optionally substituted with at least one $R^6$;

$R^2$ and $R^3$ are independently selected from H; halogen; C1-C6 alkyl optionally substituted with at least one halogen; phenyl optionally substituted with at least one $R^6$; 5- or 6-membered heteroaryl optionally substituted with at least one $R^6$; and 5- or 6-membered arylsulfonyl or heteroarylsulfonyl, optionally substituted with at least one $R^6$; provided that at least one of $R^2$ and $R^3$ is selected from said phenyl, heteroaryl, arylsulfonyl and heteroarylsulfonyl, and when L is (a), neither $R^2$ nor $R^3$ is unsubstituted phenyl; or $R^2$ and $R^3$ form, together with the carbon atoms to which they are attached, a benzene ring optionally substituted with at least one $R^6$; or a 5- or 6-membered heteroaromatic or heterocyclic ring, optionally substituted with at least one $R^6$.

In some embodiments, $R^1$ is selected from H; halogen; and C1-C6 alkyl optionally substituted with at least one halogen; and $R^2$ and $R^3$ are independently selected from H; halogen; C1-C6 alkyl optionally substituted with at least one halogen; phenyl optionally substituted with at least one $R^6$; 5- or 6-membered heteroaryl optionally substituted with at least one $R^6$; and 5- or 6-membered arylsulfonyl or heteroarylsulfonyl, optionally substituted with at least one $R^6$; provided that at least one of $R^2$ and $R^3$ is selected from said phenyl, heteroaryl, arylsulfonyl and heteroarylsulfonyl, and when L is (a), neither $R^2$ nor $R^3$ is unsubstituted phenyl; or $R^2$ and $R^3$ form, together with the carbon atoms to which they are attached, a benzene ring optionally substituted with at least one $R^6$; or a 5- or 6-membered heteroaromatic or heterocyclic ring, optionally substituted with at least one $R^6$.

In some embodiments, $R^2$ is a radical selected from H; halogen; and C1-C6 alkyl optionally substituted with at least one halogen; and $R^3$ is a radical selected from phenyl optionally substituted with at least one $R^6$; 5- or 6-membered heteroaryl optionally substituted with at least one $R^6$; and 5- or 6-membered arylsulfonyl or heteroarylsulfonyl, optionally substituted with at least one $R^6$.

In some other embodiments $R^2$ is a radical selected from phenyl optionally substituted with at least one $R^6$; 5- or 6-membered heteroaryl optionally substituted with at least one $R^6$; and 5- or 6-membered arylsulfonyl or heteroarylsulfonyl, optionally substituted with at least one $R^6$; and $R^3$ is a radical selected from H; halogen; and C1-C6 alkyl optionally substituted with at least one halogen.

For example, when either $R^2$ or $R^3$ is a radical selected from H; halogen; and C1-C6 alkyl, this radical more particularly can be H, F, Cl or C1-C3 alkyl, e.g. H, F, Cl and methyl, such as H and Cl, in particular H.

When either $R^2$ or $R^3$ is a radical selected from phenyl optionally substituted with at least one $R^6$; 5- or 6-membered heteroaryl optionally substituted with at least one $R^6$; and 5- or 6-membered arylsulfonyl or heteroarylsulfonyl, optionally substituted with at least one $R^6$, this radical in particular may be selected from phenyl or a 5- or 6-membered heteroaryl having 1-3 ring heteroatoms independently selected from N, O and S, such as 1,3-oxazolyl, 5-isoxazolyl, pyrimidinyl, 1,3-thiazolyl, 1,2,4-thiadiazolyl, isoxazolyl, e.g. 1,3-oxazol-5-yl, 5-isoxazol-3-yl, pyrimidin-4-yl, 1,3-thiazol-4-yl, 1,2,4-thiadiazol-3-yl, or isoxazol-3-yl, wherein the phenyl or heteroaryl is optionally substituted with at least one $R^6$, e.g. 1-3 $R^6$ as defined herein above.

The moiety $R^6$ may be selected from C1-C6 alkyl, halogen; hydroxy, C1-C6 alkoxy; C1-C6 alkylthio, and carbamoyl, e.g. F, Cl, OH, $CH_3S$, $CH_3O$, $CH_3$, and $CF_3$ and an ethyleneoxy biradical. Thus, when either $R^2$ or $R^3$, e.g. $R^3$, is a cyclic moiety substituted with at least one $R^6$, this cyclic moiety e.g. may be selected from 2-chlorophenyl, 3-chlorophenyl, 4-chlorophenyl, 2-methylphenyl, 4-methylphenyl, 3-trifluoromethylphenyl, 2-methoxyphenyl, 3-methoxyphenyl, 2-hydroxyphenyl, 3-carbamoylphenyl, 5-fluoro-2-methoxyphenyl, 3,5-difluorophenyl, 2,4-difluorophenyl, 3-chloro-4-fluorophenyl, 2,4-dimethoxyphenyl, 3,4-dichlorophenyl, 4-fluoro-2-methoxyphenyl, 2,3-dihydrobenzofuran-5-yl, 2-(methylthio)pyrimidin-4-yl, 2-methylsulfanylpyrimidin-4-yl, 2-methyl-1,3-thiazol-4-yl, 5-chloro-1,2,4-thiadiazol-3-yl, and 5-(trifluoromethyl)isoxazol-3-yl.

In those embodiments, wherein A is O or S, and both $R^1$ and $R^2$ are H, the compound of formula (I) may be represented by formula (Ic)

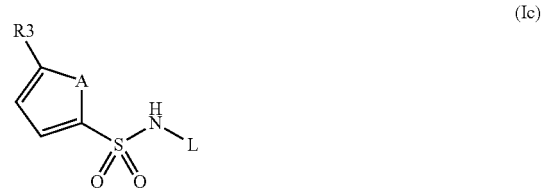

(Ic)

wherein $R^3$ is selected from phenyl optionally substituted with at least one $R^6$; 5- or 6-membered heteroaryl optionally substituted with at least one $R^6$; and 5- or 6-membered arylsulfonyl or heteroarylsulfonyl, e.g. optionally substituted with at least one $R^6$; and $R^6$ and L are as defined herein above, e.g. L is a thiazole (a) or a phenyl (c).

In some embodiments, in a compound wherein A is O or S, either $R^1$ and $R^2$ or $R^2$ and $R^3$, e.g. $R^2$ and $R^3$, together with the atoms to which they are attached, form a benzene ring optionally substituted with at least one $R^6$; or a 5- or 6-membered heteroaromatic or heterocyclic ring, optionally substituted with at least one $R^6$, in particular a benzene ring, optionally substituted with at least one $R^6$, e.g. 1-3 $R^6$ or 1-2 $R^6$, e.g. 1 $R^6$; whereby $R^6$ is as defined herein above. For example, $R^6$ may be selected from C1-C6 alkyl, such as methyl and isopropyl; halogen, such as F, Cl, and Br; C1-C6 alkoxy, such as methoxy, $R^{10}R^{11}N$, wherein $R^{10}$ and $R^{11}$ is as defined herein above, e.g. pyrrolidin-1-yl, morpholinyl, piperazin-1-yl; and C1-C6 alkylcarbonylamino, such as acetamido.

In some embodiments, in a compound of formula (I) wherein A is S or O, L is thiazolyl (a) or phenyl (c).

Thus, in some embodiments A is O or S and L is thiazolyl, and the compound of formula (I) may then be represented by formula (Id)

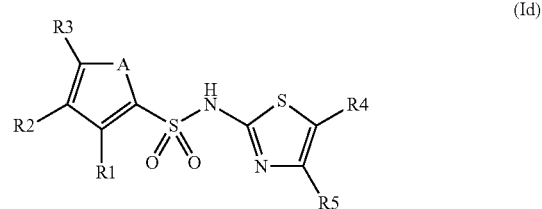

(Id)

wherein A is O or S, preferably S, and $R^1$, $R^2$, $R^3$, $R^4$ and $R^5$ are as defined herein above.

For example, in some embodiments of a compound of formula (Id), R1 is selected from H and C1-C6 alkyl, such as H and methyl; one of $R^2$ or $R^3$ is phenyl substituted with at least one $R^6$, e.g. 1-4 $R^6$, or 1-3 $R^6$, in particular 1 or 2 $R^6$, and the other one of R² and R³ is selected from H, C1-C6 alkyl and halogen, e.g. H and halogen. In these embodiments, R⁶ e.g. may be selected from halogen, e.g. F.

In some embodiments of a compound of formula (Id), R² and R³ together with the carbon atoms to which they are attached, form a benzene ring optionally substituted with at least one R⁶, in which case the compound may be represented by formula (Ida)

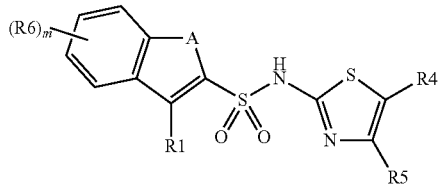

(Ida)

wherein R⁴, R⁵ and R⁶ are as defined herein above, e.g. R⁶ is selected from C1-C6 alkyl, such as isopropyl, and halogen, such Cl; and m is an integer from 0 to 4, e.g. from 0 to 3, or from 0 to 2, e.g. 0 or 1.

In those embodiments wherein A is O or S and L is a phenyl ring (c), the compound of formula (I) may be represented by formula (Ie)

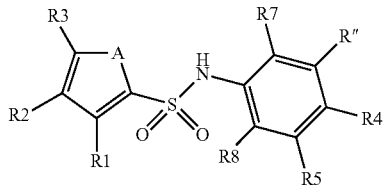

(Ie)

wherein R¹, R², R³, R⁴, R⁵, R⁷, R⁸ and R" are as defined herein above.

In some embodiments of a compound of formula (Id), R² and R³ together with the carbon atoms to which they are attached, form a benzene ring optionally substituted with at least one R⁶, in which case the compound may be represented by formula (Iea)

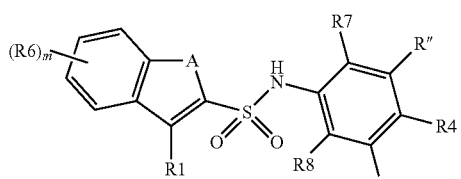

(Iea)

wherein R¹, R⁴, R⁵, R⁶, R⁷, R⁸, and R" are as defined herein above, and m is an integer from 0 to 4, e.g. from 0 to 3, or from 0 to 2, e.g. 0 or 1.

In some embodiments, L is a tetrazole-substituted phenyl ring (c1) as described herein above, and the compound of formula (Ie) is represented by formula (Ieb)

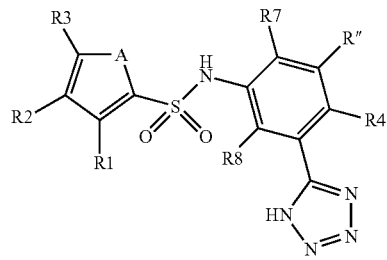

(Ieb)

wherein A is S or O, preferably S, and R¹, R², R³, R⁴, R⁷, R⁸ and R" are as defined herein above. In some particular embodiments, and the compound of formula (Iea) may be represented by formula (Iec)

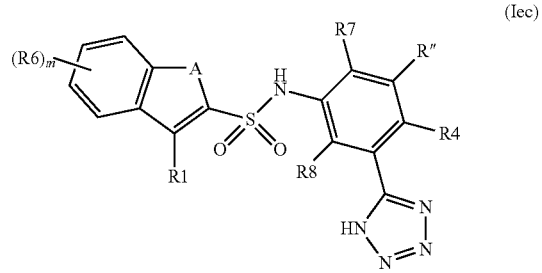

(Iec)

wherein A is S or O, preferably S, and R¹, R⁴, R⁶, R⁷, R⁸, R" and m are as defined herein above.

In some other embodiments, L is a phenyl ring (c3) as described herein above, and the compound of formula (Ie) may then be represented by formula (Ied)

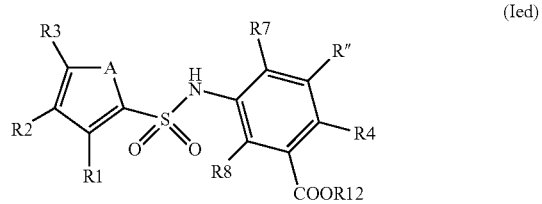

(Ied)

wherein A is S or O, preferably S, and R¹, R², R³, R⁴, R⁷, R⁸, R¹² and R" are as defined herein above.

In some other embodiments, when L is a phenyl ring (c3) as described herein above the compound of the invention may be represented by formula (Iee)

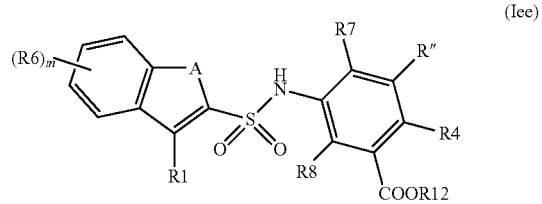

(Iee)

wherein A is S or O, preferably S, and R¹, R⁴, R⁶, R⁷, R⁸, R¹²R" and m are as defined herein above.

It should be realized that, unless the contrary is explicitly indicated or apparent from the context, any reference herein to a compound according to formula (I), should also be understood as a reference to any one of the formulas covering embodiments thereof, i.e. compounds according to formulas (Ia), (Ib), (Ic), (Id) or (Ie), or any of the embodiments of these compounds.

In the same way, any reference to a moiety according to a given formula also should be construed as referring to a reference to any embodiment of this formula, unless the contrary is explicitly indicated or apparent from the context.

Furthermore, a pharmaceutical composition is provided, comprising a compound of formula (I) as defined herein, and optionally at least one pharmaceutically acceptable excipient.

Another object of the present invention relates to inhibition of the PFKFB3 and/or PFKFB4 protein with the compounds of the above formula that are described herein.

Thus, in one aspect, a compound as defined herein is provided for use in the treatment of a disorder related to or mediated by the PFKFB3 protein.

The compounds of the invention may be prepared according to known methods for those skilled in the art. Other reaction schemes, as well as a variety of different solvents, temperatures and other reaction conditions, could be readily devised by those skilled in the art.

The benzothiophene sulfonyl chlorides were synthesized according to Scheme 1 as described in by Plé et al. (Plé et al., (1988) J. Heterocyclic Chem. 25, 1271-1272). Alkylation of substituted thiophenols with chloroacetone, followed by PPA-mediated cyclization of the ketones gave 5- and 7-substituted 3-methylbenzothiophenes. The preparation of the sulfonyl chlorides were performed either by a two step procedure ($SO_3$/dioxane complex or $H_2SO_4$/$Ac_2O$ followed by $POCl_3$, $POCl_3$/$PCl_5$ or $SOCl_2$) or with chlorosulfonic acid. Regarding the handling and use of $SO_3$/dioxane-complex see Paquette, *Encyclopedia of Reagents for Organic Synthesis* and references therein.

Scheme 1

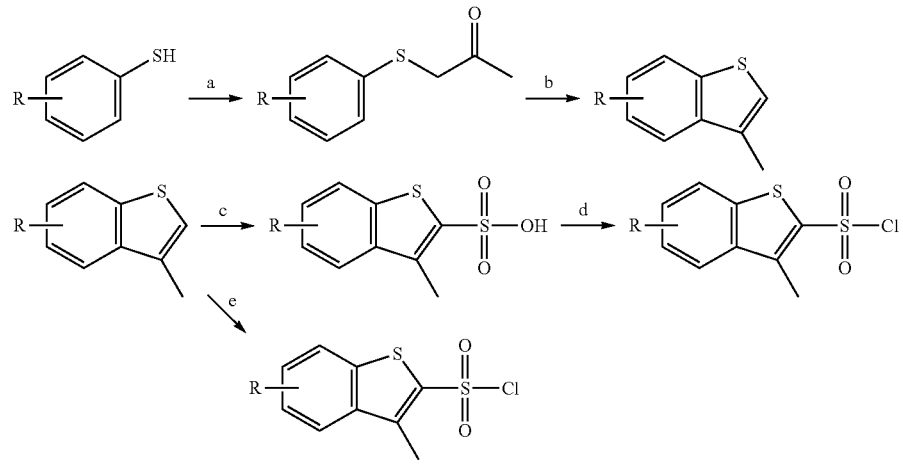

In another aspect, a compound as defined herein is provided, for use in the treatment of a disorder related to or mediated by the PFKFB4 protein.

In one aspect, a compound as defined herein is provided, for use in the treatment of cancer, inflammation or an inflammatory disorder.

The use of a compound as defined herein in the manufacturing of a medicament for the treatment of cancer, inflammation or an inflammatory disorder also is provided.

Finally, one object of the invention is to provide a method for the treatment of cancer, inflammation or an inflammatory disorder in a mammal in need of such treatment by administering to said mammal a compound as defined herein.

The invention will now be further illustrated by the following non-limiting Examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. The necessary starting materials for preparing the compounds of formula I are either known or may be prepared, by a person skilled in the art, in analogy with the preparation of known compounds. All references and publications cited herein are hereby incorporated by reference in their entirety.

a) Chloroacetone, $K_2CO_3$ or $NaHCO_3$, acetone, reflux b) polyphosphoric acid, chlorobenzene, reflux c) $SO_3$/dioxane-complex, 1,2-dichloroethane, room temperature or $H_2SO_4$/$Ac_2O$, EtOAc, room temperature d) $POCl_3$/$CH_2Cl_2$, 60° C. or $SOCl_2$, DMF, e) Chlorosulfonic acid, $CHCl_3$, 0° C.

Substituted benzofuranes were synthesized from the corresponding phenols in three steps according to Scheme 2 (Xie et al., (2004) Tetrahedron Lett. 45, 6235-6237). Iodination of the phenols with N-iodosuccinimide followed by allylation with allylbromide gave 1-allyloxy-2-iodo-benzenes as intermediates, which were transformed to the substituted benzofuranes by palladium mediated Heck couplings. The corresponding sulfonyl chlorides were thereafter prepared with $H_2SO_4$/$Ac_2O$ in EtOAc according to the sulfonylation reactions described in Scheme 1 (Graham et al., (1990) J. Med. Chem. 33, 749-754).

Scheme 2

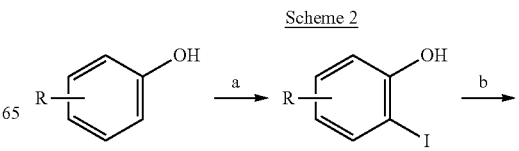

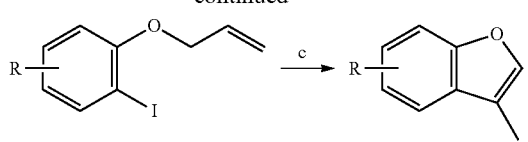

a) N-iodosuccinimide, p-TsOH, CH₂Cl₂, room temperature over night. b) allylbromide, K₂CO₃, THF, reflux, 24 h. c) NBu₃, ammoniumformate, PdCl₂, 1-butyl-3-methylimidazo-lium-tetrafluoroborate, 60° C. over night.

Sulfonyl chlorides of aryl-substituted thiophenes were prepared via palladium-mediated Suzuki couplings followed by sulfonylations using chlorosulfonic acid (Scheme 3).

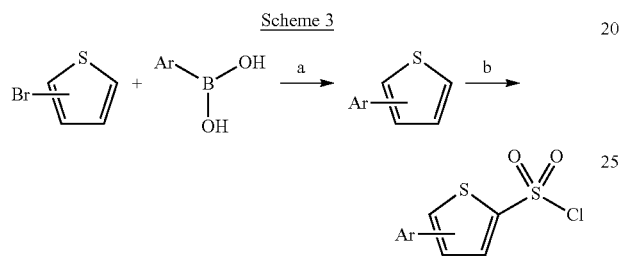

a) DIPEA, Pd(dppf)Cl₂:CH₂Cl₂, aq. dioxane 80° C. over night. b) Chlorosulfonic acid, CHCl₃, 0° C.

The starting material for the compounds described in Examples 12 and 119 (cf. below), 5-(3-amino-phenyl)-tetra-zol-2-yl]-acetic acid, was synthesised according to Scheme 4 (Kothari et al., (1980) J. Heterocyclic Chem. 17, 1393-1398).

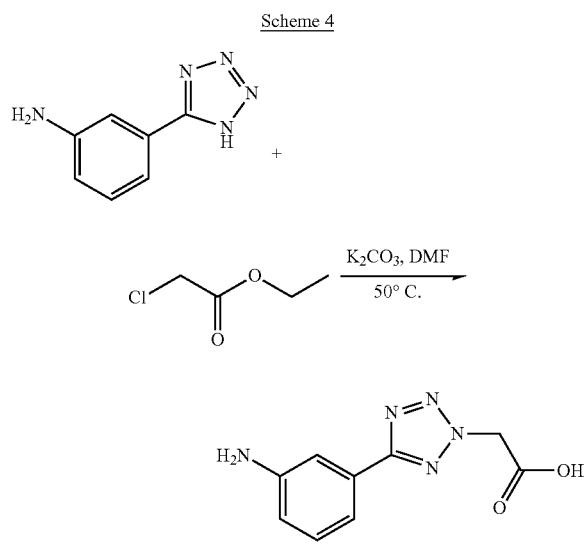

The sulfonamides were, for example, synthesised from sulfonyl chlorides and anilines/heteroaromatic amines according to any of the methods illustrated in Scheme 5, wherein L corresponds to the L-ring of a compound according to formula (I) and A=S, O or CR'=CR'.

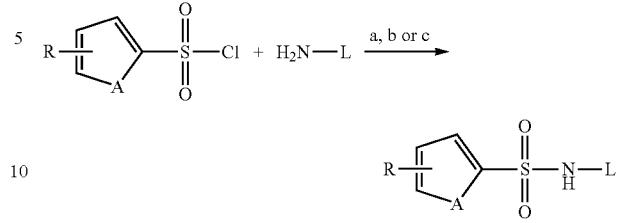

a) Pyridine, CH₂Cl₂, temperature ranging from room temperature to 60° C.
b) aq. dioxane, room temperature c) pyridine, MeCN, temperature ranging from room temperature to 60° C.

For some of examples described below, the targeted acids were obtained by alkaline hydrolysis (Scheme 6) of the intermediate esters.

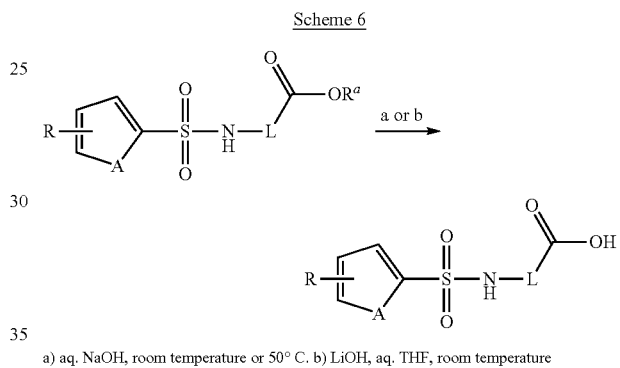

a) aq. NaOH, room temperature or 50° C. b) LiOH, aq. THF, room temperature

For some of the examples described below, the ester functionality was introduced by reacting the corresponding acids with a coupling reagent (1,1'-carbonyldiimidazole) followed by the appropriate alcohol. Alternatively, the desired ester was obtained by transesterification using the corresponding methyl ester as starting material (Scheme 7).

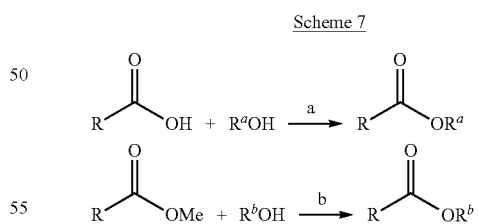

a) 1,1'-carbonyldiimidazole, pyridine, MeCN, room temperature or 50° C.
b) NaH, THF, 60° C.

The biaryl compounds (wherein A is S or CR'=CR') were prepared by Suzuki couplings at 80° C. according to modifications of the procedures described by Jiang et al. (Jiang et al., (2006) Tetrahedron Lett. 47, 197-200) (Scheme 8, steps d or e). The same synthetic procedures should be applicable for biaryl compounds with A=O.

Scheme 8

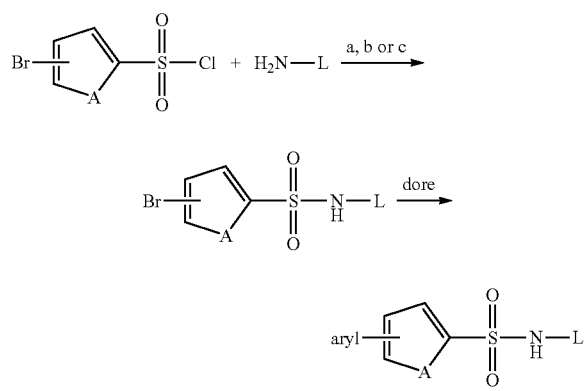

a) Pyridine, CH₂Cl₂, temperature ranging from room temperature to 60° C.
b) aq. dioxane, room temperature c) pyridine, MeCN, temperature ranging from room temperature to 60° C. d) Aryl boronic acid, NaHCO₃ (aq), Pd(PPh₃)₄, aq. EtOH, 80° C. over night e) Aryl boronic acid, DIPEA, Pd(dppf)Cl₂:CH₂Cl₂, aq. dioxane 80° C. over night. A═S or CR═CR.

Amine substituted benzothiophene analogues were synthesized from the corresponding bromides following the procedures described by Huang et. Al. (Huang et al., (2001) Org. Lett 3, 21, 3417-3419) (Scheme 9). For the aniline analogues, LiHMDS was used as a nitrogen equivalent and the free anilines were obtained by hydrolysis.

Scheme 9

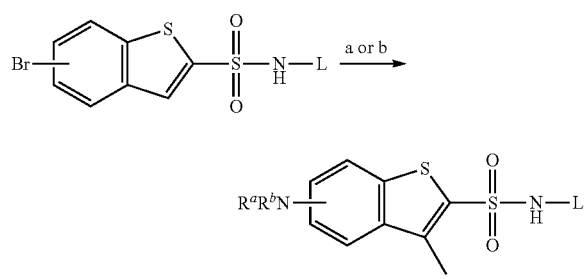

a) Amine or LiHMDS, Pd₂(dba)₃, 2-dicyclohexyl-phosphino-2'-(N,N-dimethylamino)biphenyl), LiHMDS, THF, 130° C. in a micro wave reactor
b) Amine, Pd(OAc)₂, 2-(di-ᵗbutylphosphino)biphenyl, Cs₂CO₃, dioxane, 110° C. over night.

EXAMPLES

Preparative HPLC/MS was performed on a Waters/Micromass Platform ZQ system and preparative HPLC/UV was performed on a Gilson system in accordance to the experimental details specified in the examples. Analytical HPLC/MS was performed using an Agilent 1100/1200 Series Liquid Chromatograph/Mass Selective Detector (MSD) (Single Quadrupole) (1946A/1946C/1956C/6110) equipped with an electrospray interface. GC-MS was performed on a Hewlett-Packard 5890/6890 gas chromatograph equipped with a HP-5MS cross-linked 5% PhMe Siloxane column (30 m×0.25 mm×0.25 μm film thickness) with a Hewlett-Packard 5971A/5972A mass selective detector using EI. Preparative flash chromatography was performed on Merck silica gel 60 (230-400 mesh). The compounds were named using ACD Name 6.0 or ISIS Draw 2.4. Microwave reactions were performed with a Personal Chemistry Smith Creator or Optimizer using 0.5-2 mL or 2-5 mL Smith Process Vials fitted with aluminum caps and septa. Accurate masses were measured using an Agilent MSD-TOF connected to an Agilent 1100 HPLC system. During the analyses the calibration was checked by two masses and automatically corrected when needed. Spectra were acquired in positive electrospray mode. The acquired mass range was m/z 100-1100. Profile detection of the mass peaks was used. NMR spectra were recorded on four different instruments, a Varian Inova 500 instrument equipped with a 5 mm triple resonance probe, a Varian Inova 400 instrument equipped with a 5 mm four nucleus probe, a Bruker DRX400 equipped with a 5 mm four nucleus probe and a Bruker DRX500 equipped with a 4 mm two nucleus flow-probe.

Intermediate 1

5-Isopropyl-3-methylbenzothiophene

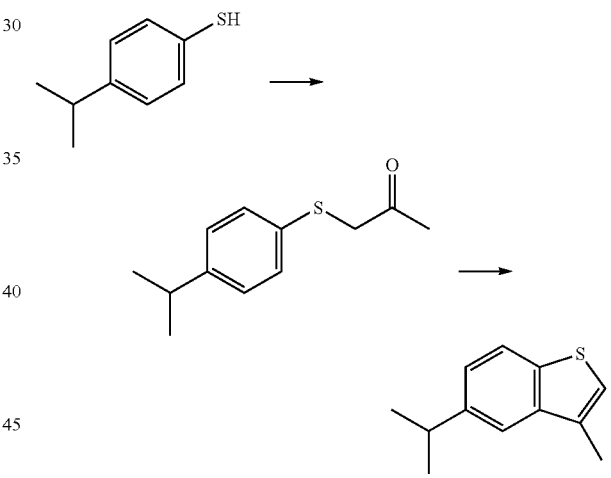

A mixture of 4-isopropyl-thiophenol (5.0 g, 32.8 mmol), chloroacetone (7.0 mL, 88 mmol) and K₂CO₃ (6.4 g, 46.3 mmol) in acetone (100 mL) was refluxed over night. More K₂CO₃ (2 g, 14.5 mmol) and chloroacetone (3.5 mL, 43 mmol) were added and the reaction mixture was heated for another 5 h. The reaction mixture was filtered and the solvent was evaporated. The crude product was mixed with polyphosphoric acid (15 g) and chlorobenzene (100 mL) and the reaction mixture was heated at reflux for 5 h. (Plé et al., (1988) J. Heterocyclic Chem. 25, 1271-1272). The reaction mixture was diluted with CH₂Cl₂ and washed with water. The combined organic phases were dried and the solvent was evaporated. The crude product was purified on silica using heptane as eluent, giving 4.2 g of the title compound as a colourless oil (67% over two steps). ¹H NMR (400 MHz, CDCl₃) δ ppm 1.37 (d, 6 H) 2.47 (d, 3 H) 3.02-3.16 (m, 1 H) 7.08 (s, 1 H) 7.27-7.30 (m, 1 H) 7.58 (d, 1 H) 7.80 (d, 1 H).

Intermediate 2

5-Isopropyl-3-methylbenzothiophene-2-sulfonyl chloride

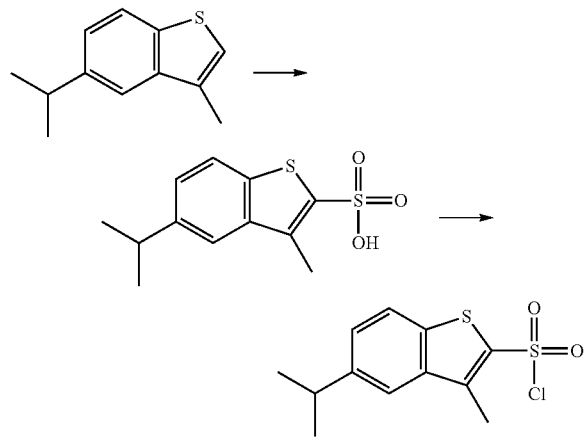

A solution of sulfur trioxide (580 mg, 7.24 mmol) in 1,2-dichloroethane (10 mL) was cooled on ice and dioxane (610 µL, 7.15 mmol) in 1,2-dichloroethane (1 mL) was added dropwise. The resulting white mixture was stirred 30 min at 0° C. A solution of 5-isopropyl-3-methylbenzothiophene (420 g, 2.2 mmol) (Intermediate 1) in 1,2-dichloroethane (4 mL) was added and the resulting dark purple mixture was stirred at room temperature for 1 h. The mixture was poured on ice and extracted with EtOAc. The acid crystallized spontaneously in the organic phase and 265 mg (44%) of 5-isopropyl-3-methylbenzothiophene-2-sulfonic acid were collected. $^1$H NMR (400 MHz, MeOH-$d_4$) δ ppm 1.32 (d, J=6.90 Hz, 6 H) 2.64 (s, 3 H) 3.05 (spt, J=6.90 Hz, 1 H) 7.32 (ddd, J=8.34, 1.70, 0.44 Hz, 1 H) 7.61 (dt, J=1.70, 0.70 Hz, 1 H) 7.72 (dd, J=8.34, 0.70 Hz, 1 H).

A mixture of 5-isopropyl-3-methylbenzothiophene-2-sulfonic acid (2.54 g, 9.4 mmol), POCl$_3$ (10 mL) and PCl$_5$ (4.0 g, 19.2 mmol) in CH$_2$Cl$_2$ (100 mL) was stirred at room temperature for 2 h. The reaction was quenched by addition of ice and water and stirred for 1 h. The organic phase was separated and dried. 1.74 g sulfonyl chloride was obtained as an oil after evaporation of the solvents. The crude product was purified on silica using CH$_2$Cl$_2$ as eluent giving 1.46 g (54%) of the title compound.

Intermediate 3

7-Methoxy-3-methylbenzothiophene

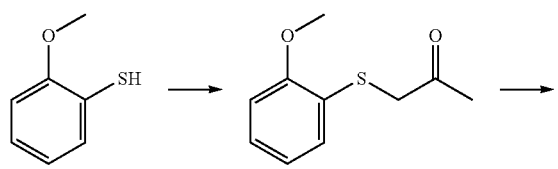

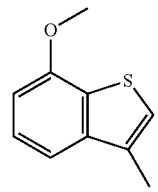

A mixture of 2-methoxythiophenol (915 mg, 6.5 mmol), chloroacetone (1.1 mL, 13.8 mmol) and K$_2$CO$_3$ (1.8 g, 13 mmol) in acetone (15 mL) was refluxed for 2 h. The mixture was filtered and the solvent evaporated. The crude product was dissolved in chlorobenzene (30 mL) and polyphosphoric acid (PPA, 0.5 g) was added (Plé et al., (1988) J. Heterocyclic Chem. 25, 1271-1272). The resulting mixture was heated at 100° C. over night, and then refluxed for 5 h. The solvent was decanted from the PPA-residue. The residue was then treated with CH$_2$Cl$_2$ and the combined organic extracts were washed with water and dried before the solvents were evaporated. The crude product was purified on silica using heptane as eluent, to give the title compound (620 mg, 53% yield over two steps). $^1$H NMR (400 MHz, CDCl$_3$) δ ppm 2.43 (d, J=1.13 Hz, 3 H) 4.01 (s, 3 H) 6.77-6.83 (m, 1 H) 7.06 (qd, J=1.17, 0.53 Hz, 1 H) 7.32-7.39 (m, 2 H).

Intermediate 4

7-Methoxy-3-methylbenzothiophene-2-sulfonyl chloride

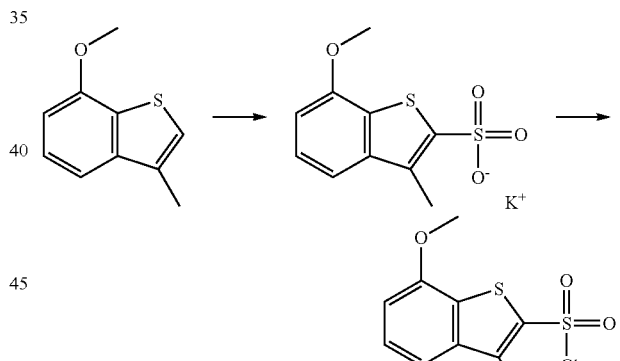

A solution of 7-methoxy-3-methylbenzothiophene (365 mg, 2.0 mmol) (Intermediate 3), Ac$_2$O (900 µL, 9.45 mmol) and conc. H$_2$SO$_4$ (170 µL) in EtOAc (5 mL) was shaken for 9 h at room temperature, then diluted with more EtOAc. The product was precipitated with KOAc (300 mg in EtOH, 5 mL). The solid was collected and dried giving 0.62 g of potassium 7-methoxy-3-methylbenzothiophene-2-sulfonate (100%). $^1$H NMR (400 MHz, DMSO-$d_6$) δ ppm 2.46 (s, 3 H) 3.93 (s, 3 H) 6.93 (dd, J=7.03, 1.51 Hz, 1 H) 7.31 (dd, J=8.03, 1.51 Hz, 1 H) 7.34 (dd, J=8.03, 7.03 Hz, 1 H).

A mixture of potassium 7-methoxy-3-methylbenzothiophene-2-sulfonate (100 mg, 0.34 mmol) in POCl$_3$ (5 mL) was heated at 60° C. over night. The POCl$_3$ was evaporated and the crude product was purified on a small amount of silica eluting with CH$_2$Cl$_2$ to give the title compound in 46% yield (43 mg).

Intermediate 5

7-Chloro-3-methylbenzothiophene

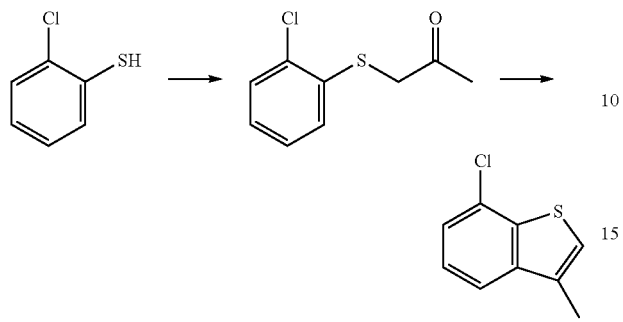

A mixture of 2-chlorothiophenol (750 μL, 6.6 mmol), chloroacetone (1.1 mL, 13.8 mmol) and $K_2CO_3$ (1.8 g, 13 mmol) in acetone (15 mL) was refluxed for 2 h. The mixture was filtered and the solvent evaporated. The crude product was dissolved in chlorobenzene (30 mL) and polyphosphoric acid (PPA, 0.5 g) was added. The resulting mixture was refluxed over night (Plé et al., (1988) J. Heterocyclic Chem. 25, 1271-1272). Additional PPA (0.5 g) was added and the reaction mixture was refluxed for another 7 h. The solvent was decanted from the PPA-residue, the residue was treated with $CH_2Cl_2$ and the combined organic extracts were washed with water and dried, and then the solvents were removed by evaporation. The crude product was purified on silica using heptane as eluent, to give the title compound (770 mg, 64% over two steps). $^1$H NMR (400 MHz, $CDCl_3$) δ ppm 2.44 (d, J=1.20 Hz, 3 H) 7.14 (q, J=1.20 Hz, 1 H) 7.32-7.38 (m, 2 H) 7.60-7.65 (m, 1 H)

Intermediate 6

7-Chloro-3-methylbenzothiophene-2-sulfonyl chloride

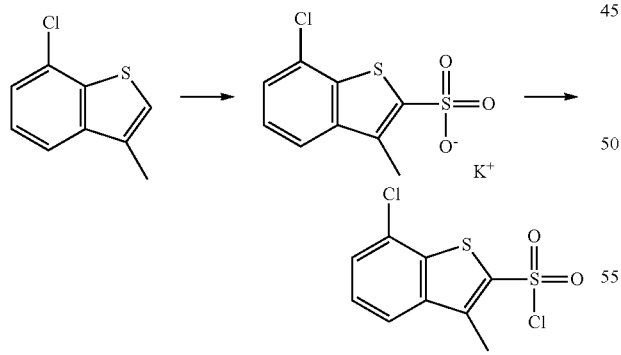

A solution of 7-chloro-3-methylbenzothiophene (Intermediate 5) (360 mg, 2.0 mmol), $Ac_2O$ (600 μL, 6.3 mmol) and conc. $H_2SO_4$ (115 μL) in EtOAc (5 mL) was shaken for 4 h at room temperature, then diluted with more EtOAc and washed with a small amount of water. The aqueous phase was extracted several times with EtOAc and the combined organic phases were dried and evaporated. The crude product was dissolved in EtOAc (50 mL) and the product was precipitated with KOAc (200 mg in EtOH, 3 mL). Since only small amounts of precipitate was formed a second portion of KOAc (200 mg in EtOH, 3 mL) was added, followed by $Et_2O$ (100 mL). The potassium 7-chloro-3-methylbenzothiophene-2-sulfonate was collected and dried in vacuum (0.76 g). $^1$H NMR (400 MHz, DMSO-$d_6$) δ ppm 2.50 (s, 3 H) 7.43 (t, J=7.78 Hz, 1 H) 7.48 (dd, J=7.78, 1.13 Hz, 1 H) 7.73 (dd, J=7.78, 1.13 Hz, 1 H).

A mixture of potassium 7-chloro-3-methylbenzothiophene-2-sulfonate (100 mg, 0.34 mmol) in $POCl_3$ (5 mL) was heated at 60° C. over night. The $POCl_3$ was evaporated and the crude product was purified on a small amount of silica using $CH_2Cl_2$ as eluent to give 58 mg of the title compound (61%).

Intermediate 7

5-Methoxy-3-methylbenzothiophene

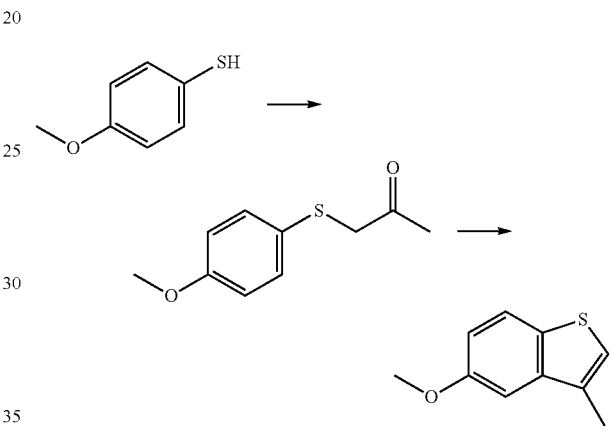

A mixture of 4-methoxythiophenol (2.8 g, 20 mmol), $K_2CO_3$ (5.5 g, 40 mmol) and chloroacetone (6.6 mL, 82 mmol) in acetone (50 mL) was heated at reflux over night. The reaction mixture was filtered and the solvent was evaporated giving 5.0 g crude product. The intermediate thioether was dissolved in chlorobenzene (50 mL) and polyphosphoric acid (PPA, 0.5 g) was added (Plé et al., (1988) J. Heterocyclic Chem. 25, 1271-1272). The reaction mixture was refluxed over night. The solvent was decanted and the PPA residue was treated with $CH_2Cl_2$. The combined organic extracts were washed with water and dried before the solvents were evaporated. The crude product was purified on silica using heptane as eluent to give the title compound (0.96 g, 27% over two steps). $^1$H NMR (400 MHz, $CDCl_3$) δ ppm 2.44 (d, J=1.20 Hz, 3 H) 3.93 (s, 3 H) 7.03 (ddd, J=8.78, 2.51, 0.50 Hz, 1 H) 7.11 (dq, J=1.20, 0.50 Hz, 1 H) 7.17 (d, J=2.51 Hz, 1 H) 7.73 (dd, J=8.78, 0.50 Hz, 1 H).

Intermediate 8

5-Methoxy-3-methylbenzothiophene-2-sulfonyl chloride

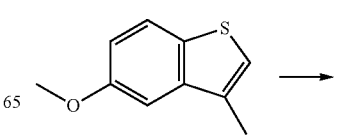

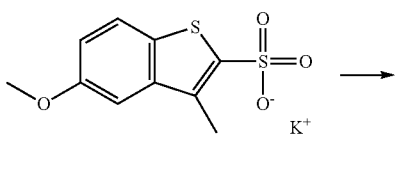

A solution of 5-methoxy-3-methylbenzothiophene (Intermediate 7) (360 mg, 2.0 mmol), Ac$_2$O (600 μL, 6.3 mmol) and conc. H$_2$SO$_4$ (115 μL) in EtOAc (5 mL) was shaken for 4 h at room temperature and then diluted with EtOAc. The potassium salt of the product was precipitated by addition of KOAc (196 mg) in EtOH (3 mL). The solid was collected and dried giving 0.47 g of potassium 5-methoxy-3-methylbenzothiophene-2-sulfonate (80%). $^1$H NMR (400 MHz, DMSO-d$_6$) δ ppm 2.46 (s, 3 H) 3.83 (s, 3 H) 6.99 (dd, J=8.78, 2.51 Hz, 1 H) 7.17 (dd, J=2.51, 0.50 Hz, 1 H) 7.72 (dd, J=8.78, 0.50 Hz, 1 H).

A mixture of potassium 5-methoxy-3-methylbenzothiophene-2-sulfonate (100 mg, 0.34 mmol) in POCl$_3$ (5 mL) was heated at 60° C. over night. The POCl$_3$ was evaporated and the remaining crude product was purified on a small amount of silica using CH$_2$Cl$_2$ as eluent to give 80 mg of the title compound (90%).

Intermediate 9

5-Bromo-3-methylbenzothiophene

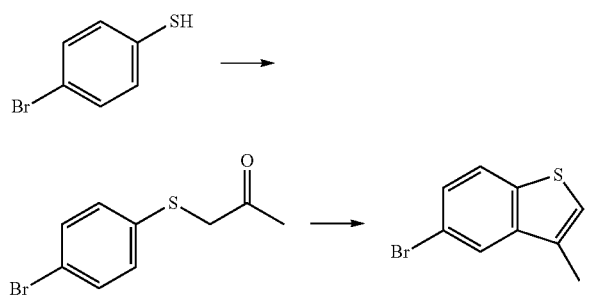

A mixture of 4-bromothiophenol (3.9 g, 20 mmol), K$_2$CO$_3$ (5.5 g, 40 mmol) and chloroacetone (6.6 mL, 82 mmol) in acetone (50 mL) was heated at reflux over night. The reaction mixture was filtered and the solvent was evaporated giving 5.0 g crude product. The intermediate thioether was dissolved in chlorobenzene (50 mL) and polyphosphoric acid (PPA, 2.5 g) was added (Plé et al., (1988) J. Heterocyclic Chem. 25, 1271-1272). After reflux for 24 h, the solvent was decanted and the PPA residue was treated with CH$_2$Cl$_2$. The combined organic extracts were washed with water and dried. Evaporation of the solvents afforded the crude product which was purified on silica (heptane as eluent) to give the title compound (2.36 g, 50% over two steps). $^1$H NMR (400 MHz, CDCl$_3$) δ ppm 2.41 (d, J=1.20 Hz, 3 H) 7.11 (qd, J=1.20, 0.54 Hz, 1 H) 7.44 (ddd, J=8.53, 1.90, 0.54 Hz, 1 H) 7.70 (dd, J=8.53, 0.54 Hz, 1 H) 7.85 (dd, J=1.90, 0.54 Hz, 1 H).

Intermediate 10

5-Bromo-3-methyl-benzothiophene-2-sulfonyl chloride

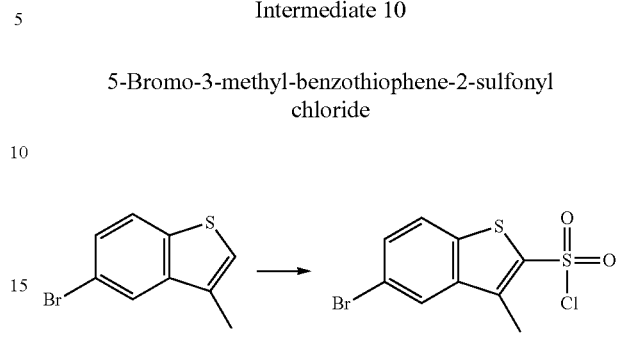

Chlorosulfonic acid (2.20 ml, 0.033 mmol) was added dropwise at −5° C. to a solution of 5-bromo-3-methylbenzothiophene (Intermediate 9) (3.0 g, 13.2 mmol) in CHCl$_3$ (30 mL). The reaction mixture was stirred at 0° C. for 3 h, and then poured into a mixture of ice/NaHCO$_3$ and stirred vigorously for 5 min. The organic phase was immediately separated, dried and concentrated to give the title compound (1.70 g, 39%).

Intermediate 11

3-Methylbenzothiophene-2-sulfonyl chloride

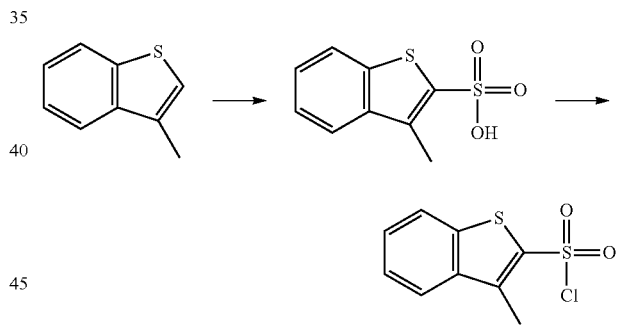

A solution of 3-methyl-benzothiophene (900 mg, 6.1 mmol), Ac$_2$O (1.75 mL, 18.5 mmol) and conc. H$_2$SO$_4$ (350 μL, 6.2 mmol) in EtOAc (5 mL) was stirred at room temperature for 3 h. The reaction mixture was diluted with EtOAc. The organic phase was washed with water and brine and then dried. Upon evaporation of some of the solvent the product precipitated. Et$_2$O was added, and the precipitate was collected giving 193 mg of 3-methylbenzothiophene-2-sulfonic acid (14%). $^1$H NMR (400 MHz, DMSO-d$_6$) δ ppm 2.48 (s, 3 H) 7.33-7.41 (m, 2 H) 7.69-7.75 (m, 1 H) 7.83-7.88 (m, 1 H).

The 3-methylbenzothiophene-2-sulfonic acid (45 mg, 0.20 mmol) was mixed with POCl$_3$ (2 mL, 20 mmol) and CH$_2$Cl$_2$ (2 mL) and heated at 70° C. for 6 h. The reaction mixture was diluted with CH$_2$Cl$_2$ before the reaction was quenched with ice and stirred at room temperature for 1 h. The organic phase was separated. Evaporation of the solvents afforded 57 mg the title compound (91%).

Intermediate 12

3,5-Dimethylbenzothiophene

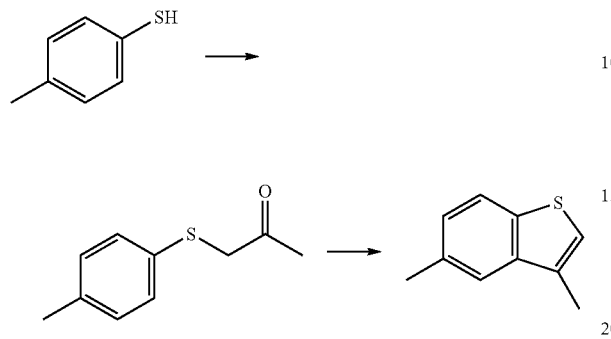

Chloroacetone (11.6 g, 125 mmol) and NaHCO$_3$ (12.6 g, 150 mmol) were added to a solution of 4-methylthiophenol (10 g, 80.5 mmol) in dry DMF (50 mL). The mixture was stirred at 50-60° C. for 1 h. The cooled reaction mixture was poured into water (200 mL) and extracted with EtOAc (2×50 mL). The combined organic extracts were dried with K$_2$CO$_3$, evaporated to dryness and the residue was distilled (b.p. 145-148° C./12 mm) to give 11.7 g of 1-(p-tolyl sulfanyl)propan-2-one (81%).

A solution of 10 mL of polyphosphoric acid (PPA) in chlorobenzene (200 mL) was heated to reflux. To this solution 1-(p-tolylsulfanyl)-propan-2-one 5.0 g (20.3 mmol) was added in portions within 20 minutes. The resulting mixture was refluxed for 18 h and then cooled to room temperature. The organic phase was separated and concentrated under reduced pressure. The oily residue was purified by flash chromatography on silica gel (90:10 hexane/EtOAc) to give 3.72 g (81%) the title compound.

Intermediate 13

3,5-Dimethyl-benzothiophene-2-sulfonyl chloride

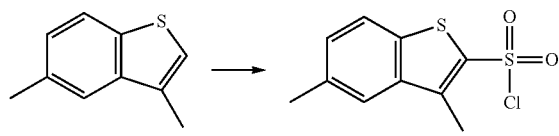

To a solution of 3,5-dimethylbenzothiophene (Intermediate 12) (5.0 g, 33.8 mmol) in CHCl$_3$ (70 mL), chlorosulfonic acid (5.6 mL, 85 mmol) was added dropwise at −5° C. The reaction mixture was stirred at 0° C. for 3 h before it was poured into a mixture of ice and NaHCO$_3$ and stirred vigorously for 5 min. The organic phase was immediately separated, dried with MgSO$_4$ and concentrated yielding 3.5 g (40%) of the title compound.

Intermediate 14

5-Fluoro-3-methyl-benzothiophene-2-sulfonyl chloride

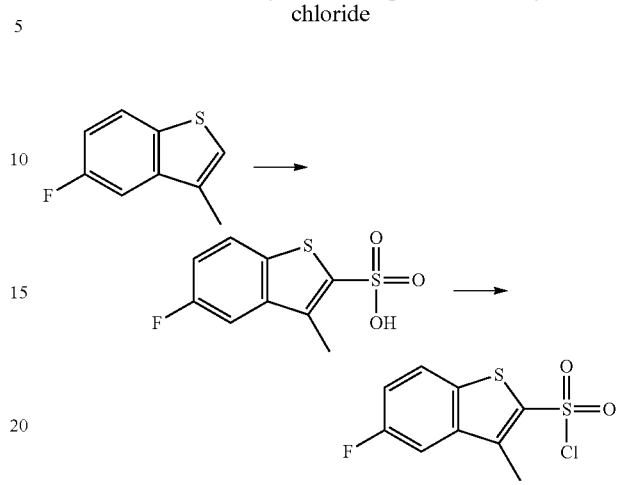

A solution of 5-fluoro-3-methyl-1-benzothiophene (1000 mg, 6.02 mmol), Ac$_2$O (1.75 mL, 18.5 mmol) and conc. H$_2$SO$_4$ (350 µL, 6.2 mmol) in EtOAc (5 mL) was shaken at room temperature for 3 h. The reaction mixture was diluted with EtOAc, washed with water and brine and then dried. Upon addition of Et$_2$O the product crystallized (120 mg). A second crop of product was obtained by evaporation of the mother liquid (0.71 g). The 5-fluoro-3-methylbenzothiophene-2-sulfonic acid was obtained in 55% total yield (0.83 g). $^1$H NMR (400 MHz, DMSO-d$_6$) δ ppm 2.45 (s, 3 H) 7.22 (ddd, J=9.09, 8.78, 2.60 Hz, 1 H) 7.52 (ddd, J=10.16, 2.60, 0.50 Hz, 1 H) 7.89 (ddd, J=8.78, 5.10, 0.50 Hz, 1 H).

A mixture of 5-fluoro-3-methylbenzothiophene-2-sulfonic acid (230 mg, 0.93 mmol) in POCl$_3$ (5 mL) was heated at 60° C. over night. The POCl$_3$ was evaporated and the crude product was dissolved in CH$_2$Cl$_2$ and washed with water. The organic phase was dried and evaporated to give 0.23 g (93%) of the title compound.

Intermediate 15

5-Isopropyl-3-methylbenzofuran

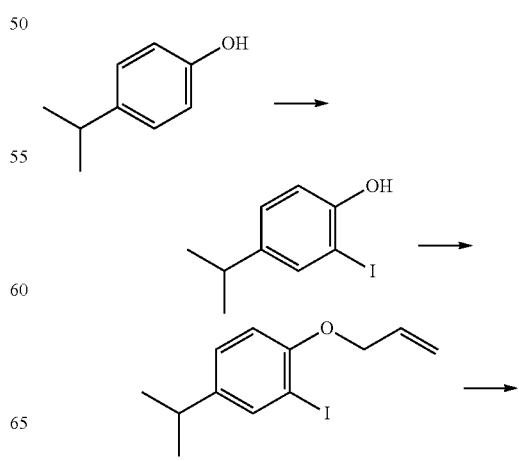

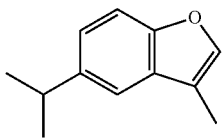

A solution of 4-isopropylphenol (500 mg, 3.67 mmol), N-iodosuccinimide (838 mg, 3.72 mmol) and p-TsOH (70 mg, 0.37 mmol) in CH$_2$Cl$_2$ (25 mL) was stirred at room temperature overnight. The reaction mixture was diluted with CH$_2$Cl$_2$ and washed with water. The organic phase was dried and evaporated to give 820 mg of 2-iodo-4-isopropylphenol (85%). $^1$H NMR (400 MHz, CDCl$_3$) δ ppm 1.22 (d, J=7.03 Hz, 6 H) 2.82 (spt, J=6.95, 6.65 Hz, 1 H) 6.92 (d, J=8.53 Hz, 1 H) 7.11 (dd, J=8.28, 2.01 Hz, 1 H) 7.50 (d, J=2.01 Hz, 1 H).

A mixture of 2-iodo-4-isopropylphenol (820 mg, 3.13 mmol), allylbromide (800 µL, 9.46 mmol) and K$_2$CO$_3$ (530 mg, 3.83 mmol) in THF (40 mL) was refluxed for 24 h and then stirred at room temperature for 48 h. The reaction mixture was diluted with CH$_2$Cl$_2$. The organic phase was washed with water followed by aq. NaHCO$_3$ (sat) and then dried. Evaporation of the solvent gave allyl-2-iodo-4-isopropylphenyl ether (892 mg) which was used without further purification. MS (ESI+) m/z 303 [M+H]$^+$.

According to the method described by Xie et al. (Xie et al., (2004) Tetrahedron Lett. 45, 6235-6237) a mixture of allyl-2-iodo-4-isopropylphenyl ether (300 mg, 0.99 mmol), NBu$_3$ (350 µL, 1.49 mmol), ammonium formate (65 mg, 1.03 mmol) and PdCl$_2$ (10 mg, 0.06 mmol) in 1-butyl-3-methylimidazolium-tetrafluoroborate (1.5 mL) was heated at 60° C. for 2 days. A second portion of PdCl$_2$ (24 mg) was added and the mixture was heated at 60° C. additional 5 h. The reaction mixture was extracted with Et$_2$O. Evaporation of the solvent afforded 220 mg crude product, which was purified on silica giving the title compound in 30% yield (55 mg). $^1$H NMR (400 MHz, CDCl$_3$) δ ppm 1.31 (d, J=6.90 Hz, 6 H) 2.24 (d, J=1.25 Hz, 3 H) 3.03 (spt, J=6.90 Hz, 1 H) 7.17 (dd, J=8.34, 1.94 Hz, 1 H) 7.34-7.39 (m, 3 H).

Intermediate 16

5-Isopropyl-3-methylbenzofuran-2-sulfonyl chloride

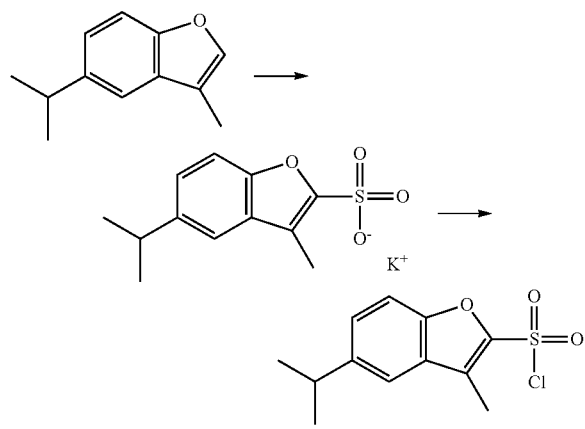

Crude 5-isopropyl-3-methylbenzofuran (Intermediate 15) (8.7 g, 50 mmol) was dissolved in EtOAc (100 mL) and Ac$_2$O (14 mL, 148 mmol) was added. Conc H$_2$SO$_4$ (3 mL, 53 mmol) was added dropwise. The mixture was stirred at room temperature for 1 h. The product was precipitated by the dropwise addition of KOAc (5.0 g) in EtOH (50 mL) and separated by centrifugation. The solvent was decanted giving 5.02 g of potassium 5-isopropyl-3-methylbenzofuran-2-sulfonate (39%). $^1$H NMR (400 MHz, DMSO-d$_6$) δ ppm 1.25 (d, J=7.03 Hz, 6 H) 2.33 (s, 3 H) 3.00 (spt, J=7.03 Hz, 1 H) 7.21 (dd, J=8.66, 1.38 Hz, 1 H) 7.36-7.41 (m, 2 H). The NMR spectra showed 2.7 equiv of EtOH in the crystals.

The potassium salt of 5-isopropyl-3-methylbenzofuran-2-sulfonic acid (100 mg, 0.34 mmol) was mixed with POCl$_3$ (5 mL) and the reaction mixture was heated at 60° C. over night. The POCl$_3$ was evaporated and the crude product was dissolved in CH$_2$Cl$_2$ and passed through a small amount of silica to give the title compound (30 mg, 33%).

Intermediate 17

5-Bromo-N-[3-(1H-tetrazol-5-yl)phenyl]thiophene-2-sulfonamide

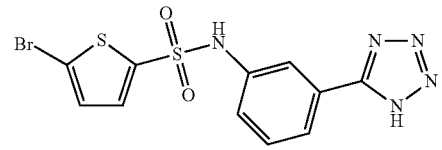 [SMILES: O=S(=O)(Nc1cccc(-c2nnn[nH]2)c1)c1ccc(Br)s1]

A solution of 5-(3-aminophenyl)tetrazole (8.1 mg, 0.05 mmol), 5-bromothiophene-2-sulfonyl chloride (14 mg, 0.055 mmol) and pyridine (12 µL, 0.015 mmol) in CH$_2$Cl$_2$ (200 µL) was stirred at room temperature over night. The title compound was obtained after purification by preparative HPLC (16.7 mg, 43%). MS (ESI+) m/z 386 [M+H]$^+$. The procedure was repeated on a larger scale with a modified purification method (flash chromatography, 10% MeOH in CH$_2$Cl$_2$), giving enough of the title compound to be used as starting material for further derivatisations.

Intermediate 18

Ethyl 3-{[(5-bromo-3-methyl-1-benzothiophen-2-yl)sulfonyl]amino}benzoate

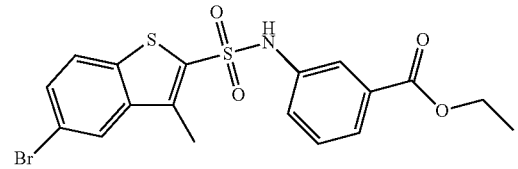 [SMILES: CCOC(=O)c1cccc(NS(=O)(=O)c2sc3ccc(Br)cc3c2C)c1]

A solution of 5-bromo-3-methyl-benzothiophene-2-sulfonyl chloride (Intermediate 10) (1.00 g, 3.26 mmol), ethyl 3-aminobenzoate (550 mg, 3.33.mmol) and pyridine (3 mL) in CH$_2$Cl$_2$ (150 mL) was stirred at room temperature overnight. The reaction was diluted with CH$_2$Cl$_2$, washed with water and aqueous HCl, dried and concentrated. The residue was purified on silica, using CH$_2$Cl$_2$ as eluent, resulting in 532 mg (36%) of the title compound. $^1$H NMR (400 MHz, CDCl$_3$) δ ppm 1.34 (t, J=7.09 Hz, 3 H) 2.44 (s, 3 H) 4.34 (q, J=7.09 Hz, 2 H) 6.85 (s, 1H) 7.36 (dd, J=8.03, 7.62 Hz, 1 H) 7.43 (ddd, J=8.03, 2.26, 1.25 Hz, 1 H) 7.57 (dd, J=8.66, 1.88 Hz, 1 H) 7.65 (dd, J=8.66, 0.50 Hz, 1 H) 7.72 (dd, J=2.26, 1.63

Hz, 1 H) 7.84 (ddd, J=7.62, 1.63, 1.25 Hz, 1 H) 7.87 (dd, J=1.88, 0.50 Hz, 1 H). MS (ESI+) m/z 454 [M+H]⁺.

Intermediate 19

3-{[(5-Chloro-3-methyl-1-benzothien-2-yl)sulfonyl]amino}benzoic acid

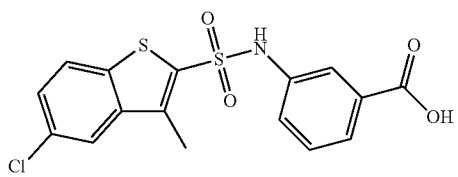 [SMILES: Cc1c(S(=O)(=O)Nc2cccc(C(=O)O)c2)sc2ccc(Cl)cc12]

Pyridine (200 μL, 2.48 mmol) was added to a solution of methyl 3-aminobenzoate (188 mg, 1.24 mmol) and 5-chloro-3-methyl-benzothiophene-2-sulfonyl chloride (349 mg, 1.24 mmol) in MeCN (10 mL). The reaction mixture was stirred at room temperature over night. After removal of the solvents, the residue was dissolved in EtOAc and water. The phases were separated, and the organic solution was washed with 1M HCl twice, water twice and brine then dried (MgSO₄). The crude product, obtained after evaporation of the solvents, was crystallized from MeOH (ca 5 mL). The solid product was triturated using heptane, giving the intermediate methyl 3-{[(5-chloro-3-methyl-1-benzothien-2-yl)sulfonyl]amino}benzoate as an off-white solid (432 mg, 88%). ¹H NMR (500 MHz, CDCl₃) δ ppm 2.46 (s, 3 H) 2.45 (s, 3 H) 6.91 (s, 1 H) 7.37 (t, J=7.81 Hz, 1 H) 7.43-7.47 (m, 2 H) 7.72 (d, J=1.96 Hz, 1 H) 7.72 (d, J=8.76 Hz, 1 H) 7.76 (t, J=1.83 Hz, 1 H) 7.85 (dt, J=7.81, 1.34 Hz, 1 H). MS (ESI+) 396 m/z [M+H]⁺.

1.7 M aq. KOH (5 mL) was added to a slurry of methyl 3-{[(5-chloro-3-methyl-1-benzothien-2-yl)sulfonyl]amino}benzoate (400 mg, 1.01 mmol) in MeOH (5 mL). The reaction mixture was stirred at 50° C. for 1.5 h. After removal of the MeOH under reduced pressure, the remaining aqueous solution was acidified to pH 3 by addition of ortho-phosphoric acid. The precipitate was collected, washed with water and dried giving the title compound as an off-white solid (363 mg, 91%). ¹H NMR (500 MHz, MeOH-d₄) δ ppm 2.49 (s, 3 H) 7.32-7.39 (m, 2 H) 7.46 (dd, J=8.67, 2.08 Hz, 1 H) 7.75 (dt, J=7.32, 1.59 Hz, 1 H) 7.82-7.86 (m, 3 H). MS (ESI+) m/z 399 [M+NH₄]⁺.

Intermediate 20

5-Chloro-4-(2,5-difluorophenyl)thiophene-2-sulfonyl chloride

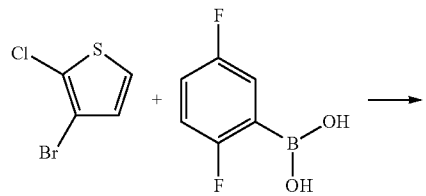

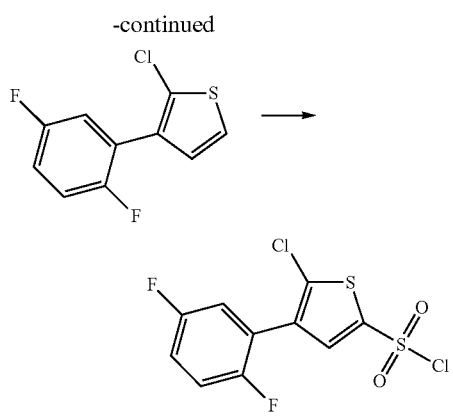

A solution of 3-bromo-2-chlorothiophene (2.43 g, 12.3 mmol), 2,5-difluorophenylboronic acid (2.91 g, 18.4 mmol), diisopropylethylamine (4.8 g, 37 mmol) and [1,1'-bis(diphenylphosphino)ferrocene]dichloropalladium(II), complex with dichloromethane (300 mg, 0.37 mmol) was stirred in dioxane (100 mL) and water (10 mL) at 80° C. for two days. Toluene (100 mL) was added. The organic phase was washed with 1 M NaOH (aq.), 1 M HCl (aq.) and brine, dried and concentrated to a brown oil. The brown oil was purified by distillation (twice) in a Kugelrohr apparatus at 120° C. and ~10 mbar resulting in 0.73 g (26%) of the intermediate 2-chloro-3-(2,5-difluorophenyl)thiophene. ¹H NMR (500 MHz, CDCl₃) δ ppm 7.01-7.23 (m, 5H).

To a solution of 2-chloro-3-(2,5-difluorophenyl)thiophene (0.73 g, 3.2 mmol) in CH₂Cl₂ (100 mL), cooled on ice, chlorosulfonic acid (0.37 g, 3.2 mmol) in CH₂Cl₂ (50 mL) was added dropwise over 1 h. The reaction was refluxed over night. The reaction mixture was cooled and washed with water (2×100 mL) and brine, dried over MgSO₄, filtered and concentrated to a dark brown oil. The oil was dissolved in heptane (50 mL) and stored in the fridge over the weekend. A black tar precipitated. The solution was decanted and concentrated to give the title compound as a light brown oil (0.87 g, 21% over two steps). MS (ESI+) m/z 293 [M−Cl]⁺.

Intermediate 21

5-(3,5-Difluorophenyl)thiophene-2-sulfonyl chloride

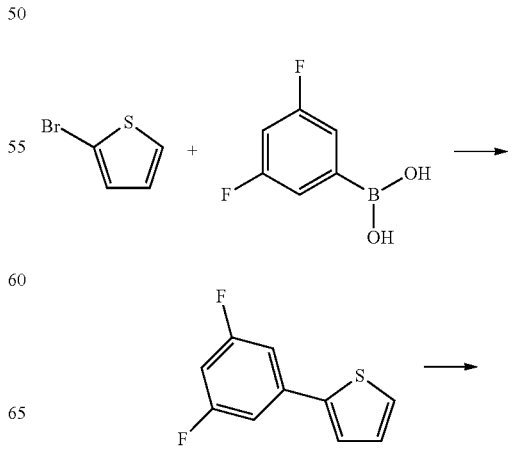

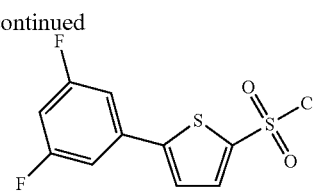

A mixture of 2-bromothiophene (2.00 g, 12.3 mmol), 3,5-difluorobenzeneboronic acid (1.94 g, 12.3 mmol), bis(triphenylphosphine)palladium chloride (0.17 g, 0.24 mmol) and dipotassium hydrogen phosphate (6.43 g, 36.9 mmol) was stirred in aqueous EtOH (1:1, 150 mL) at reflux over night. Water and EtOAc were added. After separation of the phases, the organic phase was washed with NaHCO$_3$ (aq.) and brine, dried over MgSO$_4$, filtered and concentrated to a brown semisolid. The residue was distilled in a Kugelrohr apparatus at 140° C. and ~10 mbar yielding 2.1 g (87%) of the intermediate 2-(3,5-difluorophenyl)thiophene. $^1$H NMR (500 MHz, CDCl$_3$) δ ppm 6.70-6.76 (m, 1 H) 7.10 (dd, J=5.13, 3.66 Hz, 1 H) 7.12-7.14 (m, 2 H) 7.32-7.36 (m, 2 H).

A solution of 2-(3,5-difluorophenyl)thiophene (2.1 g, 10.7 mmol) in CHCl$_3$ (50 mL) was cooled on ice and chlorosulfonic acid (3.7 g, 32.1 mmol) was added dropwise. After 10 min all material had been converted to the intermediate sulfonic acid. The reaction was stirred at 35° C. over night giving complete conversion to the sulfonyl chloride in about 80% purity. The reaction mixture was cooled to −20° C. in the freezer and then quenched with a spoon of ice. Water (100 mL) and brine (100 mL) were added. The organic phase was washed with 100 mL of brine, dried over MgSO$_4$, filtered and concentrated to a white solid. The solid was slurried in hexane (20 mL), stirred for 30 min and collected by filtration. The title compound was obtained in 41% yield (1.3 g). $^1$H NMR (500 MHz, CDCl$_3$) δ ppm 6.89-6.95 (m, 1 H) 7.15-7.18 (m, 2 H) 7.34 (d, J=4.15 Hz, 1 H) 7.87 (d, J=3.91 Hz, 1 H).

Intermediate 22

3-{[(4-Bromo-5-chlorothiophen-2-yl)sulfonyl]amino}-2-hydroxybenzoic acid

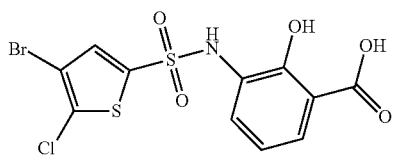 [SMILES: O=C(O)c1cccc(NS(=O)(=O)c2cc(Br)c(Cl)s2)c1O]

A solution of 3-aminosalicylic acid (0.17 g, 1.11 mmol) and 3-bromo-2-chlorothiophene-5-sulfonyl chloride (0.33 g, 1.11 mmol) in aqueous dioxane (20 mL, 95:5 dioxane/water) was stirred at room temperature for 4 weeks. The pH of the reaction mixture was adjusted to about 9 using 1M Na$_2$CO$_3$ and then EtOAc (200 mL) and water (100 mL) were added. The organic phase was removed and the aqueous phase washed with more EtOAc. The pH of the aqueous phase was adjusted to about 3 with concentrated phosphoric acid and EtOAc (200 mL) was added. The aqueous phase was removed and the organic phase was washed with 1 M HCl and brine, dried over MgSO$_4$, filtered and concentrated. The brown residue was recrystallized from aqueous MeOH at 60° C. The precipitate was collected by filtration and dried over night. The title compound was obtained in 53% yield (0.24 g). $^1$H NMR (500 MHz, MeOH-d$_4$) δ ppm 6.92 (t, J=7.93 Hz, 1 H) 7.34 (s, 1 H) 7.65 (dd, J=7.93, 1.59 Hz, 1 H) 7.75 (dd, J=7.93, 1.59 Hz, 1 H). MS (ESI+) m/z 412 [M+H]$^+$.

Example 1, General Procedure 1

2,3,4-Trichloro-N-[3-(1H-tetrazol-5-yl)phenyl]benzenesulfonamide

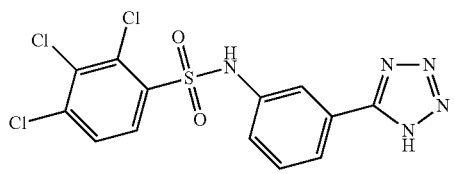 [SMILES: O=S(=O)(Nc1cccc(-c2nnn[nH]2)c1)c1ccc(Cl)c(Cl)c1Cl]

A solution of 2,3,4-trichlorobenzenesulfonyl chloride (15 mg, 0.055 mmol), 5-(3-aminophenyl)tetrazole (8 mg, 0.05 mmol) and dry pyridine (12 μL) in CH$_2$Cl$_2$ (200 μL) was stirred at room temperature over night. The solvent was evaporated and the crude product was purified by preparative HPLC (ACE C8, 5 μm 21×50 mm, flow 25 ml/min, 50 mM NH$_4$OAc in water/CH$_3$CN) to give 13 mg (65%) of the title compound. MS (ESI+) calcd for C$_{13}$H$_8$Cl$_3$N$_5$O$_2$S 402.946428, found 402.946188.

Example 2

5-(1,3-Oxazol-5-yl)-N-[3-(1H-tetrazol-5-yl)phenyl]thiophene-2-sulfonamide

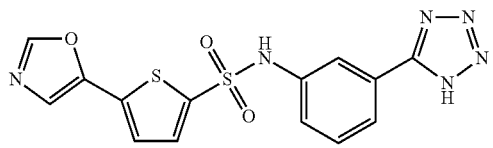 [SMILES: O=S(=O)(Nc1cccc(-c2nnn[nH]2)c1)c1ccc(-c2cnco2)s1]

The product was prepared according to General Procedure 1, described in Example 1, starting with 5-(1,3-oxazol-5-yl)thiophene-2-sulfonyl chloride (13.7 mg, 0.055 mmol) and 5-(3-amino-phenyl)tetrazole (8 mg, 0.05 mmol) yielding 9.7 mg (52%) of the title compound. MS (ESI+) calcd for C$_{14}$H$_{10}$N$_6$O$_3$S$_2$ 374.02558, found 374.02547.

Example 3

5-Chloro-3-methyl-N-[3-(1,3-oxazol-5-yl)phenyl]-1-benzothiophene-2-sulfonamide

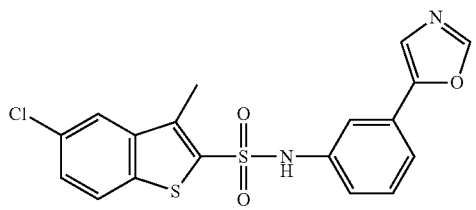 [SMILES: Cc1c(S(=O)(=O)Nc2cccc(-c3cnco3)c2)sc2ccc(Cl)cc12]

The product was prepared according to General Procedure 1, described in Example 1, starting with 5-chloro-3-methylbenzothiophene-2-sulfonyl chloride (15.5 mg, 0.055 mmol) and 3-(1,3-oxazol-5-yl)-aniline (8 mg, 0.05 mmol) yielding 5.7 mg (26%) of the title compound. $^1$H NMR (500 MHz, DMSO-$d_6$) δ ppm 7.06 (d, 1 H) 7.29 (t, 1 H) 7.39 (d, 1 H) 7.45 (br. s., 1 H) 7.49 (d, 1 H) 7.54 (s, 1 H) 7.93 (s, 1 H) 8.00 (d, 1 H) 8.36 (s, 1 H) 10.87 (br. s., 1 H) (Note; CH$_3$ in DMSO-peak).

Example 4

5-Isopropyl-3-methyl-N-[3-(1H-tetrazol-5-yl)phenyl]benzothiophene-2-sulfonamide

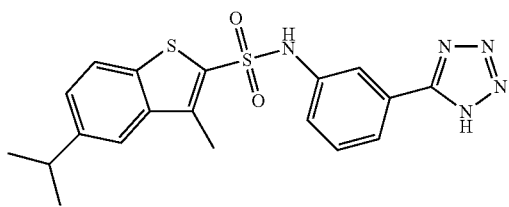

To a solution of 5-isopropyl-3-methylbenzothiophene-2-sulfonyl chloride (Intermediate 2) (746 mg, 2.5 mmol) in dry CH$_2$Cl$_2$ (10 mL) were added dry pyridine (5 mL) and 3-(1H-tetrazol-5-yl)aniline (511 mg, 2.5 mmol). The reaction mixture was stirred over night. The mixture was concentrated to dryness, the residue was treated with water (5 mL), extracted with CHCl$_3$ (2×10 mL) and the combined organic extracts were concentrated. The product was purified by flash chromatography on silica gel (eluent CHCl$_3$/MeOH 4:1) giving 290 mg (28%) of the title compound. MS (ESI+) calcd for C$_{19}$H$_{19}$N$_5$O$_2$S$_2$ 413.098016, found 413.097776.

Example 5, General Procedure 2

3-{[(5-Isopropyl-3-methyl-1-benzothien-2-yl)sulfonyl]amino}benzoic acid

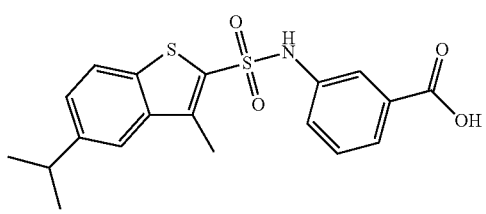 [SMILES: Cc1c(S(=O)(=O)Nc2cccc(C(=O)O)c2)sc2ccc(C(C)C)cc12]

Methyl 3-aminobenzoate (8 mg, 0.05 mmol) was dissolved in CH$_2$Cl$_2$ (100 μL) and pyridine (24 μL). A solution of 5-isopropyl-3-methylbenzothiophene-2-sulfonyl chloride (Intermediate 2) (16 mg, 0.055 mmol) in CH$_2$Cl$_2$ (100 μL) was added. The mixture was stirred at 60° C. for 4 h. The solvent was evaporated and the crude product was purified by preparative HPLC (Xterra C18, 50 mM NH$_4$HCO$_3$ (pH 10)—CH$_3$CN). The purified ester was dissolved in aqueous THF (1 mL, 1:1 THF/water) and LiOH (6 equiv.) was added. The reaction mixture was stirred at 75° C. for 3 days. The solvent was evaporated and the crude material was purified by preparative HPLC (ACE C8 5 μm, 0.1% TFA in water/CH$_3$CN) to give 5.7 mg of the title compound (30% over two steps). MS (ESI+) calcd for C$_{19}$H$_{19}$NO$_4$S$_2$ 389.0755, found 389.0741.

Example 6

2-{[(5-Isopropyl-3-methyl-1-benzothien-2-yl)sulfonyl]amino}isonicotinic acid

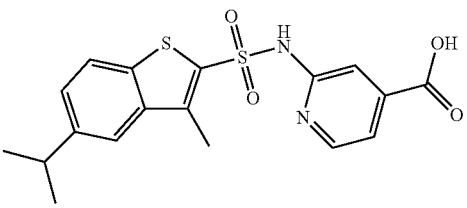 [SMILES: Cc1c(S(=O)(=O)Nc2cc(C(=O)O)ccn2)sc2ccc(C(C)C)cc12]

The product was synthesised according to General Procedure 2, described in Example 5, starting with methyl 2-aminopyridine-4-carboxylate (10.6 mg, 0.07 mmol) and 5-isopropyl-3-methylbenzothiophene-2-sulfonyl chloride (Intermediate 2) (22 mg, 0.07 mmol). The intermediate ester was hydrolyzed and the product was purified by preparative HPLC (ACE C8 5 μm, 50 mM NH$_4$OAc (pH 7) in water/CH$_3$CN) giving 0.9 mg of the title compound (3% over two steps). MS (ESI+) calcd for C$_{18}$H$_{18}$N$_2$O$_4$S$_2$ 390.0708, found 390.0703.

Example 7

2-{[(5-Isopropyl-3-methyl-1-benzothien-2-yl)sulfonyl]amino}-1,3-thiazole-5-carboxylic acid

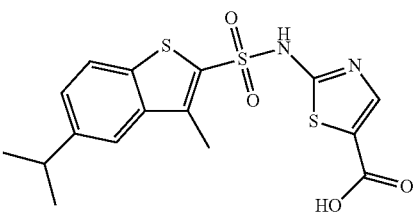 [SMILES: Cc1c(S(=O)(=O)Nc2ncc(C(=O)O)s2)sc2ccc(C(C)C)cc12]

The product was synthesised according to General Procedure 2, described in Example 5, starting with methyl 2-aminothiazole-5-carboxylate (15.1 mg, 0.1 mmol) and 5-isopropyl-3-methylbenzothiophene-2-sulfonyl chloride (Intermediate 2) (32 mg, 0.11 mmol). The intermediate ester was hydrolyzed and the product was purified by preparative HPLC (ACE C8 5 μm, 50 mM NH$_4$OAc (pH 7) in water/CH$_3$CN) giving 3.4 mg of the title compound (9% over two steps). MS (ESI+) calcd for C$_{16}$H$_{16}$N$_2$O$_4$S$_3$ 396.0272, found 396.0282.

Example 8

2-{[(5-Isopropyl-3-methyl-1-benzothien-2-yl)sulfonyl]amino}-4-methyl-1,3-thiazole-5-carboxylic acid

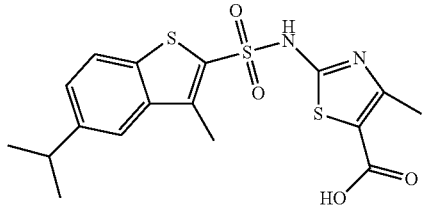 [SMILES: Cc1nc(NS(=O)(=O)c2sc3ccc(C(C)C)cc3c2C)sc1C(=O)O]

The product was synthesised according to General Procedure 2, described in Example 5, starting with 5-isopropyl-3-methylbenzothiophene-2-sulfonyl chloride (Intermediate 2) (22 mg, 0.077 mmol) and ethyl 2-amino-4-methylthiazole-5-carboxylate (13 mg, 0.07 mmol). The intermediate ester was hydrolyzed and the product was purified by preparative HPLC (ACE C8 5 µm, 50 mM NH$_4$OAc in water (pH 7)/CH$_3$CN) giving 1.2 mg of the title compound (4% over two steps). MS (ESI+) calcd for $C_{17}H_{18}N_2O_4S_3$ 410.0429, found 410.0422.

Example 9

5-{[(5-Isopropyl-3-methyl-1-benzothien-2-yl)sulfonyl]amino}nicotinic acid

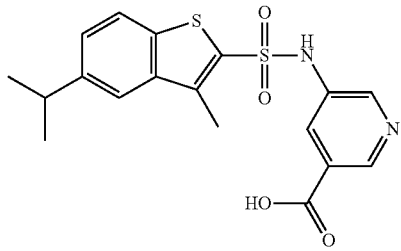 [SMILES: Cc1c(S(=O)(=O)Nc2cncc(C(=O)O)c2)sc2ccc(C(C)C)cc12]

The product was synthesised according to General Procedure 1, described in Example 1, starting from 5-isopropyl-3-methylbenzothiophene-2-sulfonyl chloride (Intermediate 2) (25 mg, 0.09 mmol) and 3-amino-5-pyridinecarboxylic acid (23 mg, 0.17 mmol). The reaction mixture was evaporated and the crude product was purified by preparative HPLC (ACE C8, 5 µm 21×50 mm, flow 25 ml/min, 50 mM NH$_4$OAc in water/CH$_3$CN) giving 1.4 mg of the title compound (4%). MS (ESI+) calcd for $C_{18}H_{18}N_2O_4S_2$ 390.0708, found 390.0707.

Example 10

6-{[(5-Isopropyl-3-methyl-1-benzothien-2-yl)sulfonyl]amino}pyridine-2-carboxylic acid

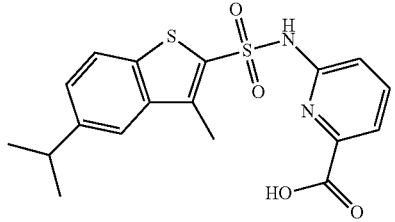 [SMILES: Cc1c(S(=O)(=O)Nc2cccc(C(=O)O)n2)sc2ccc(C(C)C)cc12]

The product was synthesised according to General Procedure 2, described in Example 5, starting from 5-isopropyl-3-methylbenzothiophene-2-sulfonyl chloride (Intermediate 2) (30 mg, 0.10 mmol) and methyl 6-aminopyridine-2-carboxylate (30 mg, 0.2 mmol) giving 23 mg crude ester. The ester was hydrolyzed and the crude product was purified by preparative HPLC (ACE C8, 5 µm, 21×50 mm, flow 25 ml/min, 50 mM NH$_4$OAc in water/CH$_3$CN) giving 11.6 mg of the title compound (30% over two steps). MS (ESI+) calcd for $C_{18}H_{18}N_2O_4S_2$ 390.070799, found 390.071449.

Example 11

3-{[(5-Isopropyl-3-methyl-1-benzothien-2-yl)sulfonyl]amino}-5-nitrobenzoic acid

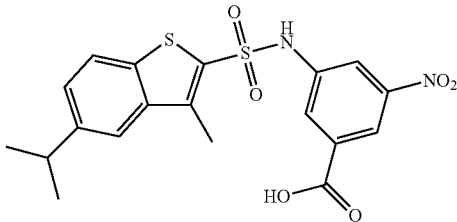 [SMILES: Cc1c(S(=O)(=O)Nc2cc(C(=O)O)cc([N+](=O)[O-])c2)sc2ccc(C(C)C)cc12]

The product was prepared according to General Procedure 1, described in Example 1, starting from 5-isopropyl-3-methylbenzothiophene-2-sulfonyl chloride (Intermediate 2) (16 mg, 0.055 mmol) and 3-amino-5-nitrobenzoic acid (9 mg, 0.05 mmol) giving 6 mg of the title compound (30%). MS (ESI+) calcd for $C_{19}H_{18}N_2O_6S_2$ 434.060628, found 434.060168.

Example 12

[5-(3-{[(5-Isopropyl-3-methyl-1-benzothien-2-yl)sulfonyl]amino}phenyl)-2H-tetrazol-2-yl]acetic acid

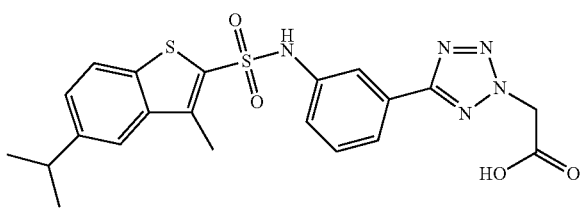 [SMILES: Cc1c(S(=O)(=O)Nc2cccc(-c3nnn(CC(=O)O)n3)c2)sc2ccc(C(C)C)cc12]

Ethyl chloroacetate (33 mL, 0.31 mmol), [3-(2H-tetrazol-5-yl)phenyl]amine (50 mg, 0.31 mmol) and K$_2$CO$_3$ (86 mg, 0.62 mmol) were mixed in dry DMF (5 mL). The mixture was heated at 50° C. for 2 h using a Stem block. The reaction mixture was partitioned between water (15 mL) and EtOAc (10 mL). The aqueous layer was extracted once with EtOAc (10 mL). The organic layers were combined, dried (Na$_2$SO$_4$), filtered and concentrated to give 60 mg of a light brown gum. The intermediate was dissolved in dry CH$_2$Cl$_2$ (3 mL) followed by addition of 5-isopropyl-3-methylbenzothiophene-2-sulfonyl chloride (Intermediate 2) (58 mg, 0.20 mmol) and pyridine (113 µL, 1.41 mmol). The reaction mixture was stirred for 2 h at room temperature. Aqueous NaOH (1M, 1 mL) was added and the reaction mixture was stirred for an additional 5 minutes. The mixture was acidified with aqueous HCl (1M, 1 mL) and partitioned between CH$_2$Cl$_2$ (10 mL) and water (10 mL). The aqueous layer was extracted once with EtOAc (10 mL). The organic layers were combined, dried (Na$_2$SO$_4$), filtered and concentrated to give the crude product (250 mg) as a brown gum. The crude product was dissolved in MeOH/DMSO (7:1, 4 mL) and purified by reversed phase preparative HPLC (ACE C8, 0.1% TFA in water/CH$_3$CN) to give 34 mg of the title compound as a light brown solid (36% over two steps). $^1$H NMR (400 MHz, MeOH-d$_4$) δ ppm 1.27 (d, 6 H) 2.53 (s, 3 H) 2.95-3.07 (m, 1 H) 5.59 (s, 2 H) 7.25-7.31 (m, 1 H) 7.33-7.40 (m, 2 H) 7.59-7.63 (m, 1 H) 7.73 (d, 1 H) 7.79-7.85 (m, 1 H) 7.94-8.00 (m, 1 H). The structure was confirmed by extended NMR analysis ($^1$H NMR, $^{13}$C NMR, gDQFCOSY, $^{13}$C-gHSQC, $^{13}$C-gHMBC, $^{15}$N-gHMBC and DPFGSE-NOE). MS (ESI+) calcd for C$_{21}$H$_{21}$N$_5$O$_4$S$_2$ 471.103496, found 471.103976.

Example 13

5-Isopropyl-3-methyl-N-[3-(1H-tetrazol-5-yl)phenyl]-1-benzofuran-2-sulfonamide

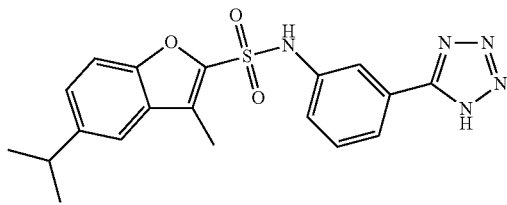

The product was prepared according to General Procedure 1, described in Example 1, starting from 5-isopropyl-3-methylbenzofuran-2-sulfonyl chloride (Intermediate 16) (24 mg, 0.09 mmol) and 5-(3-amino-phenyl)tetrazole (28 mg, 0.17 mmol) giving 7.7 mg (21%) of the title compound. MS (ESI+) calcd for C$_{19}$H$_{19}$N$_5$O$_3$S 397.12086, found 397.12046.

Example 14

3-{[(5-Isopropyl-3-methyl-1-benzofuran-2-yl)sulfonyl]amino}benzoic acid

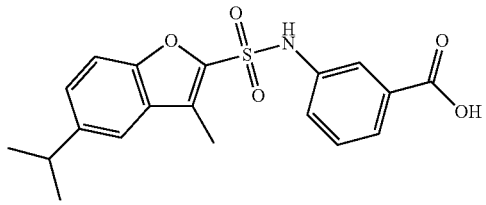 [SMILES: Cc1c(S(=O)(=O)Nc2cccc(C(=O)O)c2)oc2ccc(C(C)C)cc12]

The product was prepared according to General Procedure 1, described in Example 1, starting from 5-isopropyl-3-methylbenzofuran-2-sulfonyl chloride (Intermediate 16) (24 mg, 0.09 mmol) and 3-aminobenzoic acid (24 mg, 0.18 mmol) giving 6.3 mg (19%) of the title compound. MS (ESI+) calcd for C$_{19}$H$_{19}$NO$_5$S 373.098393, found 373.098603.

Example 15

(3-{[(5-Isopropyl-3-methyl-1-benzothien-2-yl)sulfonyl]amino}phenyl)acetic acid

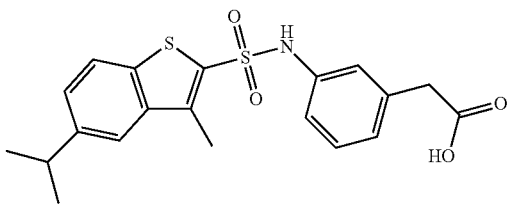 [SMILES: Cc1c(S(=O)(=O)Nc2cccc(CC(=O)O)c2)sc2ccc(C(C)C)cc12]

A solution of 5-isopropyl-3-methylbenzothiophene-2-sulfonyl chloride (Intermediate 2) (15 mg, 0.05 mmol), 3-aminophenyl acetic acid (16 mg, 0.10 mmol) and dry pyridine (100 µL) in CH$_2$Cl$_2$ (1 mL) was heated in a sealed tube at 70° C. in a Stem block. The solvent was evaporated and the crude product was purified by preparative HPLC (ACE C8, 5 µm 21×50 mm, flow 25 ml/min, 50 mM NH$_4$OAc in water/CH$_3$CN) to give 14.8 mg (73%) of the title compound. MS (ESI+) calcd for C$_{20}$H$_{21}$NO$_4$S$_2$ 403.0912, found 403.09047.

Example 16

N-[3-(1H-Tetrazol-5-yl)phenyl]biphenyl-3-sulfonamide

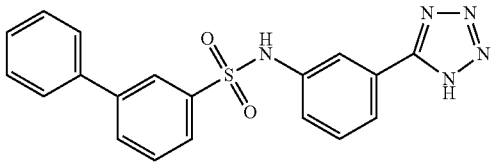 [SMILES: O=S(=O)(Nc1cccc(-c2nnn[nH]2)c1)c1cccc(-c2ccccc2)c1]

The product was prepared according to General Procedure 1, described in Example 1, starting from 3-phenylbenzenesulfonylchloride (14 mg, 0.055 mmol) and 5-(3-aminophenyl)tetrazole (8 mg, 0.05 mmol) giving 5.7 mg (30%) of the title compound. $^1$H NMR (400 MHz, MeOH-d$_4$) δ ppm 5.46-5.50 (m, 1 H) 7.24-7.43 (m, 5 H) 7.44-7.56 (m, 3 H) 7.70-7.79 (m, 4 H) 7.95-8.00 (m, 1 H). MS (ESI+) calcd for C$_{19}$H$_{15}$N$_5$O$_2$S 377.0946, found 377.0946.

Example 17

4'-Fluoro-N-[3-(1H-tetrazol-5-yl)phenyl]biphenyl-3-sulfonamide

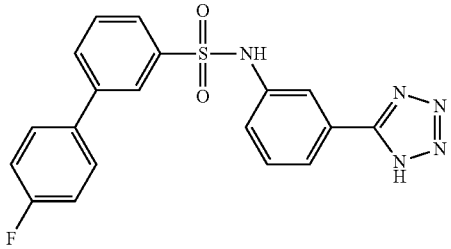 [SMILES: O=S(=O)(Nc1cccc(-c2nnn[nH]2)c1)c1cccc(-c2ccc(F)cc2)c1]

The product was prepared according to General Procedure 1, described in Example 1, starting from [3-(4-fluorophenyl)phenyl]sulfonyl chloride (15 mg, 0.055 mmol) and 5-(3-aminophenyl)tetrazole (8 mg, 0.05 mmol) giving 13 mg (66%) of the title compound. MS (ESI+) calcd for $C_{19}H_{14}FN_5O_2S$ 395.085224, found 395.085454.

Example 18

2,6-Dichloro-N-[3-(1H-tetrazol-5-yl)phenyl]-4-(trifluoromethyl)benzenesulfonamide

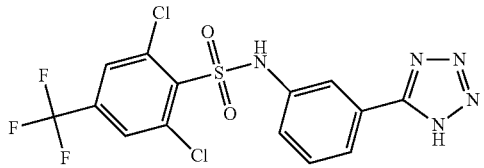 [SMILES: O=S(=O)(Nc1cccc(-c2nnn[nH]2)c1)c1c(Cl)cc(C(F)(F)F)cc1Cl]

The product was prepared according to General Procedure 1, described in Example 1, starting from 2,6-dichloro-4-(trifluoromethyl)benzenesulfonyl chloride (17 mg, 0.055 mmol) and 5-(3-aminophenyl)tetrazole (8 mg, 0.05 mmol) giving 12 mg (54%) of the title compound. MS (ESI+) calcd for $C_{14}H_8Cl_2F_3N_5O_2S$ 436.972785, found 436.973025.

Example 19

4'-Methoxy-N-[3-(1H-tetrazol-5-yl)phenyl]biphenyl-3-sulfonamide

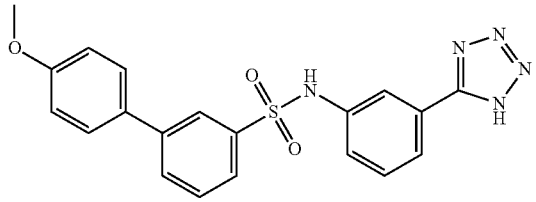 [SMILES: COc1ccc(-c2cccc(S(=O)(=O)Nc3cccc(-c4nnn[nH]4)c3)c2)cc1]

The product was prepared according to General Procedure 1, described in Example 1, starting from [3-(4-methoxyphenyl)phenyl]sulfonyl chloride (16 mg, 0.055 mmol) and 5-(3-aminophenyl)tetrazole (8 mg, 0.05 mmol) giving 12 mg (60%) of the title compound. MS (ESI+) calcd for $C_{20}H_{17}N_5O_3S$ 407.10521, found 407.10532.

Example 20

N-[3-(1H-Tetrazol-5-yl)phenyl]naphthalene-2-sulfonamide

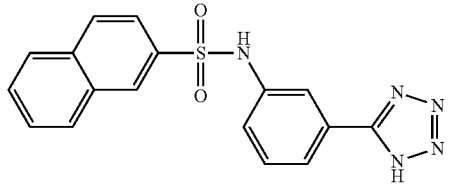 [SMILES: O=S(=O)(Nc1cccc(-c2nnn[nH]2)c1)c1ccc2ccccc2c1]

The product was prepared according to General Procedure 1, described in Example 1, starting from 2-naphthalenesulfonyl chloride (13 mg, 0.055 mmol) and 5-(3-aminophenyl) tetrazole (8 mg, 0.05 mmol) giving 10 mg (57%) of the title compound. MS (ESI+) calcd for $C_{17}H_{13}N_5O_2S$ 351.078995, found 351.080505

Example 21

5-[2-(Methylthio)pyrimidin-4-yl]-N-[3-(1H-tetrazol-5-yl)phenyl]thiophene-2-sulfonamide

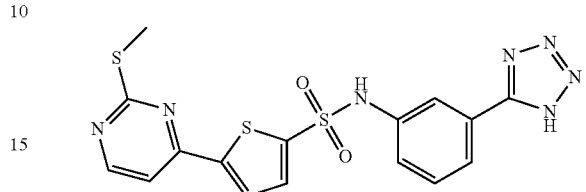

The product was prepared according to General Procedure 1, described in Example 1, starting from 5-[2-(methylthio)pyrimidin-4-yl]thiophene-2-sulfonyl chloride (17 mg, 0.055 mmol) and 5-(3-aminophenyl)tetrazole (8 mg, 0.05 mmol) giving 9.3 mg (43%) of the title compound. MS (ESI+) calcd for $C_{16}H_{13}N_7O_2S_3$ 431.029285, found 431.029205.

Example 22, General Procedure 3

5-(5-Fluoro-2-methoxyphenyl)-N-[3-(1H-tetrazol-5-yl)phenyl]thiophene-2-sulfonamide

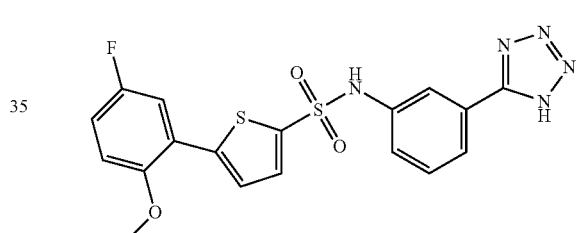

A mixture of 5-bromo-N-[3-(1H-tetrazol-5-yl)phenyl]thiophene-2-sulfonamide (Intermediate 17) (19 mg, 0.05 mmol), 5-fluoro-2-methoxyphenylboronic acid (10 mg, 0.06 mmol), Pd(PPh$_3$)$_4$ (3 mg, 0.0025 mmol), NaHCO$_3$ (13 mg, 0.15 mmol), EtOH (750 µL) and water (250 µL) was heated in a sealed tube at 80° C. over night. The mixture was concentrated and purified by preparative HPLC (ACE C8 5 µm, 0.1% TFA in water/CH$_3$CN) giving 4.1 mg (19%) of the title compound. MS (ESI+) calcd for $C_{18}H_{14}FN_5O_3S_2$ 431.052209, found 431.051439.

Example 23

5-(3,5-Difluorophenyl)-N-[3-(1H-tetrazol-5-yl)phenyl]thiophene-2-sulfonamide

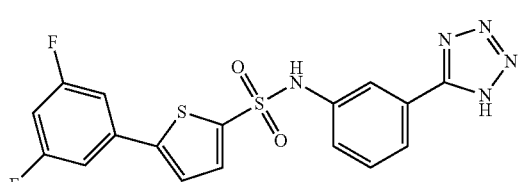

The product was prepared according to General Procedure 3, described in Example 22, starting from 5-bromo-N-[3-(1H-tetrazol-5-yl)phenyl]thiophene-2-sulfonamide (Intermediate 17) (19 mg, 0.05 mmol) and 3,5-difluorophenylboronic acid (9 mg, 0.06 mmol) giving 7.2 mg (34%) of the title compound. MS (ESI+) calcd for $C_{17}H_{11}F_2N_5O_2S_2$ 419.032222, found 419.032222.

Example 24

5-(2-Methoxyphenyl)-N-[3-(1H-tetrazol-5-yl)phenyl]thiophene-2-sulfonamide

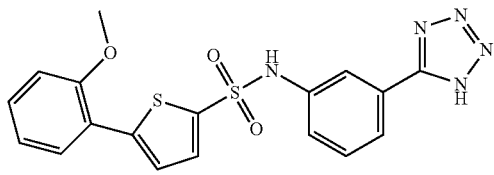 [SMILES: COc1ccccc1-c1ccc(S(=O)(=O)Nc2cccc(-c3nnn[nH]3)c2)s1]

The product was prepared according to General Procedure 3, described in Example 22, starting from 5-bromo-N-[3-(1H-tetrazol-5-yl)phenyl]thiophene-2-sulfonamide (Intermediate 17) (19 mg, 0.05 mmol) and 2-methoxyphenylboronic acid (9 mg, 0.06 mmol) giving 5.7 mg (28%) of the title compound. MS (ESI+) calcd for $C_{18}H_{15}N_5O_3S_2$ 413.061631, found 413.062971.

Example 25

5-(2-Methyl-1,3-thiazol-4-yl)-N-[3-(1H-tetrazol-5-yl)phenyl]thiophene-2-sulfonamide

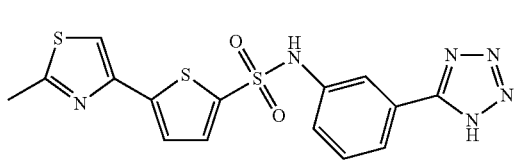 [SMILES: Cc1nc(-c2ccc(S(=O)(=O)Nc3cccc(-c4nnn[nH]4)c3)s2)cs1]

The product was prepared according to General Procedure 1, described in Example 1, starting from 5-(2-methylthiazol-4-yl)thiophene-2-sulphonylchloride (15 mg, 0.055 mmol) and [3-(1H-tetrazol-5-yl)phenyl]amine (8 mg, 0.05 mmol) giving 5.2 mg (26%) of the title compound. MS (ESI+) calcd for $C_{15}H_{12}N_6O_2S_3$ 404.0184, found 404.0182.

Example 26

5-(2-Chlorophenyl)-N-[3-(1H-tetrazol-5-yl)phenyl]thiophene-2-sulfonamide

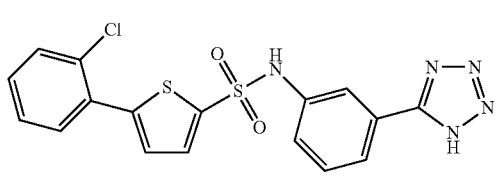 [SMILES: O=S(=O)(Nc1cccc(-c2nnn[nH]2)c1)c1ccc(-c2ccccc2Cl)s1]

The product was prepared according to General Procedure 3, described in Example 22, starting from 5-bromo-N-[3-(1H-tetrazol-5-yl)phenyl]thiophene-2-sulfonamide (Intermediate 17) (19 mg, 0.05 mmol) and 2-chlorophenylboronic acid (9 mg, 0.06 mmol) giving 3.5 mg (16%) of the title compound. MS (ESI+) calcd for $C_{17}H_{12}ClN_5O_2S_2$ 417.012094, found 417.012204.

Example 27

5-(4-Methylphenyl)-N-[3-(1H-tetrazol-5-yl)phenyl]thiophene-2-sulfonamide

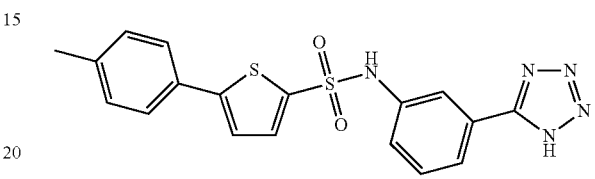

The product was prepared according to General Procedure 3, described in Example 22, starting from 5-bromo-N-[3-(1H-tetrazol-5-yl)phenyl]thiophene-2-sulfonamide (Intermediate 17) (19 mg, 0.05 mmol) and 4-methylbenzene boronic acid (8 mg, 0.06 mmol) giving 5.5 mg (28%) of the title compound. MS (ESI+) calcd for $C_{18}H_{15}N_5O_2S_2$ 397.066716, found 397.066596.

Example 28

5-(2,4-Dimethoxyphenyl)-N-[3-(1H-tetrazol-5-yl)phenyl]thiophene-2-sulfonamide

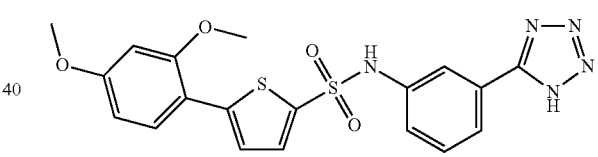

The product was prepared according to General Procedure 3, described in Example 22, starting from 5-bromo-N-[3-(1H-tetrazol-5-yl)phenyl]thiophene-2-sulfonamide (Intermediate 17) (19 mg, 0.05 mmol) and 2,4-dimethoxyphenylboronic acid (11 mg, 0.06 mmol) giving 3.5 mg (16%) of the title compound. MS (ESI+) calcd for $C_{19}H_{17}N_5O_4S_2$ 443.072195, found 443.071935.

Example 29

5-(4-Chlorophenyl)-N-[3-(1H-tetrazol-5-yl)phenyl]thiophene-2-sulfonamide

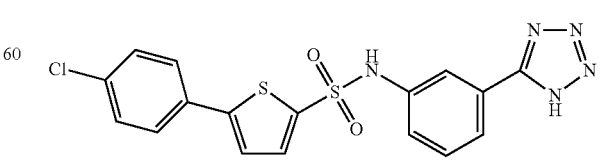

The product was prepared according to General Procedure 3, described in Example 22, starting from 5-bromo-N-[3-

(1H-tetrazol-5-yl)phenyl]thiophene-2-sulfonamide (Intermediate 17) (19 mg, 0.05 mmol) and 4-chlorophenylboronic acid (9 mg, 0.06 mmol) giving 4.4 mg (21%) of the title compound. MS (ESI+) calcd for $C_{17}H_{12}ClN_5O_2S_2$ 417.012094, found 417.013904.

Example 30

5-(4-Fluoro-2-methoxyphenyl)-N-[3-(1H-tetrazol-5-yl)phenyl]thiophene-2-sulfonamide

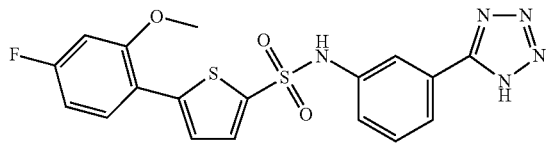 [SMILES: COc1cc(F)ccc1-c1ccc(S(=O)(=O)Nc2cccc(-c3nnn[nH]3)c2)s1]

The product was prepared according to General Procedure 3, described in Example 22, starting from 5-bromo-N-[3-(1H-tetrazol-5-yl)phenyl]thiophene-2-sulfonamide (Intermediate 17) (19 mg, 0.05 mmol) and 4-fluoro-2-methoxyphenylboronic acid (10 mg, 0.06 mmol) giving 8.3 mg (37%) of the title compound. MS (ESI+) calcd for $C_{18}H_{14}FN_5O_3S_2$ 431.052209, found 431.052249.

Example 31

N-[3-(1H-Tetrazol-5-yl)phenyl]biphenyl-4-sulfonamide

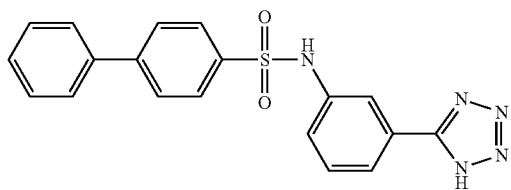 [SMILES: O=S(=O)(Nc1cccc(-c2nnn[nH]2)c1)c1ccc(-c2ccccc2)cc1]

The product was prepared according to General Procedure 1, described in Example 1, starting from biphenyl-4-sulfonyl chloride (14 mg, 0.055 mmol) and [3-(1H-tetrazol-5-yl)phenyl]amine (8 mg, 0.05 mmol) giving 11 mg (60%) of the title product. MS (ESI+) calcd for $C_{19}H_{15}N_5O_2S$ 377.094645, found 377.094375.

Example 32

5-Chloro-3-methyl-N-[3-(1H-tetrazol-5-yl)phenyl]-1-benzothiophene-2-sulfonamide

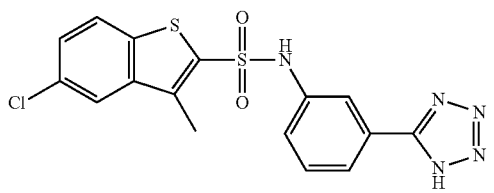 [SMILES: Cc1c(S(=O)(=O)Nc2cccc(-c3nnn[nH]3)c2)sc2ccc(Cl)cc12]

The product was prepared according to General Procedure 1, described in Example 1, starting from 5-chloro-3-methyl-benzothiophene-2-sulfonyl chloride (15 mg, 0.055 mmol) and 5-(3-aminophenyl)tetrazole (8 mg, 0.05 mmol) giving 8 mg (40%) of the title product. MS (ESI+) calcd for $C_{16}H_{12}ClN_5O_2S_2$ 405.012094, found 405.012744.

Example 33

3,5-Dimethyl-N-[3-(1H-tetrazol-5-yl)phenyl]-1-benzothiophene-2-sulfonamide

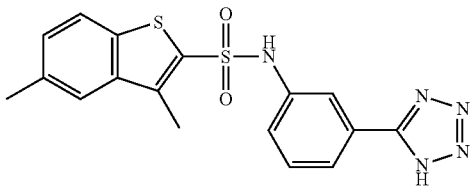 [SMILES: Cc1ccc2sc(S(=O)(=O)Nc3cccc(-c4nnn[nH]4)c3)c(C)c2c1]

To a solution of 3-(1H-tetrazol-5-yl)-phenylamine (161 mg, 10 mmol) in dry $CH_2Cl_2$ (10 mL) pyridine (0.5 mL) and 3,5-dimethyl-benzothiophene-2-sulfonyl chloride (Intermediate 13) (260 mg, 10 mmol) were added. The mixture was stirred for 4 h and then concentrated in vacuo. The product was purified by column chromatography on silica gel (eluent: 2 to 15% MeOH in $CHCl_3$) affording 104 mg (27%) of the title compound. $^1$H NMR (DMSO-$d_6$) δ ppm 2.40 (s, 3H) 2.52 (s, 3H) 7.29 (d, 1H) 7.35 (d, 1H) 7.42 (t, 1H) 7.70 (m, 2H) 7.85 (d, 1H) 7.92 (s, 1H). MS (ESI+) calcd for $C_{17}H_{15}N_5O_2S_2$ 385.066716, found 385.065826.

Example 34

5-Bromo-3-methyl-N-[3-(1H-tetrazol-5-yl)phenyl]-1-benzothiophene-2-sulfonamide

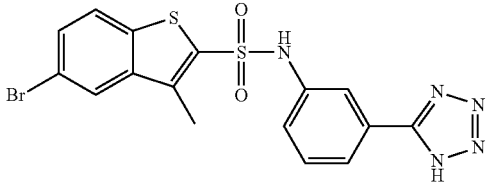 [SMILES: Cc1c(S(=O)(=O)Nc2cccc(-c3nnn[nH]3)c2)sc2ccc(Br)cc12]

The product was prepared according to General Procedure 1, described in Example 1, starting from 5-bromo-3-methyl-benzothiophene-2-sulfonyl chloride (Intermediate 10) (510 mg, 1.57 mmol) and [3-(1H-tetrazol-5-yl)phenyl]amine (230 mg, 1.4 mmol) giving 300 mg (27%) of the title compound. MS (ESI+) calcd for $C_{16}H_{12}BrN_5O_2S_2$ 448.961579, found 448.961839.

Example 35

7-Methoxy-3-methyl-N-[3-(1H-tetrazol-5-yl)phenyl]-1-benzothiophene-2-sulfonamide

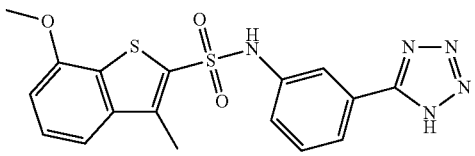 [SMILES: COc1cccc2c(C)c(S(=O)(=O)Nc3cccc(-c4nnn[nH]4)c3)sc12]

The product was prepared according to General Procedure 1, described in Example 1, starting from 7-methoxy-3-methylbenzothiophene-2-sulfonyl chloride (Intermediate 4) (23 mg, 0.09 mmol) and [3-(1H-tetrazol-5-yl)phenyl]amine (29 mg, 0.18 mmol) giving 18.7 mg (40%) of the title compound. MS (ESI+) calcd for $C_{17}H_{15}N_5O_3S_2$ 401.061631, found 401.060921.

Example 36

7-Chloro-3-methyl-N-[3-(1H-tetrazol-5-yl)phenyl]-1-benzothiophene-2-sulfonamide

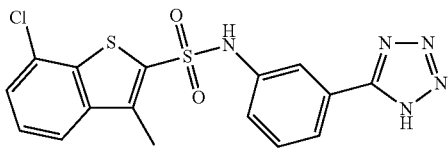 [SMILES: Cc1c(S(=O)(=O)Nc2cccc(-c3nnn[nH]3)c2)sc2c(Cl)cccc12]

The product was prepared according to General Procedure 1, described in Example 1, starting from 7-chloro-3-methyl-benzothiophene-2-sulfonyl chloride (Intermediate 6) (30 mg, 0.10 mmol) and 5-(3-amino-phenyl)tetrazole (34 mg, 0.21 mmol) giving 20.2 mg (50%) of the title compound. MS (ESI+) calcd for $C_{16}H_{12}ClN_5O_2S_2$ 405.012094, found 405.012294.

Example 37

5-Methoxy-3-methyl-N-[3-(1H-tetrazol-5-yl)phenyl]-1-benzothiophene-2-sulfonamide

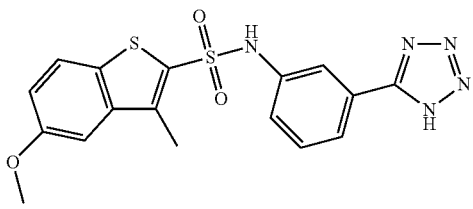 [SMILES: COc1ccc2sc(S(=O)(=O)Nc3cccc(-c4nnn[nH]4)c3)c(C)c2c1]

The product was prepared according to General Procedure 1, described in Example 1, starting from 5-methoxy-3-methylbenzothiophene-2-sulfonyl chloride (Intermediate 8) (42 mg, 0.15 mmol) and 5-(3-amino-phenyl)tetrazole (49 mg, 0.30 mmol) giving 26.6 mg (44%) of the title compound. MS (ESI+) calcd for $C_{17}H_{15}N_5O_3S_2$ 401.061631, found 401.062391.

Example 38

3-{[(5-Chloro-3-methyl-1-benzothien-2-yl)sulfonyl]amino}benzoic acid

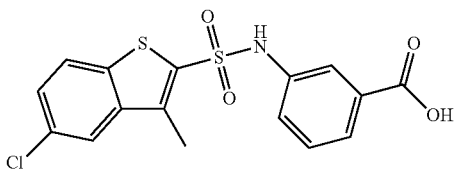 [SMILES: Cc1c(S(=O)(=O)Nc2cccc(C(=O)O)c2)sc2ccc(Cl)cc12]

A solution of 5-chloro-3-methylbenzothiophene-2-sulfonyl chloride (200 mg, 0.711 mmol) in $CH_2Cl_2$ (5 mL) was added to a mixture of methyl 3-aminobenzoate (107 mg, 0.711 mmol) and pyridine (1 mL) in $CH_2Cl_2$ (5 mL). The reaction mixture was stirred at room temperature over night. The solvent was evaporated and the crude methyl 3-{[(5-chloro-3-methyl-1-benzothien-2-yl)sulfonyl]amino}benzoate (100 mg) was slurried in water (4 mL). LiOH (300 mg) was added and the mixture was stirred at room temperature for 2 h. The reaction was acidified by aqueous 2 M HCl and the white precipitate was collected by filtration, washed with $CH_2Cl_2$ (5 mL) and dried. The title compound was obtained in 28% yield (75 mg, over two steps). MS (ESI+) calcd for $C_{16}H_{12}ClNO_4S_2$ 380.989627, found 380.989527.

Example 39

3-Methyl-N-[3-(1H-tetrazol-5-yl)phenyl]-1-benzothiophene-2-sulfonamide

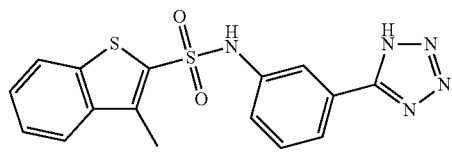 [SMILES: Cc1c(S(=O)(=O)Nc2cccc(-c3nnn[nH]3)c2)sc2ccccc12]

The product was prepared according to General Procedure 1, described in Example 1, starting from 3-methylbenzothiophene-2-sulfonyl chloride (Intermediate 11) (25 mg, 0.10 mmol) and 5-(3-amino-phenyl)tetrazole (33 mg, 0.20 mmol). The title compound was obtained in 34% yield (13.3 mg). MS (ESI+) calcd for $C_{16}H_{13}N_5O_2S_2$ 371.051066, found 371.049276.

Example 40

5-Methyl-N-[3-(1H-tetrazol-5-yl)phenyl]-1-benzothiophene-2-sulfonamide

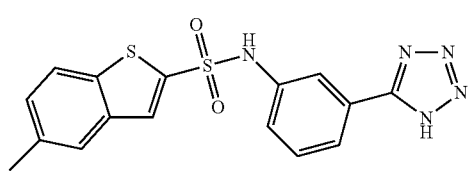 [SMILES: Cc1ccc2sc(S(=O)(=O)Nc3cccc(-c4nnn[nH]4)c3)cc2c1]

The product was prepared according to General Procedure 1, described in Example 1, starting from 5-methyl-benzothiophene-2-sulfonyl chloride (30 mg, 0.12 mmol) and 5-(3-aminophenyl)tetrazole (20 mg, 0.12 mmol) giving the title compound as a white solid (11 mg, 25%). $^1$H NMR (400 MHz, MeOH-$d_4$) δ ppm 2.40 (s, 3 H) 7.25-7.30 (m, 1 H) 7.34-7.40 (m, 1 H) 7.45 (t, J=7.91 Hz, 1 H) 7.62-7.65 (m, 1 H) 7.68-7.74 (m, 2 H) 7.78 (s, 1 H) 7.94 (t, J=1.88 Hz, 1 H). MS (ESI+) calcd for $C_{16}H_{13}N_5O_2S_2$ 371.051066, found 371.050166.

Example 41

3-{[(5-Bromo-3-methyl-1-benzothien-2-yl)sulfonyl]amino}benzoic acid

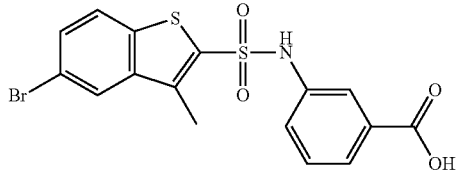 [SMILES: Cc1c(S(=O)(=O)Nc2cccc(C(=O)O)c2)sc2ccc(Br)cc12]

Ethyl 3-{[(5-bromo-3-methyl-1-benzothiophen-2-yl)sulfonyl]amino}benzoate (Intermediate 18) (42 mg, 0.093 mmol) was hydrolyzed with 1 M NaOH (1 mL) in EtOH (2 mL) at room temperature over night. The reaction mixture was acidified and extracted with EtOAc. The combined organic phases were washed with water and dried. Evaporation of the solvents gave 23 mg (58%) of the title compound. MS (ESI+) calcd for $C_{16}H_{12}BrNO_4S_2$ 424.939112, found 424.939992.

Example 42

3-{[(7-Methoxy-3-methyl-1-benzothien-2-yl)sulfonyl]amino}benzoic acid

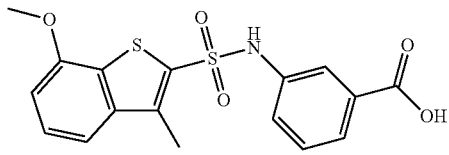 [SMILES: COc1cccc2c(C)c(S(=O)(=O)Nc3cccc(C(=O)O)c3)sc12]

The product was prepared according to General Procedure 1, described in Example 1, starting from 7-methoxy-3-methylbenzothiophene-2-sulfonyl chloride (Intermediate 4) (23 mg, 0.09 mmol) and 3-aminobenzoic acid (25 mg, 0.18 mmol) affording 18.5 mg (55%) of the title compound. MS (ESI+) calcd for $C_{17}H_{15}NO_5S_2$ 377.039164, found 377.039094

Example 43

5-Fluoro-3-methyl-N-[3-(1H-tetrazol-5-yl)phenyl]-1-benzothiophene-2-sulfonamide

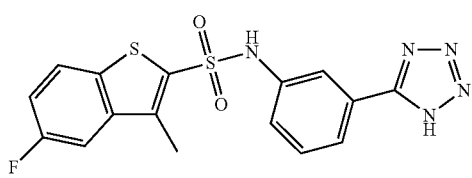 [SMILES: Cc1c(S(=O)(=O)Nc2cccc(-c3nnn[nH]3)c2)sc2ccc(F)cc12]

The product was prepared according to General Procedure 1, described in Example 1, starting from 5-fluoro-3-methylbenzothiophene-2-sulfonyl chloride (Intermediate 14) (26 mg, 0.10 mmol) and 5-(3-amino-phenyl)tetrazole (31 mg, 0.19 mmol). The title compound was obtained in 36% yield (13.9 mg). MS (ESI+) calcd for $C_{16}H_{12}FN_5O_2S_2$ 389.041644, found 389.042334.

Example 44

3-{[(7-Chloro-3-methyl-1-benzothien-2-yl)sulfonyl]amino}benzoic acid

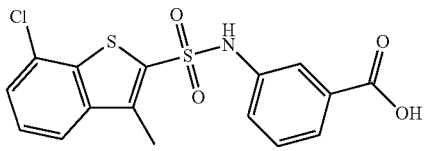 [SMILES: Cc1c(S(=O)(=O)Nc2cccc(C(=O)O)c2)sc2c(Cl)cccc12]

The product was prepared according to General Procedure 1, described in Example 1, starting from 7-chloro-3-methylbenzothiophene-2-sulfonyl chloride (Intermediate 6) (30 mg, 0.10 mmol) and 3-amino-benzoic acid (29 mg, 0.21 mmol) to afford 24 mg (63%) of the title compound. MS (ESI+) calcd for $C_{16}H_{12}ClNO_4S_2$ 380.989627, found 380.989977.

Example 45, General Procedure 4

3-Methyl-5-pyrrolidin-1-yl-N-[3-(1H-tetrazol-5-yl)phenyl]-1-benzothiophene-2-sulfonamide

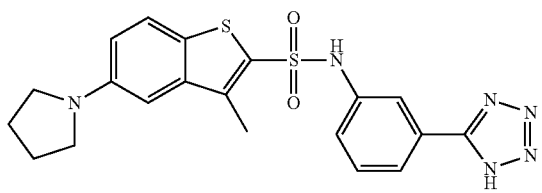 [SMILES: Cc1c(S(=O)(=O)Nc2cccc(-c3nnn[nH]3)c2)sc2ccc(N3CCCC3)cc12]

A micro-tube was charged with tris(benzylideneacetone)dipalladium $(Pd_2(dba)_3)$ (0.5 mg, 0.0005 mmol), 2-dicyclohexylphosphino-2'-(N,N-dimethylamino)biphenyl (0.5 mg, 0.0012 mmol) and pyrrolidine (9 mg, 0.12 mmol). The tube was sealed and flushed with nitrogen. LiHMDS (1M in THF, 120 µL, 0.12 mmol) and a solution of 5-bromo-3-methyl-N-[3-(1H-tetrazol-5-yl)phenyl]-1-benzothiophene-2-sulfonamide (Example 34) (45 mg, 0.1 mmol) in dry THF were added to the reaction mixture via syringes. The reaction mixture was heated in a microwave reactor at 130° C. for 1000 s. Aqueous HCl (1 M) was added and the mixture was stirred at room temperature for 5 min. The solution was then neutralized by addition of aqueous NaOH. The crude product was purified by preparative HPLC (ACE C8, 5 µm 21×50 mm, flow 25 ml/min, 50 mM $NH_4OAc$ in water/$CH_3CN$) to give 1.9 mg (4%) of the title compound. MS (ESI+) calcd for $C_{20}H_{20}N_6O_2S_2$ 440.108915, found 440.108815.

Example 46

3-{[(3-Methyl-5-pyrrolidin-1-yl-1-benzothien-2-yl)sulfonyl]amino}benzoic acid

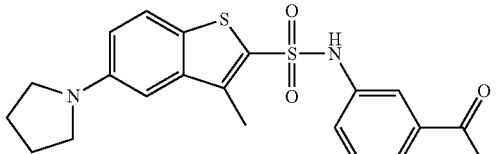

The intermediate ethyl 3-{[(3-methyl-5-pyrrolidin-1-yl-1-benzothiophen-2-yl)sulfonyl]amino}benzoate was prepared from ethyl 3-{[(5-bromo-3-methyl-1-benzothien-2-yl)sulfonyl]amino}benzoate (Intermediate 18) (45 mg, 0.1 mmol) and pyrrolidine (8 mg, 0.12 mmol) according to General Procedure 4, described in Example 45.

The ethyl 3-{[(3-methyl-5-pyrrolidin-1-yl-1-benzothiophen-2-yl)sulfonyl]amino}benzoate (4.7 mg, 0.01 mmol) was hydrolyzed with LiOH (2.6 mg, 0.06 mmol) in THF/water (1:1, 2 mL) at 55° C. over night. The reaction mixture was neutralized with acetic acid (3.6 µL) and the mixture was concentrated. The crude product was purified by preparative HPLC (ACE C8, 5 µm 21×50 mm, flow 25 ml/min, 50 mM NH$_4$OAc in water/CH$_3$CN) to give 2.7 mg (6% over two steps) of the title compound. MS (ESI+) calcd for $C_{20}H_{20}N_2O_4S_2$ 416.086449, found 416.086649.

Example 47

3-{[(5-Amino-3-methyl-1-benzothien-2-yl)sulfonyl]amino}benzoic acid

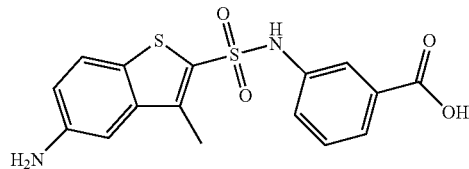 [SMILES: Cc1c(S(=O)(=O)Nc2cccc(C(=O)O)c2)sc2ccc(N)cc12]

The intermediate ethyl 3-{[(5-amino-3-methyl-1-benzothien-2-yl)sulfonyl]amino}benzoate was prepared from ethyl 3-{[(5-bromo-3-methyl-1-benzothien-2-yl)sulfonyl]amino}benzoate (Intermediate 18) (45 mg, 0.1 mmol) and LiHMDS (1M in THF, 120 µL, 0.12 mmol) according to General Procedure 4, described in Example 45, using a modified reaction time and reaction temperature (100° C., 1500 s, microwave reactor) yielding 7.3 mg of ethyl 3-{[(5-amino-3-methyl-1-benzothien-2-yl)sulfonyl]-amino}benzoate.

The ethyl 3-{[(5-amino-3-methyl-1-benzothien-2-yl)sulfonyl]-amino}benzoate was hydrolyzed with LiOH following the hydrolysis procedure described in Example 46. The title compound was obtained in 7% yield (over two steps, 2.6 mg). MS (ESI+) calcd for $C_{16}H_{14}N_2O_4S_2$ 362.039498, found 362.040938.

Example 48

5-Amino-3-methyl-N-[3-(1H-tetrazol-5-yl)phenyl]-1-benzothiophene-2-sulfonamide

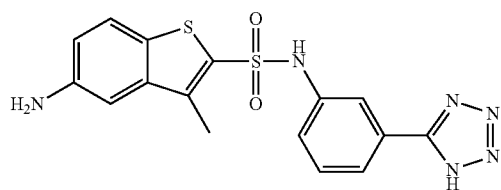 [SMILES: Cc1c(S(=O)(=O)Nc2cccc(-c3nnn[nH]3)c2)sc2ccc(N)cc12]

The product was prepared from 5-bromo-3-methyl-N-[3-(1H-tetrazol-5-yl)phenyl]-1-benzothiophene-2-sulfonamide (Example 34) (45 mg, 0.1 mmol) and LiHMDS (1M in THF, 120 µL, 0.12 mmol) according to the General Procedure 4, described in Example 45, using a modified reaction time (130° C., 300 s, microwave reactor). The title compound was obtained in 2% yield (0.6 mg). MS (ESI+) calcd for $C_{16}H_{14}N_6O_2S_2$ 386.061965, found 386.061875.

Example 49

3-({[5-(Acetylamino)-3-methyl-1-benzothien-2-yl]sulfonyl}amino)benzoic acid

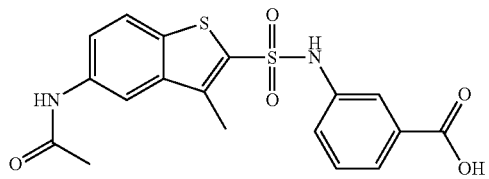 [SMILES: CC(=O)Nc1ccc2sc(S(=O)(=O)Nc3cccc(C(=O)O)c3)c(C)c2c1]

The intermediate methyl 3-{[(5-bromo-3-methyl-1-benzothiophen-2-yl)sulfonyl]amino}benzoate was prepared according to General Procedure 1, described in Example 1, starting from 5-bromo-3-methylbenzothiophene-2-sulfonyl chloride (Intermediate 10) (870 mg, 2.67 mmol) and methyl 3-aminobenzoate (367 mg, 2.43 mmol). The reaction mixture was diluted with CH$_2$Cl$_2$ (20 mL) and washed with 1M HCl (30 mL). The organic phase was dried (Na$_2$SO$_4$). Evaporation of the solvents afforded 600 mg of crude methyl-3-{[(5-bromo-3-methyl-1-benzothien-2-yl)sulfonyl]amino}benzoate, which was used without further purification.

The intermediate methyl 3-{[(5-amino-3-methyl-1-benzothien-2-yl)sulfonyl]amino}benzoate was prepared from methyl 3-{[(5-bromo-3-methyl-1-benzothien-2-yl)sulfonyl]amino}benzoate (45 mg, 0.1 mmol) and LiHMDS (1M in THF, 120 µL, 0.12 mmol) according to the General Procedure 4, described in Example 45, using a modified reaction time (130° C., 300 s, microwave reactor). The experiment was repeated four times giving 14 mg of methyl 3-{[(5-amino-3-methyl-1-benzothien-2-yl)sulfonyl]amino}benzoate.

A solution of methyl 3-{[(5-amino-3-methyl-1-benzothien-2-yl)sulfonyl]amino}benzoate (7 mg, 0.019 mmol) in CH$_2$Cl$_2$ (200 uL), acetic anhydride (5 mg, 0.022 mmol) and pyridine (11 uL) was stirred at room temperature over night. The mixture was concentrated and dissolved in THF/water (1 mL) and LiOH (1 mg, 0.024 mmol) was added. The diacetylated intermediate was hydrolyzed at room temperature for 4 h. The crude product was purified by preparative HPLC (ACE C8, 5 µm, 21×50 mm, flow 25 ml/min, 50 mM NH$_4$OAc in water/MeCN) to give 4.3 mg (56%) of the title compound. MS (ESI+) calcd for $C_{18}H_{16}N_2O_5S_2$ 404.050063, found 404.050323.

Example 50

3-(p-Tolyl)-N-[3-(1H-tetrazol-5-yl)phenyl]benzenesulfonamide

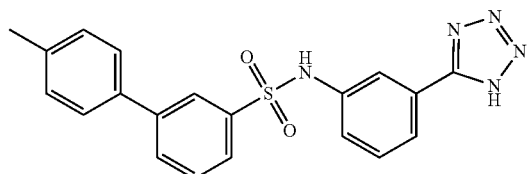

The product was prepared according to General Procedure 1, described in Example 1, starting from [3-(4-methylphenyl)phenyl sulfonyl chloride (14.7 mg, 0.055 mmol) and 5-(3-aminophenyl)tetrazole (8.0 mg, 0.05 mmol) yielding 18.3 mg (19%) of the title compound. MS (ESI+) calcd for $C_{20}H_{17}N_5O_2S$ 391.110296, found 391.110156.

Example 51

2,4-Dichloro-5-methyl-N-[3-(1H-tetrazol-5-yl)phenyl]benzenesulfonamide

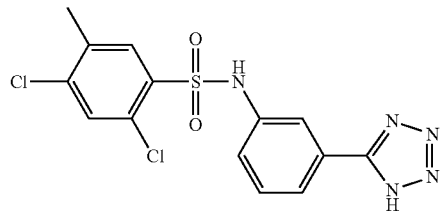 [SMILES: Cc1cc(S(=O)(=O)Nc2cccc(-c3nnn[nH]3)c2)c(Cl)cc1Cl]

The product was prepared according to General Procedure 1, described in Example 1, starting with 2,4-dichloro-5-methylbenzene sulfonyl chloride (14.3 mg, 0.055 mmol) and 5-(3-aminophenyl)tetrazole (8 mg, 0.05 mmol) yielding 4.7 mg (24%) of the title compound. MS (ESI+) calcd for $C_{14}H_{11}Cl_2N_5O_2S$ 383.001051, found 383.000871.

Example 52

3-(3,5-Dichlorophenyl)-N-[3-(1-H-tetrazol-5-yl)phenyl]benzenesulfonamide

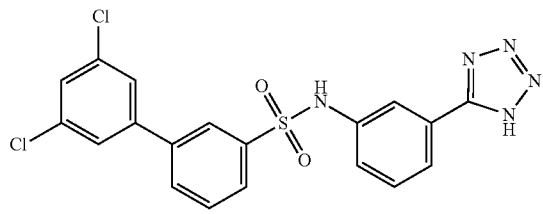 [SMILES: O=S(=O)(Nc1cccc(-c2nnn[nH]2)c1)c1cccc(-c2cc(Cl)cc(Cl)c2)c1]

The product was prepared according to General Procedure 1, described in Example 1, starting with [3-(3,5-dichlorophenyl]sulfonyl chloride (17.7 mg, 0.055 mmol) and 5-(3-aminophenyl)tetrazole (8 mg, 0.05 mmol) yielding 3.5 mg (16%) of the title compound. MS (ESI+) calcd for $C_{19}H_{13}Cl_2N_5O_2S$ 445.016701, found 445.016501.

Example 53

2,4-Dichloro-6-methyl-N-[3-(1H-tetrazol-5-yl)phenyl]benzenesulfonamide

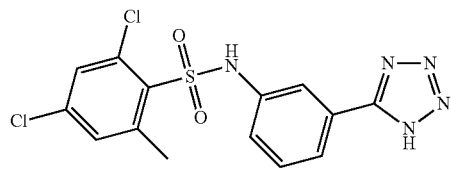 [SMILES: Cc1cc(Cl)cc(Cl)c1S(=O)(=O)Nc1cccc(-c2nnn[nH]2)c1]

The product was prepared according to General Procedure 1, described in Example 1, starting with 2,4-dichloro-6-methylbenzene sulfonyl chloride (14.3 mg, 0.055 mmol) and 5-(3-aminophenyl)tetrazole (8 mg, 0.05 mmol) yielding 15.3 mg (80%) of the title compound. MS (ESI+) calcd for $C_{14}H_{11}Cl_2N_5O_2S$ 383.001051, found 383.001071.

Example 54, General Procedure 5

3-[[3-(3,5-Dichlorophenyl)phenyl]sulfonylamino]benzoic acid

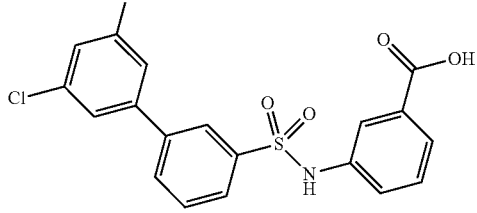

The intermediate methyl 3-{[(3',5'-dichlorobiphenyl-3-yl)sulfonyl]amino}benzoate was synthesised according to the first step in General Procedure 2, described in Example 5, with methyl 3-aminobenzoate (7.55 mg, 0.05 mmol) and [3-(3,5-dichlorophenyl)phenyl]sulfonyl chloride (17.7 mg, 0.055 mmol). The ester intermediate was dissolved in aqueous THF (2 mL, 1:1 THF/water) and then LiOH (11 mg, 0.26 mmol, 6 equiv.) was added. The reaction mixture was stirred at 56° C. overnight. After addition of HOAc (15 the solvents were evaporated giving the title compound in a mixture with LiOAc. MS (ESI+) calcd for $C_{19}H_{13}Cl_2NO_4S$ 420.994234, found 420.994364.

Example 55

N-[3-(1H-Tetrazol-5-yl)phenyl]-3-[4-(trifluoromethyl)phenyl]benzenesulfonamide

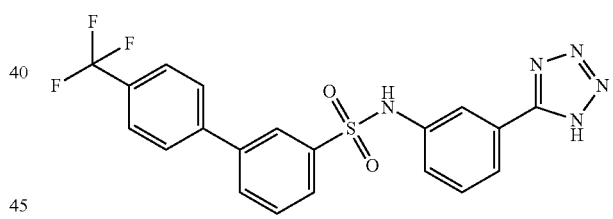

The product was synthesized according to General Procedure 1, described in Example 1, starting with {3-[4-(trifluoromethyl)phenyl]phenyl}sulfonyl chloride (17.6 mg, 0.055 mmol) and 5-(3-amino-phenyl)tetrazole (8 mg, 0.05 mmol) yielding 14.3 mg (64%) of the title compound. MS (ESI+) calcd for $C_{20}H_{14}F_3N_5O_2S$ 445.082030, found 445.081660.

Example 56

4-Bromo-N-[3-(1H-tetrazol-5-yl)phenyl]-2-(trifluoromethyl)benzenesulfonamide

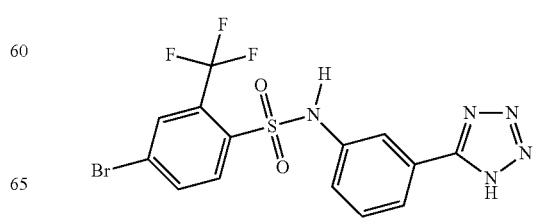

The product was synthesized according to General Procedure 1, described in Example 1, starting with 4-bromo-2-(trifluoromethyl)benzene sulfonyl chloride (17.8 mg, 0.055 mmol) and 5-(3-amino-phenyl)tetrazole (8 mg, 0.05 mmol) yielding 5.6 mg (25%) of the title compound. MS (ESI+) calcd for $C_{14}H_9BrF_3N_5O_2S$ 446.961242, found 446.961472.

Example 57

4-Bromo-2-fluoro-N-[3-(1H-tetrazol-5-yl)phenyl]benzenesulfonamide

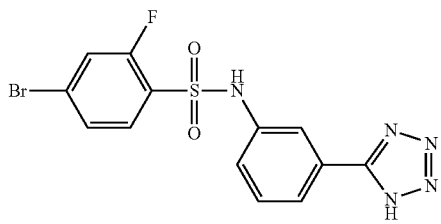 [SMILES: O=S(=O)(Nc1cccc(-c2nnn[nH]2)c1)c1ccc(Br)cc1F]

The product was synthesized according to General Procedure 1, described in Example 1, starting with 4-bromo-2-fluorobenzene sulfonyl chloride (17.8 mg, 0.055 mmol) and 5-(3-aminophenyl)tetrazole (8 mg, 0.05 mmol) affording 10.4 mg (52%) of the title compound. MS (ESI+) calcd for $C_{13}H_9BrFN_5O_2S$ 396.964436, found 396.963956.

Example 58

3-[5-[[3-(1H-Tetrazol-5-yl)phenyl]sulfamoyl]-2-thienyl]benzamide

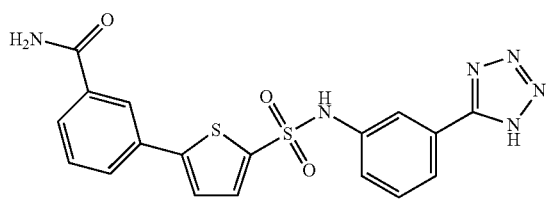 [SMILES: NC(=O)c1cccc(-c2ccc(S(=O)(=O)Nc3cccc(-c4nnn[nH]4)c3)s2)c1]

The product was prepared according to General Procedure 3, described in Example 22, starting from 5-bromo-N-[3-(1H-tetrazol-5-yl)phenyl]thiophene-2-sulfonamide (Intermediate 17) (19 mg, 0.05 mmol) and 3-aminocarbonylphenylboronic acid (10 mg, 0.06 mmol) giving 2.7 mg (13%) of the title compound. MS (ESI+) calcd for $C_{18}H_{14}N_6O_3S_2$ 426.056880, found 426.057610.

Example 59

5-(5-Chloro-1,2,4-thiadiazol-3-yl)-N-[3-(1H-tetrazol-5-yl)phenyl]thiophene-2-sulfonamide

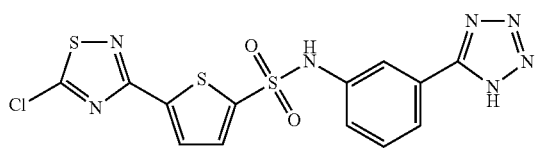 [SMILES: O=S(=O)(Nc1cccc(-c2nnn[nH]2)c1)c1ccc(-c2nsc(Cl)n2)s1]

The product was prepared according to General Procedure 1, described in Example 1, starting with 5-(5-chloro-1,2,4-thiadiazol-3-yl)thiophene-2-sulfonyl chloride (16.6 mg, 0.055 mmol) and 5-(3-amino-phenyl)tetrazole (8 mg, 0.05 mmol) affording 14.5 mg (68%) of the title compound. MS (ESI+) calcd for $C_{13}H_8ClN_7O_2S_3$ 424.959012, found 424.959022.

Example 60

5-Phenyl-N-[3-(1H-tetrazol-5-yl)phenyl]thiophene-2-sulfonamide

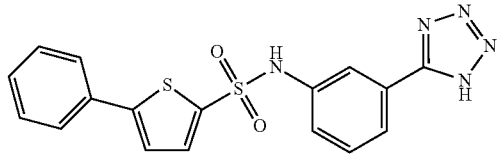

The product was prepared according to General Procedure 3, described in Example 22, starting from 5-bromo-N-[3-(1H-tetrazol-5-yl)phenyl]thiophene-2-sulfonamide (Intermediate 17) (19 mg, 0.05 mmol) and phenylboronic acid (7.3 mg, 0.06 mmol) affording 3.7 mg (19%) of the title compound. MS (ESI+) calcd for $C_{17}H_{13}N_5O_2S_2$ 383.051066, found 383.050986.

Example 61

3-[[5-(2-Methylsulfanylpyrimidin-4-yl)-2-thienyl]sulfonylamino]benzoic acid

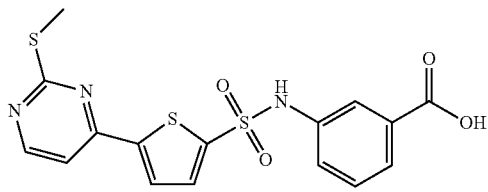 [SMILES: CSc1nccc(-c2ccc(S(=O)(=O)Nc3cccc(C(=O)O)c3)s2)n1]

The product was prepared according to General Procedure 1, described in Example 1, starting with 5-[2-(methylthio)pyrimidin-4-yl]thiophene-2-sulfonyl chloride (16.8 mg, 0.055 mmol) and 3-aminobenzoic acid (6.9 mg, 0.05 mmol) affording 16.0 mg (78%) of the title compound. MS (ESI+) calcd for $C_{16}H_{13}N_3O_4S_3$ 407.006818, found 407.007148.

Example 62

3-[[5-(2-Methyl-1,3-thiazol-4-yl)-2-thienyl]sulfonylamino]benzoic acid

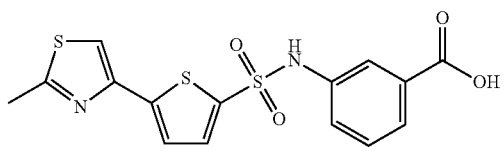 [SMILES: Cc1nc(-c2ccc(S(=O)(=O)Nc3cccc(C(=O)O)c3)s2)cs1]

The product was prepared according to General Procedure 1, described in Example 1, starting with 5-(2-methylthiazol-4-yl)thiophene-2-sulfonyl chloride (15.4 mg, 0.055 mmol) and 3-aminobenzoic acid (6.9 mg, 0.05 mmol) affording 2.6 mg (14%) of the title compound. MS (ESI+) calcd for $C_{15}H_{21}N_2O_4S_3$ 379.995919, found 379.995859.

Example 63

N-[3-(1H-Tetrazol-5-yl)phenyl]-5-[5-(trifluoromethyl)isoxazol-3-yl]thiophene-2-sulfonamide

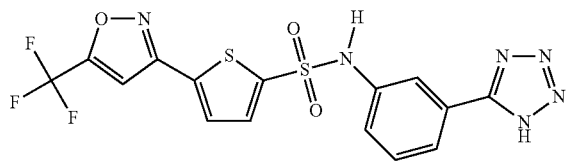 [SMILES: O=S(=O)(Nc1cccc(-c2nnn[nH]2)c1)c1ccc(-c2cc(C(F)(F)F)on2)s1]

The product was prepared according to General Procedure 1, described in Example 1, starting with 5-[5-(trifluoromethyl)isoxazol-3-yl-thiophene-2-sulfonyl chloride (17.5 mg, 0.055 mmol) and 5-(3-amino-phenyl)tetrazole (8 mg, 0.05 mmol) affording 9.5 mg (43%) of the title compound. $^1$H NMR (500 MHz, DMSO-$d_6$) δ ppm 7.34 (d, J=7.92 Hz, 1 H) 7.51 (t, J=7.92 Hz, 1 H) 7.71 (d, J=3.96 Hz, 1 H) 7.76 (d, J=7.92 Hz, 1 H) 7.82 (d, J=3.96 Hz, 1 H) 7.90-7.92 (m, 1 H) 8.08 (s, 1 H).

Example 64

N-[3-(1H-Tetrazol-5-yl)phenyl]benzofuran-2-sulfonamide

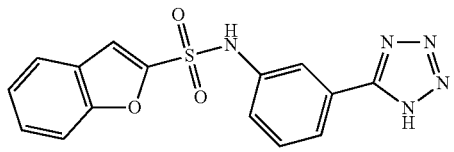 [SMILES: O=S(=O)(Nc1cccc(-c2nnn[nH]2)c1)c1cc2ccccc2o1]

The product was prepared according to General Procedure 1, described in Example 1, starting with 1-benzofuran-2-sulfonyl chloride (11.9 mg, 0.055 mmol) and 5-(3-aminophenyl)-tetrazole (8 mg, 0.05 mmol) affording 7.8 mg (46%) of the title compound. MS (ESI+) calcd for $C_{15}H_{11}N_5O_3S$ 341.058260, found 341.058160.

Example 65, General Procedure 6

5-Isoxazol-3-yl-N-[3-(1H-tetrazol-5-yl)phenyl]thiophene-2-sulfonamide

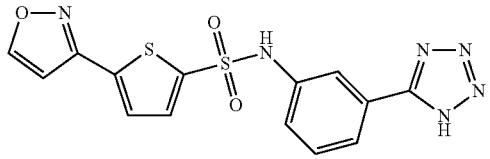 [SMILES: O=S(=O)(Nc1cccc(-c2nnn[nH]2)c1)c1ccc(-c2ccon2)s1]

The product was prepared according to General Procedure 1, described in Example 1, with 5-isoxazol-3-ylthiophene-2-sulfonyl chloride (13.7 mg, 0.055 mmol) and 5-(3-aminophenyl)tetrazole (8.0 mg, 0.050 mmol) and with a slightly modified purification method using 0.1% TFA in water as buffet. The title compound was obtained in 54% yield (11.1 mg). MS (ESI+) calcd mass for $C_{14}H_{10}N_6O_3S_2$ 374.025580, found 374.025400.

Example 66

2,4,6-Trichloro-N-[3-(1H-tetrazol-5-yl)phenyl]benzenesulfonamide

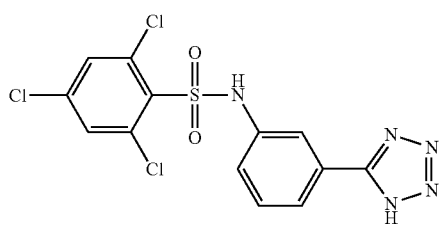 [SMILES: O=S(=O)(Nc1cccc(-c2nnn[nH]2)c1)c1c(Cl)cc(Cl)cc1Cl]

The product was prepared according to General Procedure 6, described in Example 65, with 2,4,6-trichlorobenzenesulfonyl chloride (15.4 mg, 0.055 mmol) and 5-(3-aminophenyl)tetrazole (8.0 mg, 0.050 mmol). The title compound was obtained in 51% yield (10.7 mg). MS (ESI+) calcd mass for $C_{13}H_8Cl_3N_5O_2S$ 402.946428, found 402.946218.

Example 67

2,3-Dichloro-N-[3-(1H-tetrazol-5-yl)phenyl]benzenesulfonamide

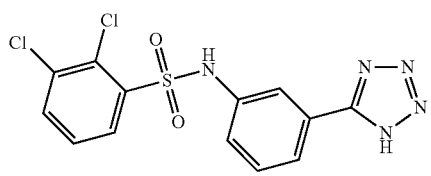 [SMILES: O=S(=O)(Nc1cccc(-c2nnn[nH]2)c1)c1cccc(Cl)c1Cl]

The product was prepared according to General Procedure 6, described in Example 65, with 2,3-dichlorobenzenesulfonyl chloride (13.5 mg, 0.055 mmol) and 5-(3-aminophenyl) tetrazole (8.0 mg, 0.050 mmol). The title compound was obtained in 74% yield (13.7 mg). MS (ESI+) calcd mass for $C_{13}H_9Cl_2N_5O_2S$ 368.985401, found 368.984901.

Example 68

2,5-Dichloro-N-[3-(1H-tetrazol-5-yl)phenyl]benzenesulfonamide

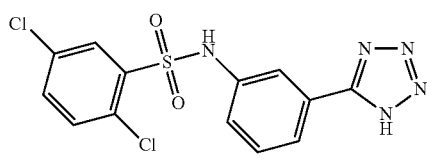 [SMILES: O=S(=O)(Nc1cccc(-c2nnn[nH]2)c1)c1cc(Cl)ccc1Cl]

The product was prepared according to General Procedure 6, described in Example 65, with 2,5-dichlorobenzenesulfonyl chloride (13.5 mg, 0.055 mmol) and 5-(3-aminophenyl)

tetrazole (8.0 mg, 0.050 mmol). The title compound was obtained in 45% yield (8.3 mg). MS (ESI+) calcd mass for $C_{13}H_9Cl_2N_5O_2S$ 368.985401, found 368.985761.

Example 69

3-Chloro-2-methyl-N-[3-(1H-tetrazol-5-yl)phenyl]benzenesulfonamide

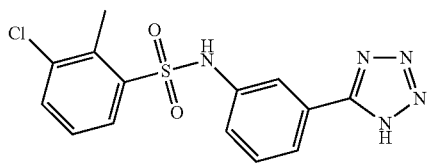 [SMILES: Cc1c(Cl)cccc1S(=O)(=O)Nc1cccc(-c2nnn[nH]2)c1]

The product was prepared according to General Procedure 6, described in Example 65, with 3-chloro-2-methylbenzenesulfonyl chloride (12.4 mg, 0.055 mmol) and 5-(3-aminophenyl)tetrazole (8.0 mg, 0.050 mmol). The title compound was obtained in 58% yield (10.1 mg). MS (ESI+) calcd mass for $C_{14}H_{12}ClN_5O_2S$ 349.040023, found 349.040413.

Example 70

2,4-Dichloro-N-[3-(1H-tetrazol-5-yl)phenyl]benzenesulfonamide

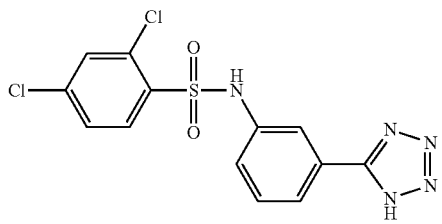 [SMILES: O=S(=O)(Nc1cccc(-c2nnn[nH]2)c1)c1ccc(Cl)cc1Cl]

The product was prepared according to General Procedure 6, described in Example 65, with 2,4-dichlorobenzenesulfonyl chloride (13.5 mg, 0.055 mmol) and 5-(3-aminophenyl)tetrazole (8.0 mg, 0.050 mmol). The title compound was obtained in 8% yield (1.5 mg). MS (ESI+) calcd mass for $C_{13}H_9Cl_2N_5O_2S$ 368.985401, found 368.984681.

Example 71

2,4,5-Trichloro-N-[3-(1H-tetrazol-5-yl)phenyl]benzenesulfonamide

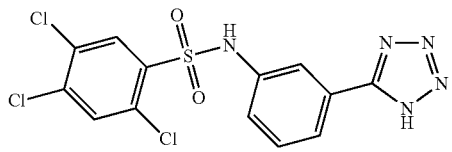 [SMILES: O=S(=O)(Nc1cccc(-c2nnn[nH]2)c1)c1cc(Cl)c(Cl)cc1Cl]

The product was prepared according to General Procedure 6, described in Example 65, with 2,4,5-trichlorobenzenesulfonyl chloride (15.4 mg, 0.055 mmol) and 5-(3-aminophenyl)tetrazole (8.0 mg, 0.050 mmol). The title compound was obtained in 57% yield (11.4 mg). MS (ESI+) calcd mass for $C_{13}H_8Cl_3N_5O_2S$ 402.946428, found 402.946388.

Example 72

2,4-Difluoro-N-[3-(1H-tetrazol-5-yl)phenyl]benzenesulfonamide

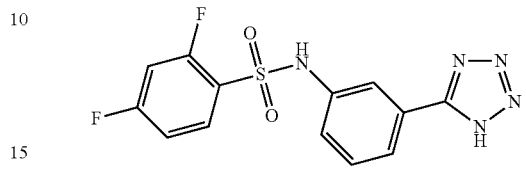

The product was prepared according to General Procedure 6, described in Example 65, with 2,4-difluorobenzenesulfonyl chloride (11.7 mg, 0.055 mmol) and 5-(3-amino-phenyl)tetrazole (8.0 mg, 0.050 mmol). The title compound was obtained in 56% yield (9.5 mg). MS (ESI+) calcd mass for $C_{13}H_9F_2N_5O_2S$ 337.044502, found 337.044202.

Example 73

7-Chloro-N-[3-(1H-tetrazol-5-yl)phenyl]-2,1,3-benzoxadiazole-4-sulfonamide

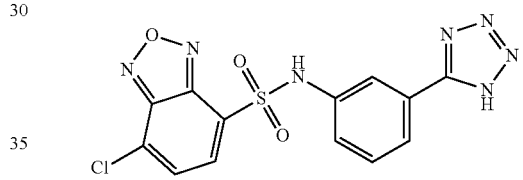

The product was prepared according to General Procedure 6, described in Example 65, with 4-chloro-7-chlorosulfonyl-2,1,3-benzoxadiazole (13.9 mg, 0.055 mmol) and 5-(3-aminophenyl)tetrazole (8.0 mg, 0.050 mmol). The title compound was obtained in 52% yield (9.8 mg). MS (ESI+) calcd mass for $C_{13}H_8ClN_7O_3S$ 377.009786, found 377.010126.

Example 74

Methyl 3-{[(5-chloro-3-methyl-1-benzothien-2-yl)sulfonyl]amino}benzoate

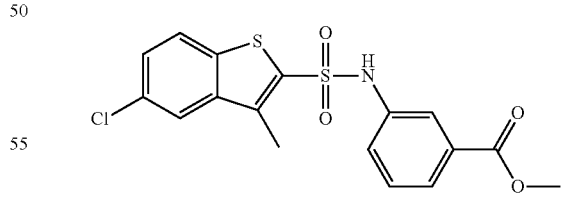

A solution of 5-chloro-3-methylbenzothiophene-2-sulfonyl chloride (50 mg, 0.178 mmol) and methyl 3-aminobenzoate (17 mg, 0.112 mmol) in aqueous dioxane (900 μL, 8:1 dioxane/water) was stirred at room temperature for 4 days. The reaction mixture was diluted with MeOH (1 mL) and the crude product was purified by reversed phase chromatography (ACE C8, 5 μm, 21×50 mm, flow 25 ml/min, 0.1% TFA in water/MeCN over 6 minutes). The title compound was obtained in 69% yield (30.5 mg). $^1$H NMR (500 MHz, MeOH-d$_4$) δ ppm 2.49 (s, 3 H) 3.85 (s, 3 H) 7.35 (ddd, J=8.12, 7.31, 0.56 Hz, 1 H) 7.38 (ddd, J=8.12, 2.20, 1.58 Hz, 1 H) 7.46 (dd, J=8.65, 2.05 Hz, 1 H) 7.74 (dt, J=7.31, 1.58 Hz, 1 H) 7.82 (ddd, J=2.20, 1.58, 0.56 Hz, 1 H) 7.84 (dd, J=8.65, 0.56 Hz, 1 H) 7.85 (dd, J=2.05, 0.56 Hz, 1 H). MS (ESI+) m/z 396 [M+H]$^+$.

Example 75

3-{[(3-Methyl-1-benzothiophen-2-yl)sulfonyl]amino}benzoic acid

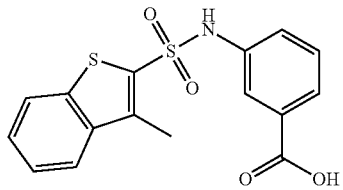 [SMILES: Cc1c(S(=O)(=O)Nc2cccc(C(=O)O)c2)sc2ccccc12]

The product was prepared according to General Procedure 1, described in Example 1, with 3-methylbenzothiophene-2-sulfonyl chloride (Intermediate 11) (25 mg, 0.10 mmol) and 3-aminobenzoic acid (28 mg, 0.20 mmol) using a modified reaction time (4 hours) and a modified reaction temperature (60° C.). The title compound was obtained in 26% yield (8.9 mg). MS (ESI+) calcd mass for C$_{16}$H$_{13}$NO$_4$S$_2$ 347.028599, found 347.028659.

Example 76

3-{[(5-Fluoro-3-methyl-1-benzothiophen-2-yl)sulfonyl]amino}benzoic acid

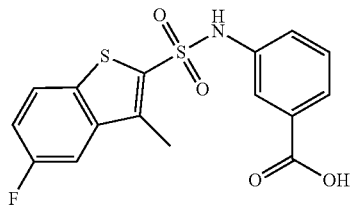 [SMILES: Cc1c(S(=O)(=O)Nc2cccc(C(=O)O)c2)sc2ccc(F)cc12]

The product was prepared according to General Procedure 1, described in Example 1, with 5-fluoro-3-methylbenzothiophene-2-sulfonyl chloride (Intermediate 14) (26 mg, 0.10 mmol) and 3-aminobenzoic acid (26 mg, 0.19 mmol). The title compound was obtained in 45% yield (16.5 mg). MS (ESI+) calcd mass for C$_{16}$H$_{12}$FNO$_4$S$_2$ 365.019178, found 365.018988.

Example 77

3-{[(5-Methoxy-3-methyl-1-benzothiophen-2-yl)sulfonyl]amino}benzoic acid

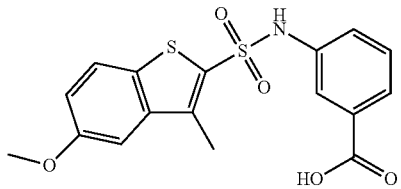 [SMILES: COc1ccc2sc(S(=O)(=O)Nc3cccc(C(=O)O)c3)c(C)c2c1]

The product was prepared according to General Procedure 1, described in Example 1, with 5-methoxy-3-methylbenzothiophene-2-sulfonyl chloride (Intermediate 8) (85 mg, 0.31 mmol) and 3-aminobenzoic acid (42 mg, 0.31 mmol). The title compound was obtained in 33% yield (38.2 mg). MS (ESI+) calcd mass for C$_{17}$H$_{15}$NO$_5$S$_2$ 377.039164, found 377.039474.

Example 78

3-{[(5-Pyridin-2-yl-2-thienyl)sulfonyl]amino}benzoic acid

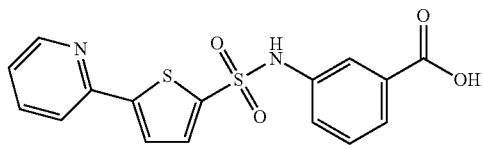 [SMILES: O=C(O)c1cccc(NS(=O)(=O)c2ccc(-c3ccccn3)s2)c1]

The product was prepared according to General Procedure 6, described in Example 65, with 5-(2-pyridyl)thiophene-2-sulfonyl chloride (13.5 mg, 0.055 mmol) and 3-aminobenzoic acid (6.9 mg, 0.050 mmol). The title compound was obtained in 18% yield (3.2 mg). MS (ESI+) calcd mass for C$_{16}$H$_{12}$N$_2$O$_4$S$_2$ 360.023848, found 360.023668.

Example 79

3-{[(5-Isoxazol-3-yl-2-thienyl)sulfonyl]amino}benzoic acid

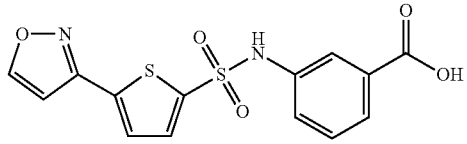 [SMILES: O=C(O)c1cccc(NS(=O)(=O)c2ccc(-c3ccon3)s2)c1]

The product was prepared according to General Procedure 6, described in Example 65, with 5-isoxazol-3-ylthiophene-2-sulfonyl chloride (13.7 mg, 0.055 mmol) and 3-aminobenzoic acid (6.9 mg, 0.050 mmol). The title compound was obtained in 55% yield (9.6 mg). MS (ESI+) calcd mass for C$_{14}$H$_{10}$N$_2$O$_5$S$_2$ 350.003113, found 350.002783.

Example 80

3-[(Biphenyl-3-ylsulfonyl)amino]benzoic acid

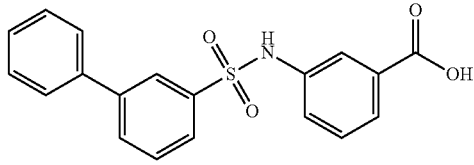 [SMILES: O=C(O)c1cccc(NS(=O)(=O)c2cccc(-c3ccccc3)c2)c1]

The product was prepared according to General Procedure 1, described in Example 1, with 3-phenylbenzenesulfonylchloride (13.9 mg, 0.055 mmol) and 3-aminobenzoic acid (6.9 mg, 0.050 mmol). The title compound was obtained in 100% yield (17.7 mg). MS (ESI+) calcd mass for $C_{19}H_{15}NO_4S$ 353.072179, found 353.071899.

Example 81

2-Chloro-4-fluoro-N-[3-(1H-tetrazol-5-yl)phenyl]benzenesulfonamide

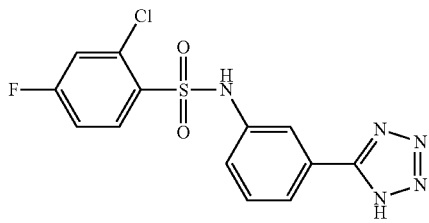 [SMILES: O=S(=O)(Nc1cccc(-c2nnn[nH]2)c1)c1ccc(F)cc1Cl]

The product was prepared according to General Procedure 6, described in Example 65, with 2-chloro-4-fluorobenzenesulfonyl chloride (12.6 mg, 0.055 mmol) and 5-(3-aminophenyl)tetrazole (8.0 mg, 0.050 mmol). The title compound was obtained in 62% yield (10.9 mg). MS (ESI+) calcd mass for $C_{13}H_9ClFN_5O_2S$ 353.014951, found 353.015041.

Example 82

N-[3-(1H-Tetrazol-5-yl)phenyl]-1-benzothiophene-2-sulfonamide

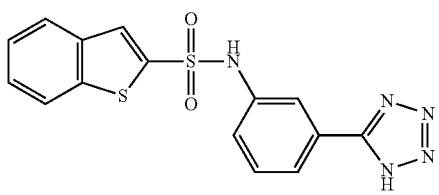 [SMILES: O=S(=O)(Nc1cccc(-c2nnn[nH]2)c1)c1cc2ccccc2s1]

The product was prepared according to General Procedure 1, described in Example 1, with 1-benzothiophene-2-sulfonyl chloride (12.8 mg, 0.055 mmol) and 5-(3-amino-phenyl)tetrazole (8.0 mg, 0.050 mmol). The title compound was obtained in 60% yield (10.8 mg). MS (ESI+) calcd mass for $C_{15}H_{11}N_5O_2S_2$ 357.035416, found 357.036256.

Example 83

4-(1,3-Oxazol-5-yl)-N-[3-(1H-tetrazol-5-yl)phenyl]benzenesulfonamide

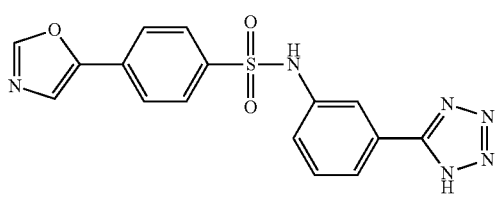 [SMILES: O=S(=O)(Nc1cccc(-c2nnn[nH]2)c1)c1ccc(-c2cnco2)cc1]

The product was prepared according to General Procedure 6, described in Example 65, with 4-(1,3-oxazol-5-yl)benzenesulfonyl chloride (17.2 mg, 0.055 mmol) and 5-(3-aminophenyl)tetrazole (8.0 mg, 0.050 mmol). The title compound was obtained in 23% yield (4.2 mg). MS (ESI+) calcd mass for $C_{16}H_{12}N_6O_3S$ 368.069159, found 368.069509.

Example 84

3-[(1-Benzothien-2-ylsulfonyl)amino]benzoic acid

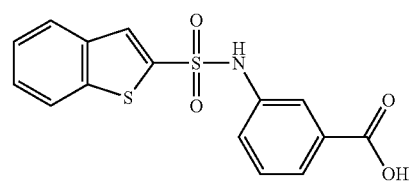 [SMILES: O=C(O)c1cccc(NS(=O)(=O)c2cc3ccccc3s2)c1]

The product was prepared according to General Procedure 1, described in Example 1, with 1-benzothiophene-2-sulfonyl chloride (12.8 mg, 0.055 mmol) and 3-aminobenzoic acid (6.9 mg, 0.050 mmol). The title compound was obtained in 41% yield (8.9 mg). MS (ESI+) calcd mass for $C_{15}H_{11}NO_4S_2$ 333.012949, found 333.014269.

Example 85

4'-Methoxy-N-[3-(1H-tetrazol-5-yl)phenyl]biphenyl-4-sulfonamide

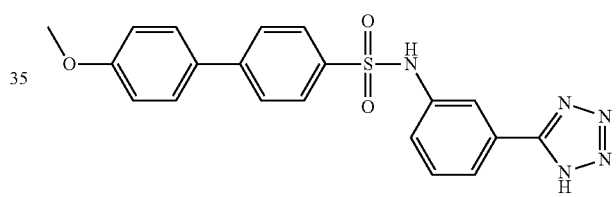

The product was prepared according to General Procedure 1, described in Example 1, with 4'-methoxy[1,1'-biphenyl]-4-sulfonyl chloride (15.6 mg, 0.055 mmol) and 5-(3-aminophenyl)tetrazole (8.0 mg, 0.050 mmol). The title compound was obtained in 79% yield (16 mg). MS (ESI+) calcd mass for $C_{20}H_{17}N_5O_3S$ 407.105210, found 407.105280.

Example 86

3',4'-Dichloro-N-[3-(1H-tetrazol-5-yl)phenyl]biphenyl-4-sulfonamide

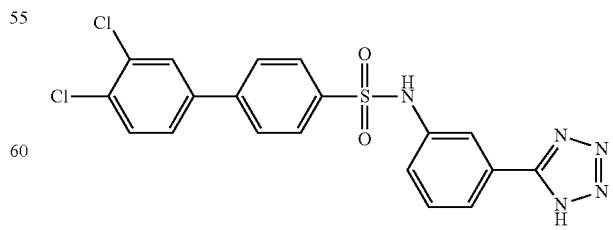

The product was prepared according to General Procedure 1, described in Example 1, with 3',4'-dichloro[1,1'-biphenyl]-4-sulfonyl chloride (17.7 mg, 0.055 mmol) and 5-(3-aminophenyl)tetrazole (8.0 mg, 0.050 mmol). The title compound was obtained in 18% yield (4.1 mg). MS (ESI+) calcd mass for $C_{19}H_{13}Cl_2N_5O_2S$ 445.016701, found 445.016581.

Example 87

5-Isoxazol-5-yl-N-[3-(1H-tetrazol-5-yl)phenyl]thiophene-2-sulfonamide

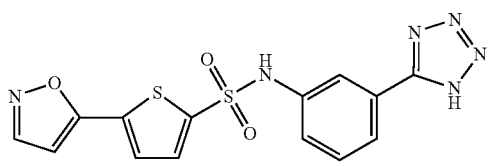 [SMILES: O=S(=O)(Nc1cccc(-c2nnn[nH]2)c1)c1ccc(-c2ccno2)s1]

The title compound was prepared according to General Procedure 1, described in Example 1, with 5-isoxazol-5-ylthiophene-2-sulfonyl chloride (13.7 mg, 0.055 mmol) and 5-(3-aminophenyl)tetrazole (8.0 mg, 0.050 mmol). MS (ESI+) calcd mass for $C_{14}H_{10}N_6O_3S_2$ 374.025580, found 374.025420.

Example 88

Methyl 3-({[5-(2-methyl-1,3-thiazol-4-yl)-2-thienyl]sulfonyl}amino)benzoate

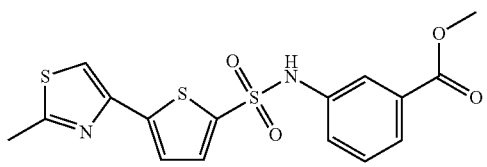

The title compound was prepared according to General Procedure 1, described in Example 1, with 5-(2-methylthiazol-4-yl)thiophene-2-sulphonylchloride (15.4 mg, 0.055 mmol) and methyl 3-aminobenzoate (7.6 mg, 0.050 mmol). $^1$H NMR (400 MHz, DMSO-$d_6$) δ ppm 1.82-1.83 (s, 3H), 2.98-2.99 (s, 3H), 6.59-6.62 (m, 2H), 6.67-6.68 (s, 2H), 6.81-6.84 (m, 1H), 6.93-6.94 (m, 1H). MS (ESI+) m/z 395 [M+H]+.

Example 89

3-{[(5-Methyl-1-benzothiophen-2-yl)sulfonyl]amino}benzoic acid

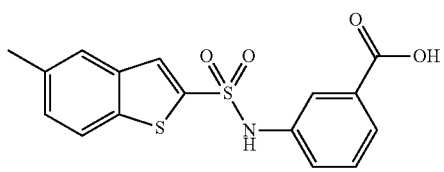 [SMILES: Cc1ccc2sc(S(=O)(=O)Nc3cccc(C(=O)O)c3)cc2c1]

The product was prepared according to General Procedure 6, described in Example 65, with 5-methylbenzothiophene-2-sulfonyl chloride (30.0 mg, 0.12 mmol), pyridine (49 µL, 0.61 mmol) and 3-aminobenzoic acid (16.7 mg, 0.10 mmol). The title compound was obtained in 66% yield (23 mg). MS (ESI+) calcd mass for $C_{16}H_{13}NO_4S_2$ 347.028599, found 347.029559.

Example 90

4'-Chloro-N-[3-(1H-tetrazol-5-yl)phenyl]biphenyl-3-sulfonamide

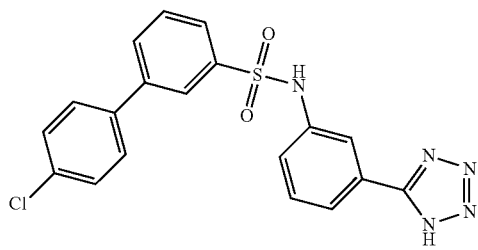 [SMILES: O=S(=O)(Nc1cccc(-c2nnn[nH]2)c1)c1cccc(-c2ccc(Cl)cc2)c1]

The product was prepared according to General Procedure 1, described in Example 1, with [3-(4-chlorophenyl)phenyl]sulfonyl chloride (15.8 mg, 0.055 mmol) and 5-(3-aminophenyl)tetrazole (8.0 mg, 0.050 mmol). The title compound was obtained in 92% yield (18.9 mg). MS (ESI+) calcd mass for $C_{19}H_{14}ClN_5O_2S$ 411.055673, found 411.055743.

Example 91

3',4'-Dichloro-N-[3-(1H-tetrazol-5-yl)phenyl]biphenyl-3-sulfonamide

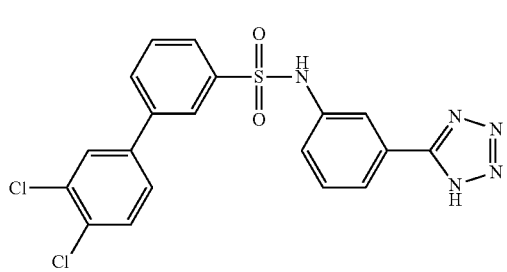 [SMILES: O=S(=O)(Nc1cccc(-c2nnn[nH]2)c1)c1cccc(-c2ccc(Cl)c(Cl)c2)c1]

The product was prepared according to General Procedure 1, described in Example 1, with [[3-(3,4-dichlorophenyl)phenyl]sulfonyl chloride (17.7 mg, 0.055 mmol) and 5-(3-aminophenyl)tetrazole (8.0 mg, 0.050 mmol). The title compound was obtained in 77% yield (17.2 mg). MS (ESI+) calcd mass for $C_{19}H_{13}Cl_2N_5O_2S$ 445.016701, found 445.016851.

Example 92

Methyl 3-({[3-methyl-5-(1-methylethyl)-1-benzothiophen-2-yl]sulfonyl}amino)benzoate

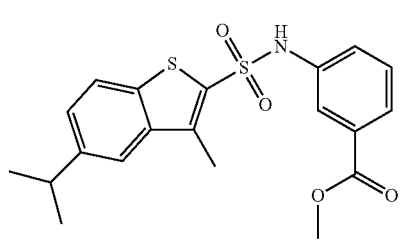 [SMILES: COC(=O)c1cccc(NS(=O)(=O)c2sc3ccc(C(C)C)cc3c2C)c1]

The product was prepared according to General Procedure 6, described in Example 65, with 5-isopropyl-3-methylbenzothiophene-2-sulfonyl chloride (Intermediate 2) (20.0 mg, 0.069 mmol) and methyl 3-aminobenzoate (8.0 mg, 0.053 mmol). The title compound was obtained in 73% yield (15.6 mg). $^1$H NMR (500 MHz, MeOH-$d_4$) δ ppm 1.29 (d, J=6.95 Hz, 6 H) 2.51 (s, 3 H) 3.04 (spt, J=6.95 Hz, 1 H) 3.84 (s, 3 H) 7.33 (ddd, J=8.11, 7.51, 0.57 Hz, 1 H) 7.37 (ddd, J=8.11, 2.21, 1.37 Hz, 1 H) 7.41 (ddd, J=8.42, 1.71, 0.45 Hz, 1 H) 7.64 (td, J=1.71, 0.63 Hz, 1 H) 7.72 (ddd, J=7.51, 1.60, 1.37 Hz, 1 H) 7.75 (dd, J=8.43, 0.63 Hz, 1 H) 7.82 (ddd, J=2.21, 1.60, 0.57 Hz, 1 H). MS (ESI+) m/z 404 [M+H]$^+$.

Example 93

3-{[(4'-Chlorobiphenyl-3-yl)sulfonyl]amino}benzoic acid

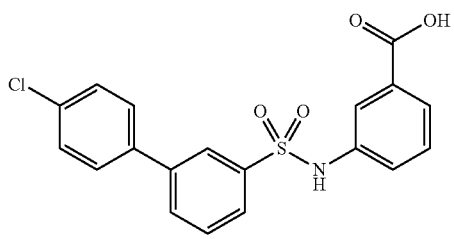 [SMILES: O=C(O)c1cccc(NS(=O)(=O)c2cccc(-c3ccc(Cl)cc3)c2)c1]

The product was prepared according to General Procedure 5, described in Example 54, with methyl 3-aminobenzoate (7.55 mg, 0.05 mmol) and 4'-chlorobiphenyl-3-sulfonyl chloride (15.8 mg, 0.055 mmol). The title compound was obtained in a mixture with LiOAc. MS (ESI+) calcd mass for $C_{19}H_{14}ClNO_4S$ 387.033206, found 387.033976.

Example 94

3-{[(4'-Fluorobiphenyl-3-yl)sulfonyl]amino}benzoic acid

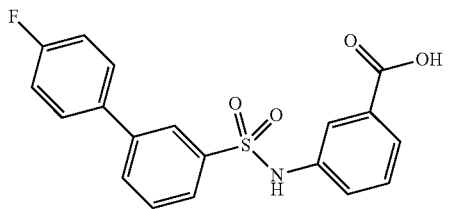 [SMILES: O=C(O)c1cccc(NS(=O)(=O)c2cccc(-c3ccc(F)cc3)c2)c1]

The product was prepared according to General Procedure 5, described in Example 54, with methyl 3-aminobenzoate (7.55 mg, 0.05 mmol) and 4'-fluorobiphenyl-3-sulfonyl chloride (14.9 mg, 0.055 mmol). The title compound was obtained in a mixture with LiOAc. MS (ESI+) calcd mass for $C_{19}H_{14}FNO_4S$ 371.062757, found 371.062917.

Example 95

3-{[(4'-Methoxybiphenyl-3-yl)sulfonyl]amino}benzoic acid

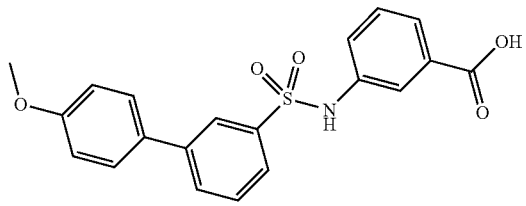 [SMILES: COc1ccc(-c2cccc(S(=O)(=O)Nc3cccc(C(=O)O)c3)c2)cc1]

The product was prepared according to General Procedure 5, described in Example 54, with methyl 3-aminobenzoate (7.55 mg, 0.05 mmol) and 4'-methoxybiphenyl-3-sulfonyl chloride (15.5 mg, 0.055 mmol). The title compound was obtained in a mixture with LiOAc. MS (ESI+) calcd mass for $C_{20}H_{17}NO_5S$ 383.082743, found 383.082463.

Example 96

3-{[(3',4'-Dichlorobiphenyl-3-yl)sulfonyl]amino}benzoic acid

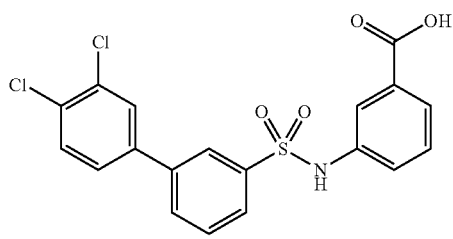 [SMILES: O=C(O)c1cccc(NS(=O)(=O)c2cccc(-c3ccc(Cl)c(Cl)c3)c2)c1]

The product was prepared according to General Procedure 5, described in Example 54, with methyl 3-aminobenzoate (7.55 mg, 0.05 mmol) and 3',4'-dichlorobiphenyl-3-sulfonyl chloride (17.7 mg, 0.055 mmol). The title compound was obtained in a mixture with LiOAc. MS (ESI+) calcd mass for $C_{19}H_{13}Cl_2NO_4S$ 420.994234, found 420.994054.

Example 97

5-(3-Methoxyphenyl)-N-[3-(1H-tetrazol-5-yl)phenyl]thiophene-2-sulfonamide

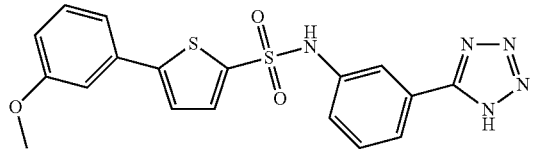 [SMILES: COc1cccc(-c2ccc(S(=O)(=O)Nc3cccc(-c4nnn[nH]4)c3)s2)c1]

The title compound was prepared according to General Procedure 3, described in Example 22, using 5-bromo-N-[3-(1H-tetrazol-5-yl)phenyl]thiophene-2-sulfonamide (Intermediate 17) (19 mg, 0.055 mmol) and 3-methoxyphenylboronic acid (9 mg, 0.06 mmol). MS (ESI+) calcd mass for $C_{18}H_{15}N_5O_3S_2$ 413.061631, found 413.062021.

Example 98

5-(3,4-Dichlorophenyl)-N-[3-(1H-tetrazol-5-yl)phenyl]thiophene-2-sulfonamide

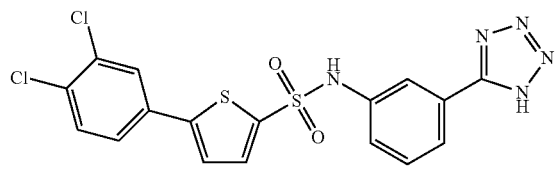 [SMILES: O=S(=O)(Nc1cccc(-c2nnn[nH]2)c1)c1ccc(-c2ccc(Cl)c(Cl)c2)s1]

The product was prepared according to General Procedure 3, described in Example 22, using 5-bromo-N-[3-(1H-tetrazol-5-yl)phenyl]thiophene-2-sulfonamide (Intermediate 17) (19 mg, 0.055 mmol) and 3,4-dichlorophenylboronic acid (11 mg, 0.06 mmol). The title compound was obtained in 4% yield (0.8 mg). MS (ESI+) m/z 452 [M+H]$^+$.

Example 99

N-[3-(1H-Tetrazol-5-yl)phenyl]-5-[3-(trifluoromethyl)phenyl]thiophene-2-sulfonamide

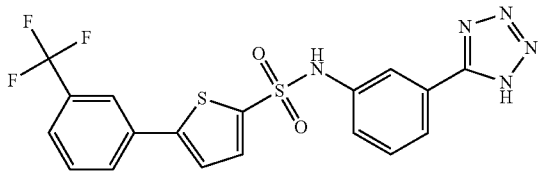 [SMILES: O=S(=O)(Nc1cccc(-c2nnn[nH]2)c1)c1ccc(-c2cccc(C(F)(F)F)c2)s1]

The product was prepared according to General Procedure 3, described in Example 22, using 5-bromo-N-[3-(1H-tetrazol-5-yl)phenyl]thiophene-2-sulfonamide (Intermediate 17) (19 mg, 0.055 mmol) and 3-trifluoromethylphenylboronic acid (11 mg, 0.06 mmol). The title compound was obtained in 48% yield (10.8 mg). MS (ESI+) calcd mass for $C_{18}H_{12}F_3N_5O_2S_2$ 451.038451, found 451.038591.

Example 100

5-(2-Methylphenyl)-N-[3-(1H-tetrazol-5-yl)phenyl]thiophene-2-sulfonamide

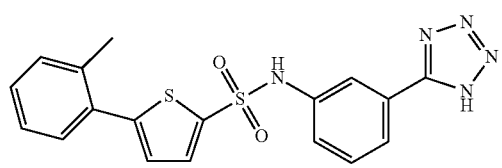 [SMILES: Cc1ccccc1-c1ccc(S(=O)(=O)Nc2cccc(-c3nnn[nH]3)c2)s1]

The product was prepared according to General Procedure 3, described in Example 22, using 5-bromo-N-[3-(1H-tetrazol-5-yl)phenyl]thiophene-2-sulfonamide (Intermediate 17) (19 mg, 0.055 mmol) and o-tolylboronic acid (8 mg, 0.06 mmol). The title compound was obtained in 41% yield (8.1 mg). MS (ESI+) calcd mass for $C_{18}H_{15}N_5O_2S_2$ 397.066716, found 397.066896.

Example 101

5-(2,4-Difluorophenyl)-N-[3-(1H-tetrazol-5-yl)phenyl]thiophene-2-sulfonamide

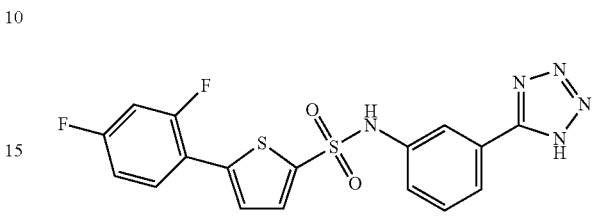

The product was prepared according to General Procedure 3, described in Example 22, using 5-bromo-N-[3-(1H-tetrazol-5-yl)phenyl]thiophene-2-sulfonamide (Intermediate 17) (19 mg, 0.055 mmol) and 2,4-difluorophenylboronic acid (9 mg, 0.06 mmol). The title compound was obtained in 33% yield (6.9 mg). MS (ESI+) calcd mass for $C_{17}H_{11}F_2N_5O_2S_2$ 419.032222, found 419.032372.

Example 102

5-(3-Chloro-4-fluorophenyl)-N-[3-(1H-tetrazol-5-yl)phenyl]thiophene-2-sulfonamide

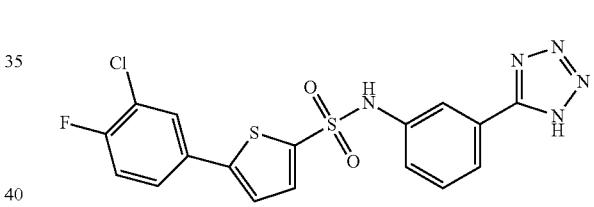

The product was prepared according to General Procedure 3, described in Example 22, using 5-bromo-N-[3-(1H-tetrazol-5-yl)phenyl]thiophene-2-sulfonamide (Intermediate 17) (19 mg, 0.055 mmol) and 3-chloro-4-fluorophenyl-boronic acid (10 mg, 0.06 mmol). The title compound was obtained in 31% yield (6.7 mg). MS (ESI+) calcd mass for $C_{17}H_{11}ClFN_5O_2S_2$ 435.002672, found 435.002662.

Example 103

5-(3-Chlorophenyl)-N-[3-(1H-tetrazol-5-yl)phenyl]thiophene-2-sulfonamide

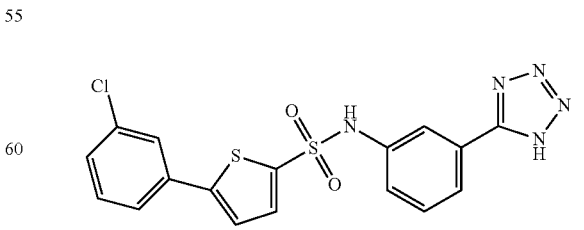

The product was prepared according to General Procedure 3, described in Example 22, using 5-bromo-N-[3-(1H-tetrazol-5-yl)phenyl]thiophene-2-sulfonamide (Intermediate 17)

(19 mg, 0.055 mmol) and 3-chlorophenylboronic acid (9 mg, 0.06 mmol). The title compound was obtained in 26% yield (5.4 mg). MS (ESI+) calcd mass for $C_{17}H_{12}ClN_5O_2S_2$ 417.012094, found 417.012844.

Example 104

5-Pyridin-4-yl-N-[3-(1H-tetrazol-5-yl)phenyl]thiophene-2-sulfonamide

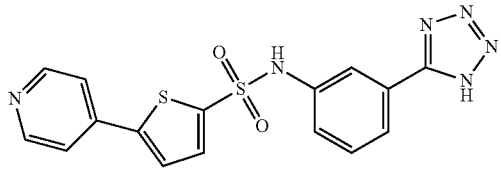 [SMILES: O=S(=O)(Nc1cccc(-c2nnn[nH]2)c1)c1ccc(-c2ccncc2)s1]

The product was prepared according to General Procedure 3, described in Example 22, using 5-bromo-N-[3-(1H-tetrazol-5-yl)phenyl]thiophene-2-sulfonamide (Intermediate 17) (19 mg, 0.055 mmol) and pyridine-4-boronic acid (7 mg, 0.06 mmol). The title compound was obtained in 16% yield (3.1 mg). MS (ESI+) calcd mass for $C_{16}H_{12}N_6O_2S_2$ 384.046315, found 384.047755.

Example 105

3-{[(3-Methyl-5-morpholin-4-yl-1-benzothiophen-2-yl)sulfonyl]amino}benzoic acid

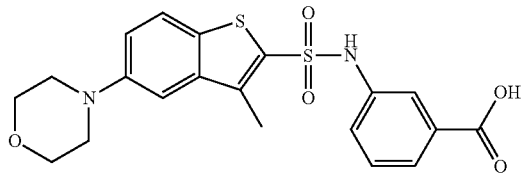 [SMILES: Cc1c(S(=O)(=O)Nc2cccc(C(=O)O)c2)sc2ccc(N3CCOCC3)cc12]

A mixture of ethyl 3-{[(5-bromo-3-methyl-1-benzothiophen-2-yl)sulfonyl]amino}benzoate (Intermediate 18) (23 mg, 0.05 mmol), morpholine (9 mg, 0.10 mmol), PdOAc$_2$ (0.6 mg, 0.0025 mmol), 2-(di-$^t$butylphosphino)biphenyl (1 mg, 0.0035 mmol) and Cs$_2$CO$_3$ (66 mg, 0.25 mmol) in dioxane (200 µL) was heated at 110° C. for 20 h giving the intermediate ethyl 3-{[(3-methyl-5-morpholin-4-yl-1-benzothiophen-2-yl)sulfonyl]amino}benzoate. The intermediate ester was hydrolyzed using LiOH in aqueous THF (1 mL, 1:1 water/THF) giving the title compound. MS (ESI+) calcd mass for $C_{20}H_{20}N_2O_5S_2$ 432.081363, found 432.081153.

Example 106

2-(1H-Pyrrol-1-yl)ethyl 3-{[(5-chloro-3-methyl-1-benzothien-2-yl)sulfonyl]amino}benzoate

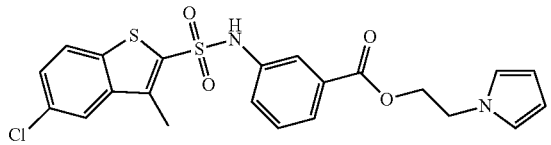 [SMILES: Cc1c(S(=O)(=O)Nc2cccc(C(=O)OCCn3cccc3)c2)sc2ccc(Cl)cc12]

A mixture of 2-pyrrol-1-yl-ethanol (17 mg, 0.15 mmol) and NaH (5 mg, 60% dispersion in mineral oil, 0.13 mmol) in THF (200 µL) was stirred at 0° C. for 15 min. A solution of methyl 3-{[(5-chloro-3-methyl-1-benzothien-2-yl)sulfonyl]amino}benzoate (Example 74) (20 mg, 0.05 mmol) in THF (100 µL) was added, and the reaction mixture was stirred at 0° C. for another 6 h. The reaction was quenched by addition of cold MeOH and 4:1 water/HOAc (50 µL) before purified by preparative HPLC. The title compound was obtained in 53% yield (12.5 mg). MS (ESI+) m/z 475 [M+H]$^+$.

Example 107, General Procedure 7

Ethyl 3-{[(5-chloro-3-methyl-1-benzothien-2-yl)sulfonyl]amino}benzoate

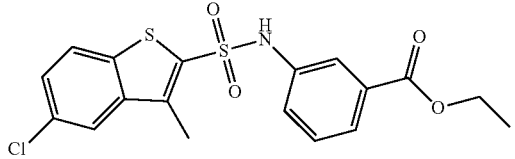 [SMILES: CCOC(=O)c1cccc(NS(=O)(=O)c2sc3ccc(Cl)cc3c2C)c1]

A reaction mixture containing 3-{[(5-chloro-3-methyl-1-benzothien-2-yl)sulfonyl]-amino}benzoic acid (21 mg, 0.055 mmol) (Intermediate 19), 1,1'-carbonyldiimidazole (17 mg, 0.106 mmol) and pyridine (9 µL, 0.113 mmol) in MeCN (0.75 mL) was stirred at 60° C. for 30 min, and then a second portion of pyridine (5 µL, 0.062 mmol) was added. After additional 30 min of stirring at 60° C., EtOH (6 µL, 0.100 mmol) was added. The reaction mixture was stirred at 50° C. over night, and then diluted with DMSO/MeCN/water. TFA (50 µL) was added and the crude product was purified by reversed phase chromatography (ACE C8, 5 µm, 21×50 mm, flow 25 ml/min, gradient: 0.1% TFA in water/MeCN over 6 minutes). The title compound was obtained in 54% yield (12.2 mg). $^1$H NMR (500 MHz, CDCl$_3$) δ ppm 1.34 (t, J=7.08 Hz, 3 H) 2.45 (s, 3 H) 4.33 (q, J=7.08 Hz, 2 H) 6.92 (s, 1 H) 7.36 (dd, J=8.04, 7.66 Hz, 1 H) 7.42 (ddd, J=8.04, 2.32, 1.17 Hz, 1 H) 7.44 (dd, J=8.70, 1.95 Hz, 1 H) 7.71 (d, J=8.70 Hz, 1 H) 7.71 (d, J=1.95 Hz, 1 H) 7.71-7.72 (m, 1 H) 7.84 (ddd, J=7.66, 1.48, 1.17 Hz, 1 H). MS (ESI+) m/z 410 [M+H]$^+$.

Example 108

Isopropyl 3-{[(5-chloro-3-methyl-1-benzothien-2-yl)sulfonyl]amino}benzoate

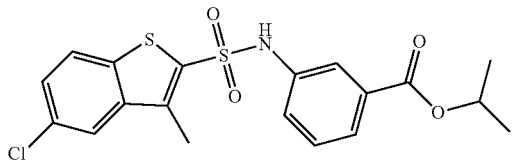 [SMILES: Cc1c(S(=O)(=O)Nc2cccc(C(=O)OC(C)C)c2)sc2ccc(Cl)cc12]

The product was prepared from 3-{[(5-chloro-3-methyl-1-benzothien-2-yl)sulfonyl]amino}benzoic acid (21 mg, 0.055 mmol) (Intermediate 19) and isopropyl alcohol (6.0 mg, 0.100 mmol) according to the General Procedure 7, described in Example 107, using a slightly modified reaction time (2 days). The title compound was obtained in 57% yield (13.3 mg). $^1$H NMR (500 MHz, CDCl$_3$) δ ppm 1.30 (d, J=6.32 Hz, 6 H) 2.45 (s, 3 H) 5.18 (spt, J=6.32 Hz, 1 H) 6.89 (s, 1 H) 7.35 (dd, J=8.06, 7.65 Hz, 1 H) 7.41 (ddd, J=8.06, 2.35, 1.18 Hz, 1 H) 7.44 (dd, J=8.73, 1.94 Hz, 1 H) 7.68 (dd, J=2.35, 1.50 Hz, 1 H) 7.71 (dd, J=8.73, 0.61 Hz, 1 H) 7.71 (dd, J=1.94, 0.61 Hz, 1 H) 7.83 (ddd, J=7.65, 1.50, 1.18 Hz, 1 H). MS (ESI+) m/z 424 [M+H]$^+$.

Example 109

2-Methoxyethyl 3-{[(5-chloro-3-methyl-1-benzothiophen-2-yl)sulfonyl]amino}benzoate

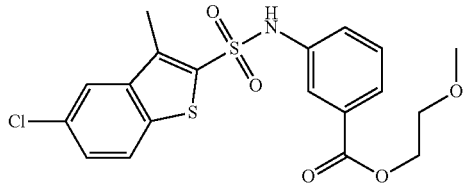 [SMILES: COCCOC(=O)c1cccc(NS(=O)(=O)c2sc3ccc(Cl)cc3c2C)c1]

The product was prepared from 3-{[(5-chloro-3-methyl-1-benzothien-2-yl)sulfonyl]amino}benzoic acid (21 mg, 0.055 mmol) (Intermediate 19) and 2-methoxyethanol (7.6 mg, 0.100 mmol) according to the General Procedure 7, described in Example 107. The title compound was obtained in 70% yield (16.9 mg). $^1$H NMR (500 MHz, CDCl$_3$) δ ppm 2.47 (s, 3 H) 3.40 (s, 3 H) 3.67-3.70 (m, 2 H) 4.42-4.45 (m, 2 H) 6.92 (s, 1 H) 7.37 (dd, J=8.02, 7.74 Hz, 1 H) 7.45 (dd, J=8.73, 1.96 Hz, 1 H) 7.45 (ddd, J=8.02, 2.34, 1.17 Hz, 1 H) 7.72 (dd, J=8.73, 0.60 Hz, 1 H) 7.72 (dd, J=1.96, 0.60 Hz, 1 H) 7.74 (dd, J=2.34, 1.59 Hz, 1 H) 7.87 (ddd, J=7.74, 1.59, 1.17 Hz, 1 H). MS (ESI+) m/z 440 [M+H]$^+$.

Example 110

Butyl 3-{[(5-chloro-3-methyl-1-benzothiophen-2-yl)sulfonyl]amino}benzoate

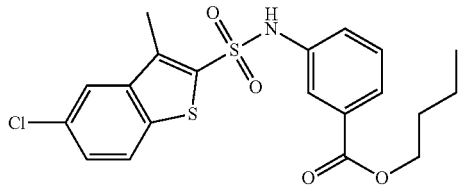 [SMILES: CCCCOC(=O)c1cccc(NS(=O)(=O)c2sc3ccc(Cl)cc3c2C)c1]

The product was prepared from 3-{[(5-chloro-3-methyl-1-benzothien-2-yl)sulfonyl]amino}benzoic acid (21 mg, 0.055 mmol) (Intermediate 19) and 1-butanol (7.4 mg, 0.100 mmol) according to the General Procedure 7, described in Example 107. The title compound was obtained in 77% yield (18.5 mg). $^1$H NMR (500 MHz, CDCl$_3$) δ ppm 0.95 (t, J=7.39 Hz, 3 H) 1.37-1.46 (m, 2 H) 1.65-1.72 (m, 2 H) 2.44 (s, 3 H) 4.27 (t, J=6.65 Hz, 2H) 6.88 (s, 1 H) 7.36 (dd, J=8.06, 7.67 Hz, 1 H) 7.42 (ddd, J=8.06, 2.32, 1.22 Hz, 1 H) 7.45 (dd, J=8.67, 1.95 Hz, 1 H) 7.71 (dd, J=8.67, 0.52 Hz, 1 H) 7.70-7.71 (m, 1 H) 7.71 (dd, J=1.95, 0.52 Hz, 1 H) 7.84 (ddd, J=7.67, 1.50, 1.21 Hz, 1 H). MS (ESI+) m/z 438 [M+H]$^+$.

Example 111

Benzyl 3-{[(5-chloro-3-methyl-1-benzothiophen-2-yl)sulfonyl]amino}benzoate

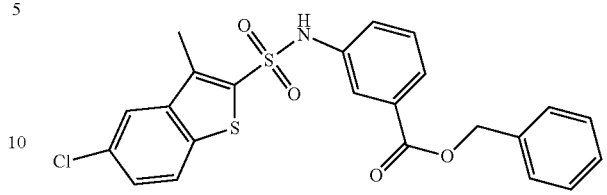

The product was prepared from 3-{[(5-chloro-3-methyl-1-benzothien-2-yl)sulfonyl]amino}benzoic acid (21 mg, 0.055 mmol) (Intermediate 19) and benzyl alcohol (10.8 mg, 0.100 mmol) according to the General Procedure 7, described in Example 107, using a slightly modified reaction time (2 days). The title compound was obtained in 68% yield (17.6 mg). $^1$H NMR (500 MHz, CDCl$_3$) δ ppm 2.44 (s, 3 H) 5.31 (s, 2 H) 6.96 (s, 1 H) 7.33-7.40 (m, 5 H) 7.36 (dd, J=8.05, 7.70 Hz, 1 H) 7.43 (ddd, J=8.05, 2.36, 1.20 Hz, 1 H) 7.43 (dd, J=8.63, 2.06 Hz, 1 H) 7.68 (dd, J=8.63, 0.58 Hz, 1 H) 7.69 (dd, J=2.06, 0.58 Hz, 1 H) 7.74 (dd, J=2.36, 1.58 Hz, 1 H) 7.86 (ddd, J=7.70, 1.58, 1.20 Hz, 1 H). MS (ESI+) m/z 472 [M+H]$^+$.

EXAMPLE 112

Propyl 3-{[(5-chloro-3-methyl-1-benzothien-2-yl)sulfonyl]amino}benzoate

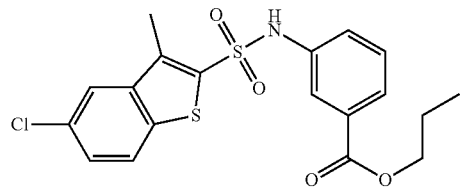 [SMILES: CCCOC(=O)c1cccc(NS(=O)(=O)c2sc3ccc(Cl)cc3c2C)c1]

The product was prepared from 3-{[(5-chloro-3-methyl-1-benzothien-2-yl)sulfonyl]amino}benzoic acid (21 mg, 0.055 mmol) (Intermediate 19) and 1-propanol (6.0 mg, 0.100 mmol) according to the General Procedure 7, described in Example 107. The title compound was obtained in 75% yield (17.6 mg). $^1$H NMR (500 MHz, CDCl$_3$) δ ppm 0.97 (t, J=7.45 Hz, 3 H) 1.68-1.77 (m, 2 H) 2.44 (s, 3 H) 4.23 (t, J=6.65 Hz, 2 H) 6.90 (s, 1 H) 7.36 (dd, J=8.05, 7.70 Hz, 1 H) 7.42 (ddd, J=8.05, 2.34, 1.22 Hz, 1 H) 7.44 (dd, J=8.73, 1.95 Hz, 1H) 7.71 (dd, J=8.73, 0.60 Hz, 1 H) 7.71 (dd, J=1.95, 0.60 Hz, 1 H) 7.71 (dd, J=2.34, 1.53 Hz, 1 H) 7.84 (ddd, J=7.70, 1.53, 1.22 Hz, 1 H). MS (ESI+) m/z 424 [M+H]$^+$.

EXAMPLE 113

Pentyl 3-{[(5-chloro-3-methyl-1-benzothiophen-2-yl)sulfonyl]amino}benzoate

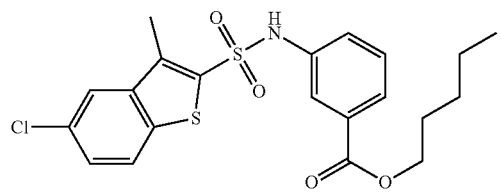 [SMILES: CCCCCOC(=O)c1cccc(NS(=O)(=O)c2sc3ccc(Cl)cc3c2C)c1]

The product was prepared from 3-{[(5-chloro-3-methyl-1-benzothien-2-yl)sulfonyl]amino}benzoic acid (21 mg, 0.055 mmol) (Intermediate 19) and 1-pentanol (8.8 mg, 0.100 mmol) according to the General Procedure 7, described in Example 107. The title compound was obtained in 76% yield (18.8 mg). $^1$H NMR (500 MHz, CDCl$_3$) δ ppm 0.89-0.95 (m, 3 H) 1.32-1.42 (m, 4 H) 1.67-1.75 (m, 2 H) 2.45 (s, 3 H) 4.26 (t, J=6.77 Hz, 2 H) 6.87 (s, 1 H) 7.36 (dd, J=8.10, 7.63 Hz, 1 H) 7.42 (ddd, J=8.10, 2.36, 1.25 Hz, 1 H) 7.44 (dd, J=8.70, 1.95 Hz, 1 H) 7.69-7.73 (m, 3 H) 7.84 (ddd, J=7.63, 1.50, 1.25 Hz, 1 H). MS (ESI+) m/z 452 [M+H]$^+$.

EXAMPLE 114

Hexyl 3-{[(5-chloro-3-methyl-1-benzothiophen-2-yl)sulfonyl]amino}benzoate

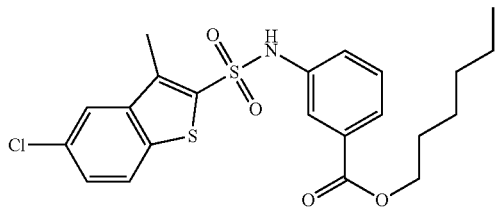 [SMILES: CCCCCCOC(=O)c1cccc(NS(=O)(=O)c2sc3ccc(Cl)cc3c2C)c1]

The product was prepared from 3-{[(5-chloro-3-methyl-1-benzothien-2-yl)sulfonyl]amino}benzoic acid (21 mg, 0.055 mmol) (Intermediate 19) and 1-hexanol (10.2 mg, 0.100 mmol) according to the General Procedure 7, described in Example 107. The title compound was obtained in 71% yield (18.3 mg). $^1$H NMR (500 MHz, CDCl$_3$) δ ppm 0.87-0.93 (m, 3 H) 1.27-1.36 (m, 4 H) 1.35-1.43 (m, 2 H) 1.65-1.74 (m, 2 H) 2.45 (s, 3 H) 4.26 (t, J=6.71 Hz, 2 H) 6.85 (s, 1 H) 7.36 (dd, J=8.08, 7.68 Hz, 1 H) 7.42 (ddd, J=8.08, 2.35, 1.28 Hz, 1 H) 7.44 (dd, J=8.69, 1.95 Hz, 1 H) 7.71 (dd, J=8.69, 0.55 Hz, 1 H) 7.71-7.72 (m, 1 H) 7.71 (dd, J=1.95, 0.55 Hz, 1 H) 7.84 (ddd, J=7.68, 1.50, 1.28 Hz, 1 H). MS (ESI+) m/z 466 [M+H]$^+$.

EXAMPLE 115

Phenyl 3-{[(5-chloro-3-methyl-1-benzothiophen-2-yl)sulfonyl]amino}benzoate

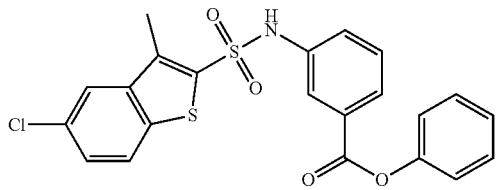 [SMILES: Cc1c(S(=O)(=O)Nc2cccc(C(=O)Oc3ccccc3)c2)sc2ccc(Cl)cc12]

The product was prepared from 3-{[(5-chloro-3-methyl-1-benzothien-2-yl)sulfonyl]amino}benzoic acid (21 mg, 0.055 mmol) (Intermediate 19) and phenol (9.4 mg, 0.100 mmol) according to the General Procedure 7, described in Example 107. The title compound was obtained in 74% yield (18.7 mg). $^1$H NMR (500 MHz, CDCl$_3$) δ ppm 2.50 (s, 3 H) 7.06 (s, 1 H) 7.10-7.15 (m, 2 H) 7.25-7.29 (m, 1 H) 7.39-7.44 (m, 2 H) 7.44 (dd, J=8.10, 7.70 Hz, 1 H) 7.44 (dd, J=8.65, 2.02 Hz, 1 H) 7.51 (ddd, J=8.10, 2.34, 1.15 Hz, 1 H) 7.72 (dd, J=8.65, 0.57 Hz, 1 H) 7.73 (dd, J=2.02, 0.57 Hz, 1 H) 7.86 (dd, J=2.34, 1.58 Hz, 1H) 7.99 (ddd, J=7.70, 1.58, 1.15 Hz, 1 H). MS (ESI+) m/z 458 [M+H]$^+$.

EXAMPLE 116

Tetrahydrofuran-3-yl 3-{[(5-chloro-3-methyl-1-benzothiophen-2-yl)sulfonyl]amino}benzoate

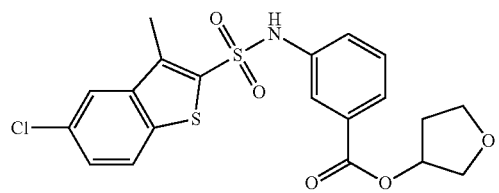 [SMILES: Cc1c(S(=O)(=O)Nc2cccc(C(=O)OC3CCOC3)c2)sc2ccc(Cl)cc12]

The product was prepared from 3-{[(5-chloro-3-methyl-1-benzothien-2-yl)sulfonyl]amino}benzoic acid (21 mg, 0.055 mmol) (Intermediate 19) and 3-hydroxytetrahydrofuran (8.8 mg, 0.100 mmol) according to the General Procedure 7, described in Example 107. The title compound was obtained in 63% yield (15.6 mg). $^1$H NMR (500 MHz, CDCl$_3$) δ ppm 2.07 (ddddd, J=13.81, 6.79, 4.51, 1.93, 1.05 Hz, 1 H) 2.25 (dddd, J=13.81, 8.43, 8.43, 6.32 Hz, 1 H) 2.47 (s, 3 H) 3.86-3.96 (m, 3 H) 3.97 (dd, J=10.65, 4.64 Hz, 1 H) 5.46-5.50 (m, 1 H) 7.00 (s, 1 H) 7.37 (dd, J=8.05, 7.69 Hz, 1 H) 7.44 (ddd, J=8.05, 2.35, 1.17 Hz, 1 H) 7.44 (dd, J=8.72, 1.95 Hz, 1 H) 7.70 (dd, J=2.35, 1.57 Hz, 1 H) 7.72 (dd, J=8.72, 0.57 Hz, 1 H) 7.72 (dd, J=1.95, 0.57 Hz, 1 H) 7.82 (ddd, J=7.69, 1.57, 1.17 Hz, 1 H). MS (ESI+) m/z 452 [M+H]$^+$.

EXAMPLE 117

Tetrahydrofuran-3-ylmethyl 3-{[(5-chloro-3-methyl-1-benzothiophen-2-yl)sulfonyl]amino}benzoate

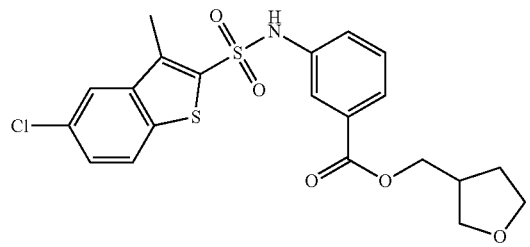 [SMILES: Cc1c(S(=O)(=O)Nc2cccc(C(=O)OCC3CCOC3)c2)sc2ccc(Cl)cc12]

The product was prepared from 3-{[(5-chloro-3-methyl-1-benzothien-2-yl)sulfonyl]amino}benzoic acid (21 mg, 0.055 mmol) (Intermediate 19) and 3-hydroxymethyltetrahydrofuran (10.2 mg, 0.100 mmol) according to the General Procedure 7, described in Example 107. The title compound was obtained in 64% yield (16.5 mg). $^1$H NMR (500 MHz, CDCl$_3$) δ ppm 1.67 (dddd, J=12.56, 7.90, 7.00, 5.96 Hz, 1 H) 2.06 (dddd, J=12.56, 8.61, 7.70, 5.54 Hz, 1 H) 2.45 (s, 3 H) 2.61-2.70 (m, 1 H) 3.62 (dd, J=8.86, 5.45 Hz, 1 H) 3.77 (ddd, J=8.61, 7.70, 7.00 Hz, 1 H) 3.86 (dd, J=8.86, 7.06 Hz, 1 H) 3.88 (ddd, J=8.61, 7.90, 5.54 Hz, 1 H) 4.19 (dd, J=10.89, 7.81 Hz, 1 H) 4.28 (dd, J=10.89, 6.49 Hz, 1 H) 7.02 (s, 1 H) 7.37 (dd, J=8.00, 7.66 Hz, 1 H) 7.43 (ddd, J=8.06, 2.32, 1.22 Hz, 1 H) 7.44 (dd, J=8.67, 1.95 Hz, 1 H) 7.72 (dd, J=8.67, 0.53 Hz, 1 H) 7.71 (dd, J=1.95, 0.53 Hz, 1 H) 7.71-7.72 (m, 1 H) 7.82 (ddd, J=7.66, 1.55, 1.22 Hz, 1 H). MS (ESI+) m/z 466 [M+H]+.

EXAMPLE 118

3-(Dimethylamino)propyl 3-{[(5-chloro-3-methyl-1-benzothiophen-2-yl)sulfonyl]amino}benzoate

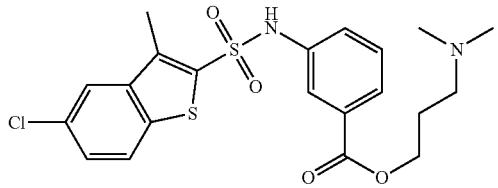 [SMILES: Cc1c(S(=O)(=O)Nc2cccc(C(=O)OCCCN(C)C)c2)sc2ccc(Cl)cc12]

The product was prepared from 3-{[(5-chloro-3-methyl-1-benzothien-2-yl)sulfonyl]amino}benzoic acid (21 mg, 0.055 mmol) (Intermediate 19) and 3-dimethylamino-1-propanol (10.3 mg, 0.100 mmol) according to the General Procedure 7, described in Example 107. The title compound was obtained in 99% yield (25.5 mg). $^1$H NMR (500 MHz, CDCl$_3$) δ ppm 2.19-2.27 (m, 2 H) 2.53 (s, 3 H) 2.86 (s, 6 H) 3.19-3.25 (m, 2 H) 4.30-4.36 (m, 2 H) 7.35 (dd, J=8.12, 7.78 Hz, 1 H) 7.42 (dd, J=8.67, 2.05 Hz, 1 H) 7.56 (ddd, J=8.12, 2.34, 1.05 Hz, 1 H) 7.70 (dd, J=8.67, 0.57 Hz, 1 H) 7.71 (dd, J=2.05, 0.57 Hz, 1H) 7.75 (ddd, J=7.78, 1.60, 1.05 Hz, 1 H) 7.89 (dd, J=2.34, 1.60 Hz, 1 H) 8.38 (br. s., 1 H). MS (ESI+) m/z 467 [M+H]+.

Example 119

General Procedure 8

Methyl {5-[3-({[3-methyl-5-(1-methylethyl)-1-benzothiophen-2-yl]sulfonyl}amino)phenyl]-2H-tetrazol-2-yl}acetate

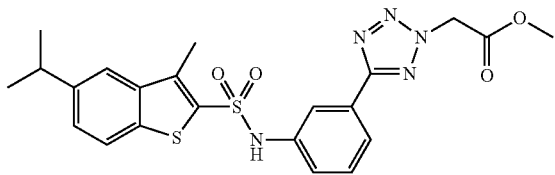 [SMILES: COC(=O)Cn1nnc(-c2cccc(NS(=O)(=O)c3sc4ccc(C(C)C)cc4c3C)c2)n1]

A reaction mixture containing [5-(3-{[(5-isopropyl-3-methyl-1-benzothien-2-yl)sulfonyl]-amino}phenyl)-2H-tetrazol-2-yl]acetic acid (5.7 mg, 0.012 mmol) (Example 12), 1,1'-carbonyldiimidazole (4.0 mg, 0.025 mmol) and pyridine (5.0 μL, 0.062 mmol) in MeCN (0.60 mL) was stirred at room temperature for 25 min. MeOH (50 μL, 1.23 mmol) was added. The reaction mixture was stirred at room temperature over night, and then diluted with DMSO/MeOH/water. TFA was added and the crude product was purified by reversed phase chromatography (ACE C8, 5 μm, 21×50 mm, flow 25 ml/min, 0.1% TFA in water/MeCN over 6 minutes). The title compound was obtained in 72% yield (4.2 mg). $^1$H NMR (500 MHz, CDCl$_3$) δ ppm 1.28 (d, J=6.92 Hz, 6 H) 2.53 (s, 3 H) 3.02 (spt, J=6.92 Hz, 1 H) 3.82 (s, 3 H) 5.44 (s, 2 H) 6.92 (s, 1 H) 7.35 (ddd, J=8.11, 2.16, 1.28 Hz, 1 H) 7.35-7.38 (m, 1 H) 7.39 (dd, J=8.11, 7.50 Hz, 1 H) 7.53-7.55 (m, 1 H) 7.70 (d, J=8.42 Hz, 1 H) 7.90 (dd, J=2.16, 1.50 Hz, 1 H) 7.93 (ddd, J=7.50, 1.50, 1.28 Hz, 1 H). MS (ESI+) m/z 486 [M+H]+.

EXAMPLE 120

Methyl 3-{[(5-bromo-3-methyl-1-benzothiophen-2-yl)sulfonyl]amino}benzoate

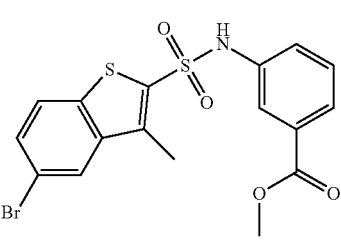 [SMILES: COC(=O)c1cccc(NS(=O)(=O)c2sc3ccc(Br)cc3c2C)c1]

The product was prepared from 3-{[(5-bromo-3-methyl-1-benzothien-2-yl)sulfonyl]-amino}benzoic acid (20.4 mg, 0.048 mmol) (Example 41) and MeOH (50 μL, 1.23 mmol) according to the General Procedure 8, described in Example 119, using different amounts of pyridine (7.5 μL, 0.092 mmol) and a slightly modified reaction volume (0.80 mL). The title compound was obtained in 47% yield (9.9 mg). $^1$H NMR (500 MHz, CDCl$_3$) δ ppm 2.44 (s, 3H) 3.87 (s, 3 H) 6.94 (s, 1 H) 7.36 (dd, J=8.10, 7.66 Hz, 1 H) 7.41 (ddd, J=8.10, 2.35, 1.26 Hz, 1 H) 7.57 (dd, J=8.63, 1.86 Hz, 1 H) 7.66 (dd, J=8.63, 0.54 Hz, 1 H) 7.73 (dd, J=2.35, 1.51 Hz, 1 H) 7.84 (ddd, J=7.66, 1.51, 1.26 Hz, 1 H) 7.87 (dd, J=1.86, 0.54 Hz, 1 H). MS (ESI+) m/z 440 [M+H]+.

EXAMPLE 121

Methyl 3-{[(7-methoxy-3-methyl-1-benzothiophen-2-yl)sulfonyl]amino}benzoate

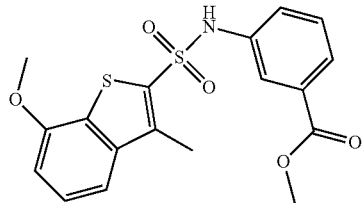 [SMILES: COC(=O)c1cccc(NS(=O)(=O)c2sc3c(OC)cccc3c2C)c1]

The product was prepared from 3-{[(7-methoxy-3-methyl-1-benzothien-2-yl)sulfonyl]amino}benzoic acid (6.8 mg, 0.018 mmol) (Example 42) and MeOH (50 μL, 1.23 mmol) according to the General Procedure 8, described in Example 119. The title compound was obtained in 71% yield (5.0 mg). $^1$H NMR (500 MHz, CDCl$_3$:DMSO-d$_6$ 6:1) δ ppm 2.23 (s, 3 H) 3.56 (s, 3 H) 3.68 (s, 3 H) 6.60 (dd, J=7.54, 1.10 Hz, 1 H) 6.98 (dd, J=8.13, 7.73 Hz, 1H) 7.05 (dd, J=8.17, 1.10 Hz, 1 H) 7.09 (dd, J=8.17, 7.54 Hz, 1 H) 7.14 (ddd, J=8.13, 2.32, 1.09 Hz, 1 H) 7.38 (ddd, J=7.73, 1.63, 1.09 Hz, 1 H) 7.57 (dd, J=2.32, 1.63 Hz, 1 H) 10.18 (s, 1 H). MS (ESI+) m/z 392 [M+H]+.

EXAMPLE 122

Methyl 3-{[(7-chloro-3-methyl-1-benzothiophen-2-yl)sulfonyl]amino}benzoate

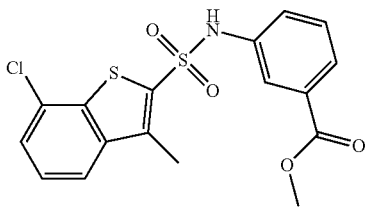 [SMILES: COC(=O)c1cccc(NS(=O)(=O)c2sc3c(Cl)cccc3c2C)c1]

The product was prepared from 3-{[(7-chloro-3-methyl-1-benzothien-2-yl)sulfonyl]amino}benzoic acid (9.2 mg, 0.024 mmol) (Example 44) and MeOH (50 μL, 1.23 mmol) according to the General Procedure 8, described in Example 119, using a different amount of 1,1'-carbonyldiimidazole (10.0 mg, 0.0621 mmol). The title compound was obtained in 74% yield (7.0 mg). $^1$H NMR (500 MHz, CDCl$_3$) δ ppm 2.46 (s, 3 H) 3.87 (s, 3 H) 6.79 (s, 1 H) 7.37 (dd, J=8.06, 7.70 Hz, 1 H) 7.41 (dd, J=8.06, 7.69 Hz, 1 H) 7.43 (ddd, J=8.06, 2.32, 1.21 Hz, 1 H) 7.48 (dd, J=7.69, 0.98 Hz, 1 H) 7.65 (dd, J=8.06, 0.98 Hz, 1 H) 7.74 (dd, J=2.32, 1.51 Hz, 1 H) 7.84 (ddd, J=7.70, 1.51, 1.21 Hz, 1 H). MS (ESI+) m/z 396 [M+H]$^+$.

EXAMPLE 123

General Procedure 9

Methyl 3-({[3-methyl-5-(1-methylethyl)-1-benzofuran-2-yl]sulfonyl}amino)benzoate

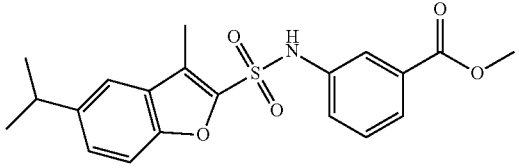 [SMILES: COC(=O)c1cccc(NS(=O)(=O)c2oc3ccc(C(C)C)cc3c2C)c1]

A mixture of methyl 4-aminobenzoate (16 mg, 0.106 mmol), 5-isopropyl-3-methylbenzofuran-2-sulfonyl chloride (Intermediate 16) (40 mg, 0.147 mmol) and pyridine (20 μL, 0.25 mmol) in MeCN (600 μL) was stirred at 50° C. overnight. The reaction mixture was diluted with MeOH/water and acidified by addition of TFA. The crude product was purified by reversed phase chromatography (ACE C8, 5 μm, 21×50 mm, flow 25 ml/min, 0.1% TFA in water/MeCN over 6 minutes). The title compound was obtained in 17% yield (6.7 mg). $^1$H NMR (500 MHz, MeOH-d$_4$) δ ppm 1.28 (d, J=6.96 Hz, 6 H) 2.41 (s, 3 H) 3.02 (spt, J=6.96 Hz, 1 H) 3.85 (s, 3 H) 7.31-7.37 (m, 2 H) 7.37 (dd, J=8.67, 1.68 Hz, 1 H) 7.40 (dd, J=8.67, 0.75 Hz, 1 H) 7.46 (dt, J=1.68, 0.75 Hz, 1 H) 7.69-7.73 (m, 1 H) 7.82-7.84 (m, 1H). MS (ESI+) m/z 388 [M+H]$^+$.

EXAMPLE 124

Methyl 2-({[3-methyl-5-(1-methylethyl)-1-benzothiophen-2-yl]sulfonyl}amino)-1,3-thiazole-5-carboxylate

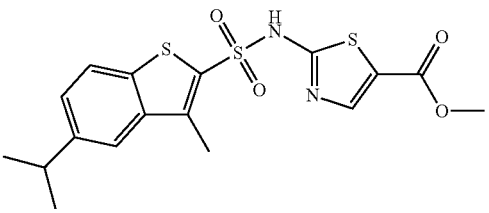 [SMILES: COC(=O)c1cnc(NS(=O)(=O)c2sc3ccc(C(C)C)cc3c2C)s1]

The product was prepared from methyl 2-aminothiazole-5-carboxylate (8 mg, 0.050 mmol) and 5-isopropyl-3-methylbenzothiophene-2-sulfonyl chloride (Intermediate 2) (14 mg, 0.050 mmol) according to the General Procedure 9, described in Example 123, using a slightly modified reaction temperature of 60° C. and a reaction time of three days. The title compound was obtained in 32% yield (6 mg). $^1$H NMR (500 MHz, CDCl$_3$) δ ppm 1.31 (d, J=6.84 Hz, 6 H) 2.68 (s, 3 H) 3.05 (spt, J=6.84 Hz, 1 H) 3.87 (s, 3 H) 7.38 (dd, J=8.42, 1.71 Hz, 1 H) 7.60 (dt, J=1.71, 0.61 Hz, 1 H) 7.70 (d, J=8.42 Hz, 1 H) 7.84 (s, 1 H). MS (ESI+) m/z 411 [M+H]$^+$.

EXAMPLE 125

Ethyl 4-methyl-2-({[3-methyl-5-(1-methylethyl)-1-benzothiophen-2-yl]sulfonyl}amino)-1,3-thiazole-5-carboxylate

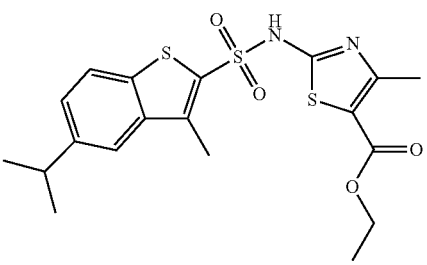 [SMILES: CCOC(=O)c1sc(NS(=O)(=O)c2sc3ccc(C(C)C)cc3c2C)nc1C]

The product was prepared from ethyl 2-amino-4-methyl-1,3-thiazole-5-carboxylate (9 mg, 0.050 mmol) and 5-isopropyl-3-methylbenzothiophene-2-sulfonyl chloride (Intermediate 2) (14 mg, 0.050 mmol) according to the General Procedure 9, described in Example 123, using a slightly modified reaction temperature of 60° C. and a reaction time of three days. The title compound was obtained in 48% yield (11 mg). $^1$H NMR (500 MHz, CDCl$_3$) δ ppm 1.31 (d, J=6.96 Hz, 6 H) 1.34 (t, J=7.16 Hz, 3 H) 2.65 (s, 3 H) 2.65 (s, 3 H) 3.05 (spt, J=6.96 Hz, 1 H) 4.29 (q, J=7.16 Hz, 2 H) 7.35 (dd, J=8.42, 1.71 Hz, 1 H) 7.56 (dt, J=1.71, 0.59 Hz, 1 H) 7.62 (d, J=8.42 Hz, 1 H) 11.06 (br. s., 1 H). MS (ESI+) m/z 439 [M+H]$^+$.

EXAMPLE 126

Ethyl 2-{[(5-chloro-3-methyl-1-benzothiophen-2-yl)sulfonyl]amino}-4-methyl-1,3-thiazole-5-carboxylate

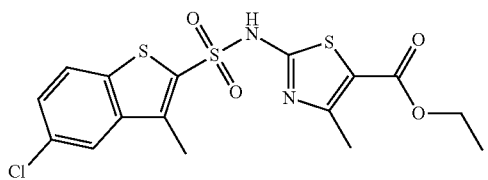 [SMILES: CCOC(=O)c1sc(NS(=O)(=O)c2sc3ccc(Cl)cc3c2C)nc1C]

The product was prepared from ethyl 2-amino-4-methyl-1,3-thiazole-5-carboxylate (9 mg, 0.050 mmol) and 5-chloro-3-methylbenzothiophene-2-sulfonyl chloride (14 mg, 0.050 mmol) according to the General Procedure 9, described in Example 123, using a slightly modified reaction temperature of 60° C. and a reaction time of one week. The title compound was obtained in 18% yield (3.9 mg). $^1$H NMR (500 MHz, CDCl$_3$) δ ppm 1.34 (t, J=7.15 Hz, 3 H) 2.60 (s, 3 H) 2.61 (s, 3 H) 4.30 (q, J=7.15 Hz, 2 H) 7.42 (dd, J=8.63, 2.01 Hz, 1 H) 7.66 (dd, J=8.63, 0.50 Hz, 1 H) 7.70 (dd, J=2.01, 0.50 Hz, 1 H). MS (ESI+) m/z 431 [M+H]$^+$.

EXAMPLE 127

Ethyl 2-({[5-chloro-4-(2,5-difluorophenyl)thiophen-2-yl]sulfonyl}amino)-4-methyl-1,3-thiazole-5-carboxylate

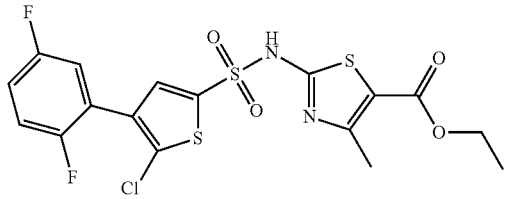 [SMILES: CCOC(=O)c1sc(NS(=O)(=O)c2cc(-c3cc(F)ccc3F)c(Cl)s2)nc1C]

The product was prepared from ethyl 2-amino-4-methyl-1,3-thiazole-5-carboxylate (9 mg, 0.050 mmol) and 5-chloro-4-(2,5-difluorophenyl)thiophene-2-sulfonyl chloride (Intermediate 20) (17 mg, 0.050 mmol) according to the General Procedure 9, described in Example 123, using a slightly modified reaction temperature of 60° C. and a reaction time of one week. The title compound was obtained in 20% yield (4.7 mg). $^1$H NMR (500 MHz, CDCl$_3$) δ ppm 1.36 (t, J=7.11 Hz, 3 H) 2.62 (s, 3 H) 4.32 (q, J=7.11 Hz, 2 H) 7.05-7.11 (m, 1 H) 7.13 (td, J=9.02, 4.63 Hz, 1 H) 7.16 (ddd, J=8.55, 5.62, 3.07 Hz, 1 H) 7.60 (d, J=1.83 Hz, 1 H). MS (ESI+) m/z 479 [M+H]$^+$.

EXAMPLE 128

General Procedure 10

2-{[(5-Chloro-3-methyl-1-benzothiophen-2-yl)sulfonyl]amino}-4-methyl-1,3-thiazole-5-carboxylic acid

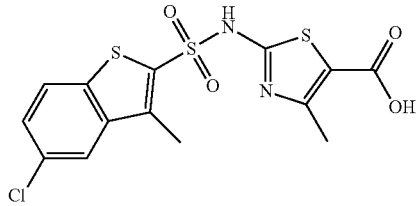 [SMILES: Cc1nc(NS(=O)(=O)c2sc3ccc(Cl)cc3c2C)sc1C(=O)O]

A mixture of ethyl 2-amino-4-methylthiazole-5-carboxylate (9.3 mg, 0.050 mmol), 5-chloro-3-methyl-benzothiophene-2-sulfonyl chloride (14 mg, 0.050 mmol) and pyridine (8 μL, 0.100 mmol) in MeCN (400 μL) was heated at 60° C. for 7 days. The solvent was removed and the residue redissolved in 1 M NaOH (300 μL, 0.300 mmol) and then heated at 60° C. over night. The crude product was diluted with water/MeOH/DMSO and acidified by addition of TFA. The product was purified by reversed phase chromatography (ACE C8, 5 μm, 21×50 mm, flow 25 ml/min, gradient: 0.1% TFA in water/MeCN over 6 minutes). The title compound was obtained in 24% yield (4.9 mg). $^1$H NMR (500 MHz, MeOH-d$_4$) δ ppm 2.47 (s, 3 H) 2.65 (s, 3H) 7.47 (dd, J=8.67, 2.08 Hz, 1 H) 7.88 (dd, J=8.67, 0.51 Hz, 1 H) 7.89 (dd, J=2.08, 0.51 Hz, 1 H). MS (ESI+) m/z 403 [M+H]$^+$.

EXAMPLE 129

2-({[5-Chloro-4-(2,5-difluorophenyl)thiophen-2-yl]sulfonyl}amino)-4-methyl-1,3-thiazole-5-carboxylic acid

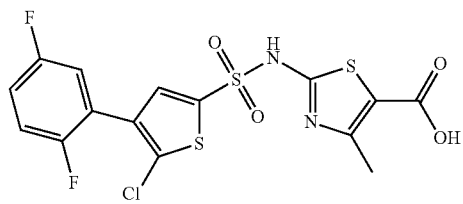 [SMILES: Cc1nc(NS(=O)(=O)c2cc(-c3cc(F)ccc3F)c(Cl)s2)sc1C(=O)O]

The product was prepared from ethyl 2-amino-4-methylthiazole-5-carboxylate (9.3 mg, 0.050 mmol) and 5-chloro-4-(2,5-difluorophenyl)thiophene-2-sulfonyl chloride (Intermediate 20) (17 mg, 0.050 mmol) according to the General Procedure 10, described in Example 128. The title compound was obtained in 17% yield (3.9 mg). $^1$H NMR (500 MHz, MeOH-d$_4$) δ ppm 2.50 (s, 3 H) 7.18-7.23 (dddd, J=9.16, 7.57, 3.91, 3.05 Hz, 1 H) 7.26 (td, J=9.16, 4.60 Hz, 1H) 7.26 (ddd, J=8.70, 5.70, 3.05 Hz, 1 H) 7.57 (d, J=1.71 Hz, 1 H). MS (ESI+) m/z 451 [M+H]$^+$.

EXAMPLE 130

2-{[(5-Chloro-3-methyl-1-benzothiophen-2-yl)sulfonyl]amino}-1,3-thiazole-5-carboxylic acid

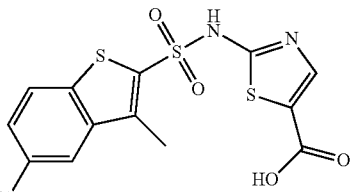

The product was prepared from methyl 2-amino-1,3-thiazole-5-carboxylate (7.9 mg, 0.050 mmol) and 5-chloro-3-methyl-benzothiophene-2-sulfonyl chloride (14 mg, 0.050 mmol) according to the General Procedure 10, described in Example 128. The title compound was obtained in 35% yield (6.8 mg). $^1$H NMR (500 MHz, MeOH-d$_4$) δ ppm 2.65 (s, 3 H 7.47 (dd, J=8.67, 2.08 Hz, 1 H) 7.80 (s, 1 H) 7.88 (dd, J=8.67, 0.57 Hz, 1 H) 7.90 (dd, J=2.08, 0.57 Hz, 1 H). MS (ESI+) m/z 389 [M+H]⁺.

EXAMPLE 131

General Procedure 11

2-({[5-(3,5-Difluorophenyl)thiophen-2-yl]sulfonyl}amino)-5-methyl-1,3-thiazole-4-carboxylic acid

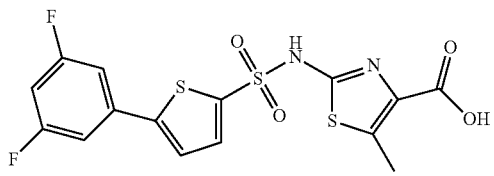 [SMILES: Cc1sc(NS(=O)(=O)c2ccc(-c3cc(F)cc(F)c3)s2)nc1C(=O)O]

A solution of methyl 2-amino-5-methyl-1,3-thiazole-4-carboxylate (25 mg, 0.15 mmol), 5-(3,5-difluorophenyl)thiophene-2-sulfonyl chloride (43 mg, 0.15 mmol) (Intermediate 21) and pyridine (23 mg, 0.29 mmol) in MeCN (1 mL) was stirred at 50° C. for 2 days. After evaporation of the solvents, the residue was dissolved in THF (1 mL) and 2 M LiOH (1 mL) was added. The reaction mixture was stirred at room temperature over night. The reaction mixture was neutralized with 4 M HCl (0.3 mL) and the solvents were removed by evaporation. The crude material was dissolved in MeCN/water (1:1). The product precipitated and the title compound was obtained in 9% yield (5.8 mg). ¹H NMR (400 MHz, MeOH-d₄) δ ppm 2.56 (s, 3 H) 6.97 (tt, J=9.05, 2.27 Hz, 1 H) 7.26-7.34 (m, 2 H) 7.45 (d, J=3.91 Hz, 1 H) 7.58 (d, J=3.91 Hz, 1 H). MS (ESI+) m/z 417 [M+H]⁺.

EXAMPLE 132

2-({[5-Chloro-4-(2,5-difluorophenyl)thiophen-2-yl]sulfonyl}amino)-5-methyl-1,3-thiazole-4-carboxylic acid

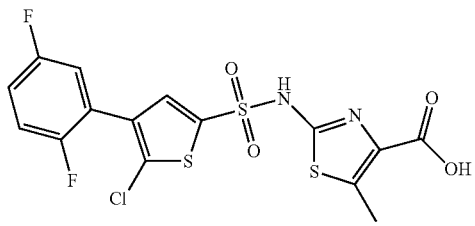 [SMILES: Cc1sc(NS(=O)(=O)c2cc(-c3cc(F)ccc3F)c(Cl)s2)nc1C(=O)O]

The product was prepared from methyl 2-amino-5-methyl-1,3-thiazole-4-carboxylate (25 mg, 0.15 mmol), and 5-chloro-4-(2,5-difluorophenyl)thiophene-2-sulfonyl chloride (Intermediate 20) (48 mg, 0.15 mmol) according to the General Procedure 11, described in Example 131. The crude product was purified using reversed phase chromatography (ACE C8, 5 μm, 21×50 mm, flow 25 ml/min, gradient: H₂0.1% TFA in water/MeCN over 6 minutes). The title compound was obtained in 21% yield (14.1 mg). ¹H NMR (400 MHz, MeOH-d₄) δ ppm 2.56 (s, 3 H) 7.17-7.30 (m, 3 H) 7.55 (d, J=1.76 Hz, 1 H). MS (ESI+) m/z 451 [M+H]⁺.

EXAMPLE 133

5-Methyl-2-({[3-methyl-5-(1-methylethyl)-1-benzothiophen-2-yl]sulfonyl}amino)-1,3-thiazole-4-carboxylic acid

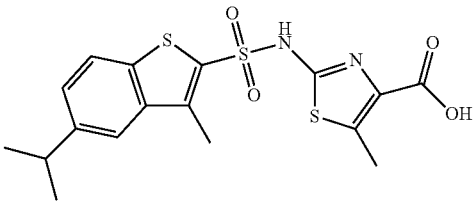 [SMILES: Cc1sc(NS(=O)(=O)c2sc3ccc(C(C)C)cc3c2C)nc1C(=O)O]

The product was prepared from methyl 2-amino-5-methyl-1,3-thiazole-4-carboxylate (25 mg, 0.15 mmol) and 5-isopropyl-3-methylbenzothiophene-2-sulfonyl chloride (42 mg, 0.15 mmol) (Intermediate 2) according to the General Procedure 11, described in Example 131. The crude product was purified using reversed phase chromatography (ACE C8, 5 μm, 21×50 mm, flow 25 ml/min, gradient: 0.1% TFA in water/MeCN over 6 minutes). The title compound was obtained in 6% yield (3.6 mg). ¹H NMR (400 MHz, MeOH-d₄) δ ppm 1.32 (d, J=6.98 Hz, 6 H) 2.53 (s, 3 H) 2.66 (s, 3 H) 3.06 (spt, J=6.98 Hz, 1 H) 7.41 (ddd, J=8.41, 1.72, 0.40 Hz, 1 H) 7.68 (dt, J=1.72, 0.60 Hz, 1 H) 7.77 (dd, J=8.41, 0.60 Hz, 1 H). MS (ESI+) m/z 411 [M+H]⁺.

EXAMPLE 134

3-{[(5-Chloro-3-methyl-1-benzothiophen-2-yl)sulfonyl]amino}-2-hydroxybenzoic acid

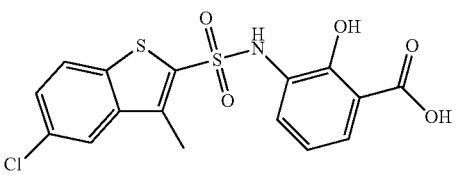 [SMILES: Cc1c(S(=O)(=O)Nc2cccc(C(=O)O)c2O)sc2ccc(Cl)cc12]

A solution of 5-chloro-3-methyl-benzothiophene-2-sulfonyl chloride (17 mg, 0.060 mmol) and 3-aminosalicylic acid (14 mg, 0.090 mmol) in 1200 μL of water/dioxane (1:6) was shaken at 35° C. for 5 days. The product was purified by reversed phase chromatography (ACE C8, 4 μm, 21×50 mm, flow 25 ml/min, gradient: 0.1% TFA in water/MeCN over 6 minutes). The title compound was obtained in 72% yield (17.2 mg). ¹H NMR (500 MHz, DMSO-d₆) δ ppm 2.48 (s, 3 H) 6.85 (t, J=7.92 Hz, 1 H) 7.46 (dd, J=7.69, 1.64 Hz, 1 H) 7.55 (dd, J=8.66, 2.05 Hz, 1 H) 7.63 (dd, J=7.92, 1.64 Hz, 1 H) 8.00 (dd, J=2.05, 0.47 Hz, 1 H) 8.04 (dd, J=8.66, 0.47 Hz, 1 H) 10.17 (br. s., 1 H). MS (ESI+) m/z 398 [M+H]⁺.

EXAMPLE 135

General Procedure 12

3-({[5-Chloro-4-(2,5-difluorophenyl)thiophen-2-yl]sulfonyl}amino)-2-hydroxybenzoic acid

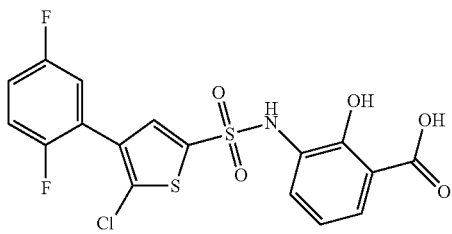 [SMILES: O=C(O)c1cccc(NS(=O)(=O)c2cc(-c3cc(F)ccc3F)c(Cl)s2)c1O]

A mixture of 3-{[(4-bromo-5-chlorothiophen-2-yl)sulfonyl]amino}-2-hydroxybenzoic acid (Intermediate 22) (20.6 mg, 0.050 mmol), 2,5-difluorophenylboronic acid (8.7 mg, 0.055 mmol), DIPEA (35 µL, 0.200 mmol) and Pd(dppf)Cl$_2$·CH$_2$Cl$_2$ (2 mg, 0.003 mmol) in aqueous dioxane (1 mL, 9:1 dioxane/water) was heated at 80° C. under nitrogen atmosphere over night. The reaction mixture was acidified by addition of TFA (50 µL). After being allowed to settle overnight the reaction mixture was filtered, diluted with MeOH and purified by reversed phase chromatography (ACE C8, 5 µm, 21×50 mm, flow 25 ml/min, gradient: 0.1% TFA in water/MeCN over 6 minutes) to give 9.7 mg of the title compound (44%). $^1$H NMR (500 MHz, MeOH-d$_4$) δ ppm 6.90 (t, J=7.94 Hz, 1 H) 7.14 (dddd, J=8.67, 5.60, 2.93, 0.46 Hz, 1 H) 7.16-7.21 (m, 1 H) 7.20-7.25 (tdd, J=8.96, 4.60, 0.46 Hz, 1 H) 7.34 (d, J=1.59 Hz, 1 H) 7.65 (dd, J=7.94, 1.65 Hz, 1 H) 7.74 (dd, J=7.94, 1.65 Hz, 1 H); MS (ESI+) m/z 446 [M+H]$^+$.

EXAMPLE 136

3-({[5-Chloro-4-(2,3-dihydro-1-benzofuran-5-yl)thiophen-2-yl]sulfonyl}amino)-2-hydroxybenzoic acid

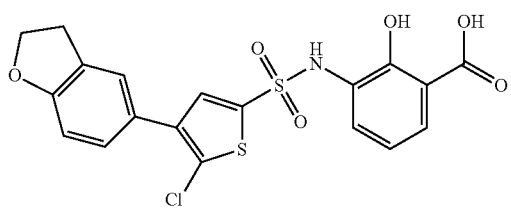 [SMILES: O=C(O)c1cccc(NS(=O)(=O)c2cc(-c3ccc4c(c3)CCO4)c(Cl)s2)c1O]

The product was prepared from 3-{[(4-bromo-5-chlorothiophen-2-yl)sulfonyl]amino}-2-hydroxybenzoic acid (Intermediate 22) (20.6 mg, 0.050 mmol) and 2,3-dihydrobenzofuran-5-boronic acid (9 mg, 0.055 mmol) according to the General Procedure 12, described in Example 135. The title compound was obtained in 46% yield (10.6 mg). $^1$H NMR (500 MHz, MeOH-d$_4$) δ ppm 3.23 (t, J=8.70 Hz, 2 H) 4.58 (t, J=8.70 Hz, 2 H) 6.76 (d, J=8.24 Hz, 1 H) 6.90 (t, J=7.95 Hz, 1 H) 7.14-7.17 (ddt, J=8.24, 1.97, 0.71 Hz, 1 H) 7.25 (dt, J=1.97, 1.30 Hz, 1 H) 7.31 (s, 1 H) 7.66 (dd, J=7.95, 1.65 Hz, 1 H) 7.74 (dd, J=7.95, 1.65 Hz, 1 H). MS (ESI+) m/z 452 [M+H]$^+$.

EXAMPLE 137

3-({[5-Chloro-4-(2-hydroxyphenyl)thiophen-2-yl]sulfonyl}amino)-2-hydroxybenzoic acid

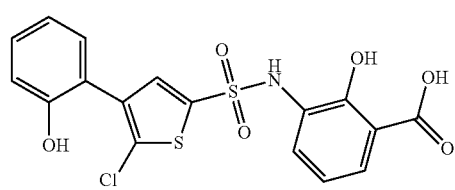 [SMILES: O=C(O)c1cccc(NS(=O)(=O)c2cc(-c3ccccc3O)c(Cl)s2)c1O]

The product was prepared from 3-{[(4-bromo-5-chlorothiophen-2-yl)sulfonyl]amino}-2-hydroxybenzoic acid (Intermediate 22) (20.6 mg, 0.050 mmol) and 2-(4,4,5,5-tetramethyl-1,3,2-dioxaborolan-2-yl)phenol (11 µl, 0.055 mmol) according to the General Procedure 12, described in Example 135. The title compound was obtained in 24% yield (5.3 mg). $^1$H NMR (500 MHz, MeOH-d$_4$) δ ppm 6.85 (ddd, J=7.60, 7.32, 1.15 Hz, 1 H) 6.87 (ddd, J=8.21, 1.15, 0.45 Hz, 1 H) 6.88 (t, J=7.95 Hz, 1 H) 7.15 (ddd, J=7.60, 1.71, 0.45 Hz, 1 H) 7.20 (ddd, J=8.21, 7.32, 1.71 Hz, 1 H) 7.39 (s, 1 H) 7.65 (dd, J=7.95, 1.65 Hz, 1 H) 7.71 (dd, J=7.95, 1.65 Hz, 1 H). MS (ESI+) m/z 426 [M+H]$^+$.

EXAMPLE 138

5-{[(5-Chloro-3-methyl-1-benzothiophen-2-yl)sulfonyl]amino}-2-hydroxybenzoic acid

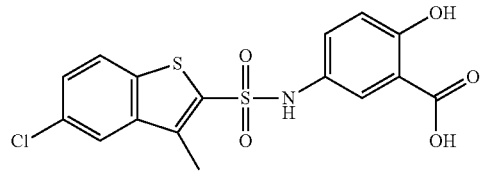 [SMILES: Cc1c(S(=O)(=O)Nc2ccc(O)c(C(=O)O)c2)sc2ccc(Cl)cc12]

A solution of 5-chloro-3-methyl-benzo[b]thiophene-2-sulfonyl chloride (22 mg, 0.075 mmol) and 5-aminosalicylic acid (17 mg, 0.112 mmol) in aqueous dioxane (800 µL, 4:1 dioxane/water) was shaken at 35° C. for 5 days. The product was purified by reversed phase chromatography (ACE C8, 4 µm, 21×50 mm, flow 25 ml/min, gradient: 0.1% TFA in water/MeCN over 6 minutes). The title compound was obtained in 79% yield (23.6 mg). $^1$H NMR (500 MHz, DMSO-d$_6$) δ ppm 2.41-2.43 (m, 3 H) 6.87 (d, J=8.79 Hz, 1 H) 7.20-7.25 (m, 1 H) 7.53 (dd, J=2.93, 1.46 Hz, 1 H) 7.56 (dd, J=8.79, 1.95 Hz, 1 H) 8.00 (d, J=1.95 Hz, 1 H) 8.06 (d, J=8.79 Hz, 1 H) 10.45 (s, 1 H). MS (ESI+) m/z 398 [M+H]$^+$.

EXAMPLE 139

5-{[(4'-Chlorobiphenyl-3-yl)sulfonyl]amino}-2-hydroxybenzoic acid

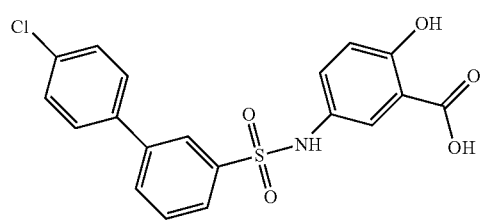 [SMILES: O=C(O)c1cc(NS(=O)(=O)c2cccc(-c3ccc(Cl)cc3)c2)ccc1O]

The product was prepared according to General Procedure 1, described in Example 1, with [[3-(4-chlorophenyl)phenyl]sulfonyl chloride (16 mg, 0.055 mmol) and 5-aminosalicylic acid (7.7 mg, 0.050 mmol) using a modified reaction temperature of 60° C. The title compound was obtained in 33% yield (6.7 mg). MS (ESI+) calcd mass for $C_{19}H_{14}ClNO_5S$ 403.028121, found 403.028561.

EXAMPLE 140

Methyl 5-{[(5-chloro-3-methyl-1-benzothiophen-2-yl)sulfonyl]amino}-2-hydroxybenzoate

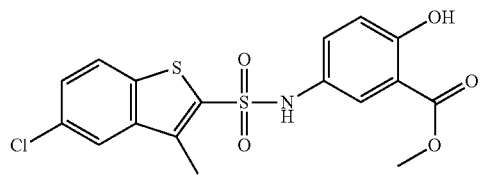 [SMILES: COC(=O)c1cc(NS(=O)(=O)c2sc3ccc(Cl)cc3c2C)ccc1O]

The title compound is prepared according to the procedure described for Example 33. MS (ESI+) calcd mass for $C_{17}H_{14}ClNO_5S_2$ 411.000192, found 411.000372.

EXAMPLE 141

5-Chloro-3-methyl-N-[3-(1,3-oxazol-5-yl)phenyl]-1-benzothiophene-2-sulfonamide

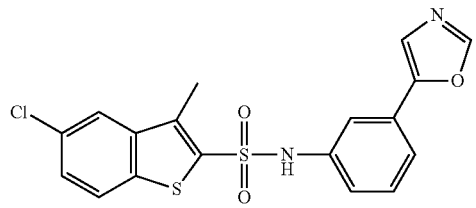 [SMILES: Cc1c(S(=O)(=O)Nc2cccc(-c3cnco3)c2)sc2ccc(Cl)cc12]

A solution containing 5-chloro-3-methyl-benzothiophene-2-sulfonyl chloride (20 mg, 0.071 mmol) and 3-(1,3-oxazol-5-yl)-aniline (17 mg, 0.11 mmol) in aqueous dioxane (1 mL, 95:5 dioxane/water) was stirred at room temperature for 4 weeks. The reaction mixture was diluted with MeOH/water and the crude product was purified by reversed phase chromatography (ACE C8, 5 µm, 21×50 mm, flow 25 ml/min, gradient: 0.1% TFA in water/MeCN over 6 minutes). The title compound was obtained in 63% yield (18 mg). $^1$H NMR (500 MHz, DMSO-$d_6$) δ ppm 2.54 (s, 3 H) 7.09-7.16 (m, 1 H) 7.35 (t, J=7.93 Hz, 1 H) 7.45 (d, J=8.06 Hz, 1 H) 7.52 (t, J=1.83 Hz, 1 H) 7.56 (dd, J=8.79, 2.20 Hz, 1 H) 7.61 (s, 1 H) 8.00 (d, J=1.71 Hz, 1 H) 8.06 (d, J=8.30 Hz, 1 H) 8.43 (s, 1 H) 10.96 (s, 1 H). MS (ESI+) m/z 405 [M+H]$^+$.

EXAMPLE 142

5-(Phenylsulfonyl)-N-[3-(1H-tetrazol-5-yl)phenyl]thiophene-2-sulfonamide

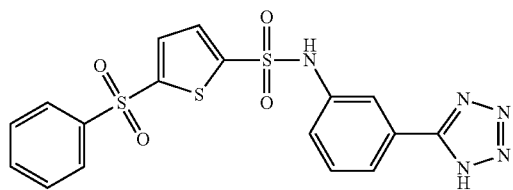 [SMILES: O=S(=O)(Nc1cccc(-c2nnn[nH]2)c1)c1ccc(S(=O)(=O)c2ccccc2)s1]

The product was prepared according to General Procedure 1, described in Example 1, with 5-benzenesulfonyl-thiophene-2-sulfonyl chloride (17.7 mg, 0.055 mmol) and 5-(3-aminophenyl)tetrazole (8.0 mg, 0.050 mmol). The title compound was obtained in 40% yield (8.9 mg). MS (ESI+) calcd mass for $C_{17}H_{13}N_5O_4S_3$ 447.012966, found 447.013676.

EXAMPLE 143

2,2-Dimethyl-N-[3-(1H-tetrazol-5-yl)phenyl]chromane-6-sulfonamide

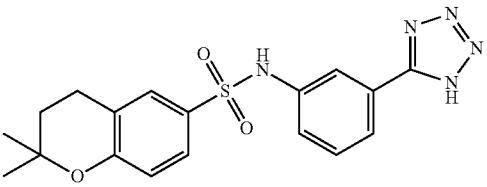 [SMILES: CC1(C)CCc2cc(S(=O)(=O)Nc3cccc(-c4nnn[nH]4)c3)ccc2O1]

The product was prepared according to General Procedure 1, described in Example 1, with dimethylchromanesulfonylchloride (14.3 mg, 0.055 mmol) and 5-(3-amino-phenyl)tetrazole (8.0 mg, 0.050 mmol). The title compound was obtained in 52% yield (10.1 mg). MS (ESI+) calcd mass for $C_{18}H_{19}N_5O_3S$ 385.120860, found 385.121960.

BIOLOGICAL TESTS 6-phosphofructo-2-kinase/fructose-2,6-bisphosphatase (PFK-2/BPase-2) is a bi-functional enzyme that catalyses the formation and degradation of fructose-2,6-bisphosphate (F-2,6-$P_2$) (see e.g. Pilkis et al., (1995) Annu. Rev. Biochem. 64, 799-835; and Okar et al., (2001) Trends Biochem. Sci. 26, 30-5; for reviews). The relative kinase (formation) and phosphatase (degradation) activities of the bi-functional enzyme control the intracellular levels of this regulator (F-2,6-$P_2$), which acts as an allosteric activator of glycolysis. Both the relative activities as well as the kinase to phosphatase ratios differ between the isoforms of the bi-functional enzymes, referred to as PFKFB1, PFKFB2, PFKFB3 and PFKFB4. Intracellular F-2,6-$P_2$ levels are consequently controlled by variable tissue expression of these isoforms, including splice variants or post-translational modifications (see e.g. Rider et al. (2007) Biochem J. 381, 561-579).

Methods for Measurement of Enzymatic Activity of PFKFB3 and PFKFB4

The PFKFB3 (placenta form) and PFKFB4 were produced and purified to homogeneity from *E. coli* at Biovitrum and at Sprint Bioscience. All other reagents were purchased from commercial sources. Two independent methods have been used for determination of the kinase activity of PFKFB3 (Method A and Method B). Method B has been used for determination of the kinase activity of PFKFB4.

Method A: The kinase activity of the bi-functional enzyme is readily quantified based on the production of F-2,6-$P_2$ as described by Van Schaftingen et al. (1982) Eur. J. Biochem. 129, 191-5. This sensitive assay is based on the potent activation of pyrophosphate dependent phosphofructokinase-1 ($PP_i$-PFK) from potato tubers by F-2,6-$P_2$. The use of a series of coupled enzymes leads to a consumption of NADH (nicotinamide adenine dinucleotide) that can be followed spectrophotometrically (an updated protocol is available in Van Schaftingen, (1984) Methods of Enzymatic Analysis (Bergmeyer, H. U., ed.), 3rd edn., vol. 6, pp. 335-341, Verlag Chemie, Weinheim). A protocol for measurements in 96-well microtiter plate format is also available (Bruni et al., (1989) Anal. Biochem. 178, 324-6). These assay protocols have been adopted for the measurement of the kinase activity of PFKFB3 with some modifications as described in the protocol below.

The assay was run in 96-well microtiter plates (Costar 3365 round bottom polypropylene) by consecutive additions of 30 µl each of a test compound solution (diluted from a DMSO stock solution), a PFKFB3 solution and a substrate (fructose-6-phosphate (F6P) and adenosine-5'-triphosphate (ATP)) containing solution. Controls in the absence of inhibitor (uninhibited activity) and 50 µM of an in-house inhibitor (completely inhibited kinase activity) were included in column 12 of the plate. The final concentrations of all reagents in a total assay volume of 90 µl per well were:

50 mM Tris-acetate at pH 8.0
0.1 mM EDTA (ethylene diamine tetraacetic acid)
10 mM $MgCl_2$
5 mM $Na_2HPO_4$ (buffered by the Tris-acetate to a final pH of 8.0)
5 nM PFKFB3
4 µM ATP
100 µM F6P (acid treated and then neutralized to remove any contaminating F-2,6-$P_2$; see Van Schaftingen, 1984)
1 mM dithiothreitol (DTT)
0.005% Tween-20

A test compound at various concentrations (which also added 0.83% DMSO to the final solution)

The enzymatic reaction was allowed to proceed for 10 minutes at room temperature while on a plate shaker at medium speed (750 RPM). The reaction was then terminated by the addition of 90 µl of a 0.4 M NaOH solution to all wells. The plate was then placed on the plateshaker at the same speed for two minutes to allow sufficient mixing. All samples were then diluted by a factor of 10 by transferring 20 µl from each well to the corresponding well of a new plate with 180 µl distilled water predispensed to all wells.

The next step in the protocol was quantification of the levels of F-2,6-$P_2$ in each well of the microtiter plate. This was done by transferring 20 µl of the content in each well to the corresponding position in a new plate (Nunc 269620 transparent 96-well plate). The control samples representing uninhibited and completely inhibited (two each) reactions were placed in column 12 of the plate. To ensure that all measured values were within the linear range of the response (measured to be between 0-1 nM of F-2,6-$P_2$ as also described by Van Schaftingen) the same volume of a 2.5 nM and a 5.0 nM standard sample were also added to column 12 (as all samples were diluted five-fold in the assay procedure this corresponds to 0.5 and 1.0 nM samples). The procedure then involved consecutive additions of three solutions with the following premixed components:

Assay-mix (20 µl): Tris-acetate at pH 8.0, NADH and $Mg(OAc)_2$
PPi/F6P-mix (40 µl): Pyrophosphate and F6P
Enzyme-mix (20 µl): Tris-acetate at pH 8.0, aldolase, triose phosphate isomerase, glycerol-3-phosphate dehydrogenase, pyrophosphate-dependent phosphofructokinase from potato tubers and bovine serum albumin (BSA)

The final concentrations of all reagents in a total assay volume of 100 µl per well were:
50 mM Tris-acetate at pH 8.0
0.15 mM NADH
2 mM $Mg(OAc)_2$
1 mM F6P (acid treated and then neutralized to remove any contaminating F-2,6-$P_2$; see Van Schaftingen, 1984 in Methods of Enzymatic Analysis (Bergmeyer, H. U., ed.), 3rd edn., vol. 6, pp. 335-341, Verlag Chemie, Weinheim)
0.5 mM pyrophosphate
0.5 U/ml aldolase
5 U/ml triose phosphate isomerase
1.7 U/ml glycerol-3-phosphate dehydrogenase
0.01 U/ml pyrophosphate-dependent phosphofructokinase from potato tubers
0.2 mg/ml BSA Test samples containing variable F-2,6-$P_2$ concentrations were diluted in NaOH (including also additional diluted components from the PFKFB3 reaction)

The coupled enzymatic reaction was allowed to proceed for 30 minutes at room temperature while on a plate shaker at medium speed (750 RPM). The reaction was then terminated by the addition of 20 µl of a 0.5M EDTA solution to all wells. The plate was then read in a Victor2 plate reader from Perkin-Elmer Life Sciences using the standard absorbance filter at 355 nm. The measured absorbance is proportional to the concentration of NADH, which in turn is proportional to the levels of F-2,6-$P_2$ within the linear range. This was defined by the 0.5 and 1.0 nM controls together with the completely inhibited control (corresponding to 0 nM F-2,6-$P_2$) on each plate. As described above controls were included on each plate to define the values for uninhibited and fully inhibited reactions and these values were used to calculate the % inhibition of the enzymatic reaction at any given compound concentration. The inhibitory potency or $IC_{50}$ values of test compounds on the kinase activity of PFKFB3 were calculated using a four-parameter model (model 205) in XLfit (IDBS ActivityBase).

Method B: The kinase activity of the bi-functional enzyme is readily quantified based on the production of ADP and F-2,6-$P_2$ from ATP and F6P. The ADP is detected with a kit, ADP-Glo™ Kinase Assay$^{(a-e)}$, from Promega. The assay is a luminescent ADP detection assay that measures kinase activity by quantifying the amount of ADP produced during the kinase reaction. The assay is performed in two steps; first, after the kinase reaction, an equal volume of ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminescence counter (1450 MicroBeta TriLux).

The assay was performed in white 384-well microtiter plates (OptiPlate, 6007299, PerkinElmer) by consecutive additions of 0.1 µL of a test compound solution (serial diluted in DMSO from compound DMSO stock solution and dispensed by acoustic dispensing from UV-star 384-well plate 7360153, VWR), 5 µL of enzyme solution and 5 µL of a substrate (fructose-6-phosphate (F6P) and adenosine-5'-triphosphate (ATP)) containing solution. Controls in the absence of inhibitor (uninhibited activity, only DMSO), 100 nM of an in-house inhibitor (QC, 50% inhibited kinase activity) and 49.5 µM of an in-house inhibitor (completely inhibited kinase activity) were included in column 23, 24 of the plate. Four reference dose response curves, one of them being the QC compound, were included in row O1-2, P1-2, and serial diluted as the test compounds. The final concentrations of all reagents in a total assay volume of 10.1 µL per well were:
50 mM Tris-HCl at pH 8.0
10 mM $MgCl_2$
5 mM $Na_2HPO_4$ at pH 8.0
81.48 nM PFKFB3 or 145 nM PFKFB4
8 µM ATP 100 μM F6P (acid treated and then neutralized to remove any contaminating F-2,6-$P_2$; see Van Schaftingen, 1984)
0.005% Tween-20
1 mM dithiothreitol (DTT)
A test compound at various concentrations or controls (final DMSO concentration 0.99%)

Enzyme, compounds and controls were pre-incubated at room temperature for 15 min before the addition of substrate solution. The enzymatic reaction was allowed to proceed for 20 min (PFKFB3) or 40 min (PFKFB4) at room temperature. The reaction was terminated by the addition of 10 μL of ADP-Glo™ Reagent to all wells and the plate was incubated for 40 min at room temperature. After addition of 20 μL Kinase Detection Reagent to all wells the plate was incubated for 30 min at room temperature, followed by measurement in 1450 MicroBeta TriLux. All plates were centrifuged after each addition (room temperature, short spin, 500 RPM, Megafuge 1.0 Heraeus Instruments).

As described above controls were included on each plate to define the values for uninhibited and fully inhibited reactions and these values were used to calculate the % inhibition of the enzymatic reaction at any given compound concentration. The inhibitory potency or $IC_{50}$ values of test compounds on the kinase activity of PFKFB3 or PFKFB4 were calculated using a four-parameter model (model 205) in XLfit (IDBS ActivityBase XE Runner).

Examples included herein have $IC_{50}$ values in the range of 10 nM to 15 μM as measured using the above described assays Method A and/or Method B (see Table I and Table II for exemplary data).

TABLE I

PFKFB3: $IC_{50}$ values for representative compounds as measured by Method A and/or B.

| Example Number | IC50 (μM) | Assay |
|---|---|---|
| 1 | 0.28 | A |
| 2 | 3.91 | A |
| 5 | 0.03 | A |
| 8 | 0.61 | A |
| 9 | 0.73 | A |
| 10 | 0.81 | A |
| 11 | 0.85 | A |
| 12 | 1.02 | A |
| 13 | 0.08 | A |
| 14 | 0.28 | A |
| 15 | 0.23 | A |
| 17 | 0.45 | A |
| 19 | 0.72 | A |
| 20 | 0.85 | A |
| 23 | 0.62 | B |
| 25 | 0.31 | A |
| 31 | 1.39 | A |
| 33 | 0.13 | B |
| 38 | 0.18 | A |
| 39 | 0.28 | B |
| 48 | 0.36 | A |
| 49 | 5.07 | A |
| 52 | 2.54 | A |
| 53 | 1.78 | A |
| 55 | 5.75 | A |
| 56 | 1.12 | A |
| 58 | 0.54 | A |
| 59 | 0.56 | A |
| 60 | 1.30 | B |
| 61 | 2.24 | B |
| 71 | 2.39 | B |
| 73 | 0.57 | B |
| 78 | 6.69 | A |
| 79 | 6.31 | A |
| 80 | 3.10 | B |

TABLE I-continued

PFKFB3: $IC_{50}$ values for representative compounds as measured by Method A and/or B.

| Example Number | IC50 (μM) | Assay |
|---|---|---|
| 81 | 9.84 | A |
| 83 | 8.45 | A |
| 86 | 2.80 | B |
| 99 | 1.42 | B |
| 137 | 5.18 | B |
| 138 | 9.03 | B |

TABLE II

PFKFB4: $IC_{50}$ values for representative compounds as measured by Method B

| Example Number | IC50 (μM) |
|---|---|
| 5 | 0.06 |
| 7 | 0.10 |
| 16 | 0.39 |
| 18 | 0.51 |
| 21 | 0.42 |
| 24 | 0.66 |
| 26 | 0.75 |
| 27 | 0.48 |
| 38 | 0.13 |
| 40 | 0.14 |
| 42 | 0.42 |
| 43 | 0.17 |
| 44 | 0.20 |
| 57 | 1.83 |
| 85 | 3.72 |
| 101 | 0.60 |
| 102 | 0.66 |
| 134 | 0.18 |

Method for Quantification of F-2,6-$P_2$ in Three Different Cancer Cell Lines

The relative kinase (formation) and phosphatase (degradation) activities of the bi-functional enzymes PFKFB3 and PFKFB4 control the intracellular levels of the regulator F-2,6-$P_2$, which acts as an allosteric activator of glycolysis. The levels of F-2,6-$P_2$ have been determined in three different cancer cell lines (MCF-7, PANC-1 and NUGC-3) using the van Shaftingen assay. The assay protocols described under "Methods for measurement of enzymatic activity of PFKFB3 and PFKFB4, Method A" have been adapted for the measurement of the inhibitory effect of compounds on the kinase activity of the various isoforms of the bifunctional enzyme (endogenously expressed) in the different cell lines. The modifications are described in the protocol below. All reagents were purchased from commercial sources or prepared inhouse.

Cell Line A (MCF-7, Human Breast Adenocarcinoma Cell Line)
Cells: MCF-7(ATCC-HBT22). Lot. no: 58469417.
Growth Medium:
Eagle's Minimum Essential Medium (EMEM), Sigma-Aldrich #M5650, 500 ml
10% FBS, Invitrogen, 10106-169
5 mL 200 mM L-glutamine, Invitrogen 25030024
5 mL 100 mM Sodium Pyruvate, Invitrogen 11360039
0.5 mL 10 mg/ml Bovine Insulin, Sigma-Aldrich 10516
Cells were seeded at a concentration of 450 000 cells/mL in 100 μL growth medium (45 000 cells/well)
Cell Line B (PANC-1, Human Pancreatic Carcinoma Cell Line)

Cells: PANC-1 (ATCC-CRL-1469). Lot. no: 58564651.
Growth medium: Dulbecco's Modified Eagle's Medium, DMEM, ATCC-30-2002 10% FBS, Invitrogen, 10106-169
  Cells were seeded at a concentration of 250 000 cells/mL in 100 µL growth medium (25 000 cells/well)
Cell Line C (NUGC-3, Human Gastric Cancer Cell Line)
Cells: NUGC-3(JCRB0822). Lot no: 04272009.
Growth medium: RPMI1640, Sigma-Aldrich, R8758 10% FBS, Invitrogen, 10106-169
  Cells were seeded at a concentration of 350 000 cells/mL in 100 µL growth medium (35 000 cells/well)
  Starvation medium: DMEM/F12 without phenol red and glucose free, SVA, 991373 0.25% FBS, Invitrogen, 10106-169
  Induction medium: DMEM/F12 without phenol red and glucose free, SVA, 991373 0.25% FBS, Invitrogen, 10106-169 (same as starvation medium)
  Cells were seeded in 96-well Corning Costar tissue culture plates (CLS3595, Sigma-Aldrich) using the concentrations specified above for the three different cell lines A-C and incubated over night at 37° C. and 5% $CO_2$. Row A was left empty. Next day the growth medium was discarded and replaced with 100 µL starvation medium. The plates were incubated for 18 h at 37° C. and 5% $CO_2$. After 18 h of starvation the cells were induced with 100 µL compound or control solutions. Compounds were either tested in two concentrations (50 µM and 10 µM) or in dose response curves starting from 50 µM and the final DMSO concentration in assay plates was 0.5%. Also a dose response curve of a reference inhibitor was included in row H on each plate. All compounds were tested in duplicate plates. Compounds (in 96 well CLS 3365, Sigma-Aldrich) were serial diluted in DMSO from 10 mM compound DMSO stock solutions with Janus (automated liquid handling workstation from PerkinElmer). 5 µL were transferred to a Greiner deep well plate (736-0155, VWR) with 495 µL starvation medium. The final start concentration of compounds in the dilution plate was 100 µM, 1% DMSO. For compounds tested as single points, 10 mM compound solutions were diluted five fold in DMSO to 2 mM, followed by the transfer of 5 µL to separate dilution plates with 495 µL starvation medium. The final concentration of compounds in these dilution plates were 100 or 20 µM, respectively, and final concentration of DMSO was 1%. The plates were incubated at 37° C. and 5% $CO_2$ for 1 h, followed by the addition of 10 µL 20 mM D-glucose in starvation medium. Controls, with and without 1 mM glucose, were included in row B. The final assay volume was 210 µL per well. After 2 h of incubation at 37° C. and 5% $CO_2$, supernatants were discarded and the cells were lysed by the addition of 25 µL 250 mM NaOH. The plates were incubated at 37° C. and 5% $CO_2$ for 5 min followed by an addition of 75 µL MilliQ $dH_2O$. The supernatants were further diluted with 210 µL MilliQ $dH_2O$ to a final concentration of 20 mM NaOH. 200 µL were transferred to NUNC 96-well plates (7322661, VWR) and the plates were sealed and stored at −20° C. until analysis.
  The amount of F-2,6-$P_2$ was quantified based on the coupled enzymatic reaction described by Van Schaftingen. If necessary the samples were further diluted in 20 mM NaOH before quantification. Plates stored at −20° C. were thawed and the F-2,6-$P_2$ quantification was initiated by transferring 40 µL from each well of the NUNC plate to the corresponding position in a trans-parent 96-well SpectraPlate-MB (6005649, PerkinElmer). In order to ensure that all F-2,6-$P_2$ measured values were within the linear range of response (between 0-1 nM final concentration of F-2,6-$P_2$ as described by Van Schaftingen), the same sample volume (40 µL) of an in-house produced F-2,6-$P_2$ standard was included on each plate in row A.
  The procedure described below involved consecutive additions of three solutions with the following premixed components:
  Assay-mix (40 µL): Tris-acetate at pH 8.0, NADH and Mg(OAc)$_2$
  Substrate-mix (80 µL): Pyrophosphate and F6P
  Enzyme-mix (40 µL): Tris-acetate at pH 8.0, aldolase, triose phosphate isomerase, glycerol-3-phosphate dehydrogenase, pyrophosphate-dependent phosphofructokinase from potato tubers and bovine serum albumin (BSA)
  The final concentrations of all reagents in a total assay volume of 200 µL per well were:
  50 mM Tris-acetate at pH 8.0
  0.15 mM NADH
  2 mM Mg(OAc)$_2$
  1 mM F6P (acid treated and then neutralized to remove any contaminating F-2,6-$P_2$; see Van Schaftingen, 1984 in Methods of Enzymatic Analysis (Bergmeyer, H. U., ed.), 3rd edn., vol. 6, pp. 335-341, Verlag Chemie, Weinheim)
  0.5 mM pyrophosphate
  0.45 U/mL aldolase
  5 U/mL triose phosphate isomerase
  1.7 U/mL glycerol-3-phosphate dehydrogenase
  0.01 U/mL pyrophosphate-dependent phosphofructokinase from potato tubers
  0.2 mg/mL BSA
  Test samples containing variable concentrations of F-2,6-$P_2$ diluted in NaOH
  The coupled enzymatic reaction was allowed to proceed for 45 minutes at room temperature and the absorbance at 340 nm was continuously measured every 30 seconds (SpectraMax plate reader, Molecular Devices). The measured absorbance is proportional to the concentration of NADH, which in turn is proportional to the levels of F-2,6-$P_2$ within the linear range. This was defined by the 0 to 1.0 nM F-2,6-$P_2$ controls in row A of the SpectraPlate. The $IC_{50}$ values for test compounds were calculated using a four-parameter model (model 205) in XLfit (Excel).
  Examples included herein have $IC_{50}$ values in the range 100 nM to 15 µM (see Table III for exemplary data) or >50% inhibition at 12.5 µM as measured using the above described assay. Examples 106, 107, 109, 111, 113, 115, 117, 123, 126 and 127 are representative examples showing >50% inhibition at 12.5 µM in PANC-1 cells.

TABLE III $IC_{50}$ values for representative compounds in different cell lines based on quantification of F-2,6-$P_2$

| Example Number | IC50 (µM) | Cell line |
| --- | --- | --- |
| 4 | 7.5 | PANC-1 |
| 5 | 2.3 | PANC-1 |
| 24 | 11.0 | PANC-1 |
| 27 | 13.8 | PANC-1 |
| 38 | 10.1 | PANC-1 |
| 74 | 4.0 | NUGC-3 |
| 74 | 3.7 | PANC-1 |
| 88 | 5.4 | PANC-1 |
| 92 | 0.5 | PANC-1 |
| 108 | 3.1 | PANC-1 |
| 112 | 4.3 | PANC-1 |

TABLE III-continued

IC$_{50}$ values for representative compounds in different cell lines based on quantification of F-2,6-P$_2$

| Example Number | IC50 (µM) | Cell line |
|---|---|---|
| 116 | 1.3 | PANC-1 |
| 118 | 2.8 | PANC-1 |
| 119 | 7.0 | PANC-1 |
| 120 | 3.5 | PANC-1 |
| 121 | 9.0 | PANC-1 |
| 122 | 8.7 | PANC-1 |
| 140 | 1.2* | MCF-7 |
| 141 | 3.0 | MCF-7 |

*The cells were seeded in the starvation medium containing 25 mM glucose. The cells were seeded at a concentration of 25 000 cells/well.

Method for Measurement of Inhibition of Cancer Cell Proliferation

To assess the antiproliferative response elicited by the compounds of the present invention in different tumour cell lines, total cellular protein in samples was quantified using the Sulphorhodamine B kit, TOX6, (Sigma-Aldrich).

Cells from selected tumour cell lines were cultured at 37° C., 5% $CO_2$, normoxia, in DMEM/F12 medium +10% FBS. Cells were plated at a density of 6-12 000 cells/well, depending on cell-line specific size and growth characteristics, and allowed to attach overnight.

Culture media supernatants were then removed and replaced with either fresh medium or with compounds of the present invention diluted in cell culture medium to indicated concentrations, and to a maximal DMSO concentration of 0.1%. All treatments were in quadruplicate. After indicated incubation times, samples were washed with PBS and the total cellular protein in each sample was quantitated after precipitation with TCA according to the manufacturer's instructions. Sulphorhodamine dye was added to the wells containing precipitated and air-dried cellular protein (80 µL/well). After 20 min incubation at room temperature and on a rotary shaker, the dye was discarded and the samples were gently rinsed with 1% HOAc until clear. After air drying, bound dye was solubilized in 200 µL 10 mM Tris base, and the absorbance of dye was measured at a wavelength of 565 nm. To quantify growth, samples were collected also at t=0 h, and the resulting absorbance was set to 100%.

An example demonstrating a growth-inhibitory effect on the gastric tumor cell line NUGC3 is illustrated in FIG. 1. In brief, the Example 74 was added at the indicated concentrations at 0 h and again at 48 h. After a total of 120 h, the measured effect on cancer cell proliferation was quantified as described above.

The invention claimed is:

1. A compound of formula (I)

(I)

wherein:
(i) A is O or S; and
$R^1$ is selected from H, halogen, and C1-C6 alkyl optionally substituted with at least one halogen;
$R^2$ and $R^3$ are independently selected from H, halogen, C1-C6 alkyl optionally substituted with at least one halogen, phenyl optionally substituted with at least one $R^6$, 5- or 6-membered heteroaryl optionally substituted with at least one $R^6$, and 5- or 6-membered arylsulfonyl or heteroarylsulfonyl, optionally substituted with at least one $R^6$;

provided that at least one of $R^2$ and $R^3$ is selected from said phenyl, heteroaryl, arylsulfonyl and heteroarylsulfonyl, and when L is (a), neither $R^2$ nor $R^3$ is unsubstituted phenyl;
or $R^2$ and $R^3$ form, together with the carbon atoms to which they are attached, a benzene ring optionally substituted with at least one $R^6$, or a 5- or 6-membered heteroaromatic or heterocyclic ring, optionally substituted with at least one $R^6$; or $R^1$ and $R^2$ form, together with the carbon atoms to which they are attached, a benzene ring optionally substituted with at least one $R^6$, or a 5- or 6-membered heteroaromatic or heterocyclic ring, optionally substituted with at least one $R^6$; and $R^3$ is selected from H, halogen, C1-C6 alkyl optionally substituted with at least one halogen;

or (ii) A is CR'=CR', and each R' is independently selected from H, halogen, and C1-C6 alkyl optionally substituted with at least one halogen;

$R^1$ is selected from H, halogen, and C1-C6 alkyl optionally substituted with at least one halogen;

$R^2$ is selected from H, halogen, C1-C6 alkyl optionally substituted with at least one halogen, and phenyl optionally substituted with at least one $R^6$;

$R^3$ is selected from H, halogen, and C1-C6 alkyl optionally substituted with at least one halogen, provided that:

when $R^2$ is selected from H, halogen and C1-C6 alkyl optionally substituted with at least one halogen, the ring containing A is substituted in ortho position relative to the sulphonamide bond with at least one substituent selected from halogen and C1-C6 alkyl substituted with at least one halogen;

when L is (a), $R^2$ is not unsubstituted phenyl; and when L is (c), $R^2$ is unsubstituted phenyl only when $R^4$ is not hydroxy;

L is (a)

wherein $R^4$ is COOR$^{12}$, and $R^5$ is selected from H and C1-C6 alkyl;
or

R⁴ is selected from H and C1-C6 alkyl, and R⁵ is COOR¹²; or

L is

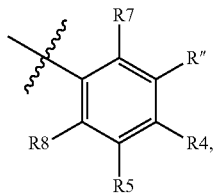

(c)

wherein
- R⁴ is selected from H, hydroxy and C1-C6 alkyl;
- R⁵ is selected from H, C1-C6 alkyl, and R" is selected from C0-C1 alkyl-COOR¹², or
- R⁵ is selected from COOR¹² and tetrazol-5-yl, said tetrazol-5-yl optionally being substituted by R⁹, and R" is selected from H, C1-C6 alkyl, and nitro;
- R⁷ is selected from H, C1-C6 alkyl, and nitro; and
- R⁸ is selected from H, hydroxy, and C1-C6 alkyl;

provided that:
- L is (a) only when at least one of R² or R³ is substituted phenyl or optionally substituted heteroaryl, or when R² and R³ together with the carbon atoms to which they are attached form a benzene ring optionally substituted by at least one R⁶; and
- when L is (c), R⁵ is COOR¹² or R" is C0-C1 alkyl-COOR¹² only when at least one of R² or R³ is optionally substituted phenyl or optionally substituted heteroaryl, or when R² and R³ together with the carbon atoms to which they are attached form a benzene ring optionally substituted by at least one R⁶;
- R⁶ is selected from C1-C6 alkyl, cyano, halogen, hydroxy, C1-C6 alkoxy, C1-C6 alkylthio, tetrahydropyrrolyl, R¹⁰R¹¹N, carbamoyl, and C1-C6 alkylcarbonylamino, or is an ethyleneoxy biradical forming, together with the atoms to which it is attached, a five-membered oxygen containing cycle, wherein any alkyl is optionally substituted with at least one halogen;
- R⁹ is selected from C0-C1 alkyl-COOR¹²;
- R¹⁰ and R¹¹ are independently selected from H and C1-C6 alkyl or form, together with the nitrogen to which they are attached, a 5- or 6-membered cyclic amino optionally containing one other cyclic heteroatom;
- R¹² is selected from H, C1-C6 alkyl, heteroaryl-C0-C2 alkyl, (C1-C3 alkoxy)$_p$C1-C3 alkyl,
- aryl-C0-C2 alkyl, heterocyclyl-C0-C2 alkyl, and C1-C6 dialkylamino-C1-C6 alkyl, wherein any cyclic moiety is optionally substituted with C1-C6 alkyl; and
- p is 1 or 2;
or a pharmaceutically acceptable salt, hydrate, solvate, or N-oxide thereof;

provided that said compound of formula (I) is not:
ethyl 2-(benzofuran-2-sulfonamido)thiazole-4-carboxylate;
ethyl 2-(5-methylbenzo[b]thiophene-2-sulfonamido)thiazole-4-carboxylate;
ethyl 2-(benzo[b]thiophene-2-sulfonamido)thiazole-4-carboxylate;
2-(3-(benzo[b]thiophene-2-sulfonamido)phenyl)acetic acid;
methyl 2-(3-(benzo[b]thiophene-2-sulfonamido)phenyl) acetate;
ethyl 3-(5-(6-oxo-1,6-dihydropyridazin-3-yl)furan-2-sulfonamido)benzoate;
ethyl 3-(5-(5-(trifluoromethyl)isoxazol-3-yl)furan-2-sulfonamido)benzoate;
ethyl 3-(5-(4,5-dimethyl-1H-pyrazol-3-yl)thiophene-2-sulfonamido)benzoate;
ethyl 3-(5-(5-methyl-1H-pyrazol-3-yl)thiophene-2-sulfonamido)benzoate;
ethyl 3-(5-(5-(trifluoromethyl)isoxazol-3-yl)thiophene-2-sulfonamido)benzoate;
ethyl 3-(5-(3-(trifluoromethyl)isoxazol-5-yl)thiophene-2-sulfonamido)benzoate;
ethyl 3-(5-(3-methylisoxazol-5-yl)thiophene-2-sulfonamido)benzoate;
ethyl 3-(4-(4-(tert-butyl)thiazol-2-yl)thiophene-2-sulfonamido)benzoate;
methyl 3-(4-(4-(tert-butyl)thiazol-2-yl)thiophene-2-sulfonamido)benzoate;
N-(3-(2H-tetrazol-5-yl)phenyl)-2,4,5-trichlorobenzenesulfonamide; or
N-(3-(1H-tetrazol-5-yl)phenyl)-2,4,5-trichlorobenzenesulfonamide.

2. The compound of claim 1, wherein A is O or S; or a pharmaceutically acceptable salt, hydrate, solvate, or N-oxide thereof.

3. The compound of claim 2, wherein A is S; or a pharmaceutically acceptable salt, hydrate, solvate, or N-oxide thereof.

4. The compound of claim 2, wherein
- R¹ is selected from H, halogen, and C1-C6 alkyl optionally substituted with at least one halogen; and
- R² and R³ form, together with the carbon atoms to which they are attached, a benzene ring, optionally substituted with at least one R⁶, or a 5- or 6-membered heteroaromatic or heterocyclic ring, optionally substituted with at least one R⁶; or
- R¹ and R² form, together with the carbon atoms to which they are attached, a benzene ring optionally substituted with at least one R⁶, or a 5- or 6-membered heteroaromatic or heterocyclic ring, optionally substituted with at least one R⁶; and
- R³ is selected from H, halogen, C1-C6 alkyl optionally substituted with at least one halogen;
or a pharmaceutically acceptable salt, hydrate, solvate, or N-oxide thereof.

5. The compound of claim 2, wherein
- R¹ is selected from H, halogen, and C1-C6 alkyl optionally substituted with at least one halogen;
- R² and R³ are independently selected from H, halogen, C1-C6 alkyl optionally substituted with at least one halogen, phenyl optionally substituted with at least one R⁶, 5- or 6-membered heteroaryl optionally substituted with at least one R⁶, and 5- or 6-membered arylsulfonyl or heteroarylsulfonyl, optionally substituted with at least one R⁶;
provided that
at least one of R² and R³ is selected from said phenyl, heteroaryl, arylsulfonyl and heteroarylsulfonyl, and
when L is (a), neither R² nor R³ is unsubstituted phenyl;
or a pharmaceutically acceptable salt, hydrate, solvate, or N-oxide thereof.

6. The compound of claim 1, wherein A is CR'=CR', wherein R' is as previously defined; or a pharmaceutically acceptable salt, hydrate, solvate, or N-oxide thereof.

7. The compound of claim 1, wherein L is,

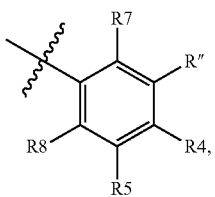

and wherein $R^4$, $R^5$, $R^7$, $R^8$ and R" are as previously defined;
or a pharmaceutically acceptable salt, hydrate, solvate, or N-oxide thereof.

8. The compound of claim 7, wherein
$R^4$ is selected from H and C1-C6 alkyl;
$R^5$ is tetrazol-5-yl, said tetrazol-5-yl optionally being substituted by $R^9$;
R" is selected from H and C1-C6 alkyl;
$R^7$ is selected from H and C1-C6 alkyl; and
$R^8$ is selected from H and C1-C6 alkyl;
or a pharmaceutically acceptable salt, hydrate, solvate, or N-oxide thereof.

9. The compound of claim 7, wherein
$R^4$ is selected from H, hydroxyl, and C1-C6 alkyl;
$R^5$ is selected from H and C1-C6 alkyl; and R" is selected from C0-C1 alkyl-COOR$^{12}$, or
$R^5$ is COOR$^{12}$ and R" is selected from H, C1-C6 alkyl, and nitro;
$R^7$ is selected from H, C1-C6 alkyl, and nitro; and
$R^8$ is selected from H, hydroxy, and C1-C6 alkyl;
or a pharmaceutically acceptable salt, hydrate, solvate, or N-oxide thereof.

10. The compound of claim 1, wherein L is

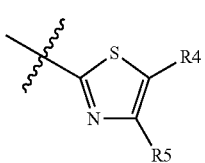

wherein $R^4$ and $R^5$ are as previously defined;
or a pharmaceutically acceptable salt, hydrate, solvate, or N-oxide thereof.

11. The compound according to claim 1, selected from the group consisting of:
2,3,4-trichloro-N-[3-(1H-tetrazol-5-yl)phenyl]benzenesulfonamide;
5-(1,3-oxazol-5-yl)-N-[3-(1H-tetrazol-5-yl)phenyl]thiophene-2-sulfonamide;
5-isopropyl-3-methyl-N-[3-(1H-tetrazol-5-yl)phenyl]benzothiophene-2-sulfonamide;
3-{[(5-isopropyl-3-methyl-1-benzothien-2-yl)sulfonyl]amino}benzoic acid;
2-{[(5-isopropyl-3-methyl-1-benzothien-2-yl)sulfonyl]amino}-1,3-thiazole-5-carboxylic acid;
2-{[(5-isopropyl-3-methyl-1-benzothien-2-yl)sulfonyl]amino}-4-methyl-1,3-thiazole-5-carboxylic acid;
3-{[(5-isopropyl-3-methyl-1-benzothien-2-yl)sulfonyl]amino}-5-nitrobenzoic acid;
[5-(3-{[(5-isopropyl-3-methyl-1-benzothien-2-yl)sulfonyl]amino}phenyl)-2H-tetrazol-2-yl]acetic acid;
5-isopropyl-3-methyl-N-[3-(1H-tetrazol-5-yl)phenyl]-1-benzofuran-2-sulfonamide;
3-{[(5-isopropyl-3-methyl-1-benzofuran-2-yl)sulfonyl]amino}benzoic acid;
(3-{[(5-isopropyl-3-methyl-1-benzothien-2-yl)sulfonyl]amino}phenyl)acetic acid;
N-[3-(1H-tetrazol-5-yl)phenyl]biphenyl-3-sulfonamide;
4'-fluoro-N-[3-(1H-tetrazol-5-yl)phenyl]biphenyl-3-sulfonamide;
2,6-dichloro-N-[3-(1H-tetrazol-5-yl)phenyl]-4-(trifluoromethyl)benzenesulfonamide;
4'-methoxy-N-[3-(1H-tetrazol-5-yl)phenyl]biphenyl-3-sulfonamide;
5-[2-(methylthio)pyrimidin-4-yl]-N-[3-(1H-tetrazol-5-yl)phenyl]thiophene-2-sulfonamide;
5-(5-fluoro-2-methoxyphenyl)-N-[3-(1H-tetrazol-5-yl)phenyl]thiophene-2-sulfonamide;
5-(3,5-difluorophenyl)-N-[3-(1H-tetrazol-5-yl)phenyl]thiophene-2-sulfonamide;
5-(2-methoxyphenyl)-N-[3-(1H-tetrazol-5-yl)phenyl]thiophene-2-sulfonamide;
5-(2-methyl-1,3-thiazol-4-yl)-N-[3-(1H-tetrazol-5-yl)phenyl]thiophene-2-sulfonamide;
5-(2-chlorophenyl)-N-[3-(1H-tetrazol-5-yl)phenyl]thiophene-2-sulfonamide;
5-(4-methylphenyl)-N-[3-(1H-tetrazol-5-yl)phenyl]thiophene-2-sulfonamide;
5-(2,4-dimethoxyphenyl)-N-[3-(1H-tetrazol-5-yl)phenyl]thiophene-2-sulfonamide;
5-(4-chlorophenyl)-N-[3-(1H-tetrazol-5-yl)phenyl]thiophene-2-sulfonamide;
5-(4-fluoro-2-methoxyphenyl)-N-[3-(1H-tetrazol-5-yl)phenyl]thiophene-2-sulfonamide;
5-chloro-3-methyl-N-[3-(1H-tetrazol-5-yl)phenyl]-1-benzothiophene-2-sulfonamide;
3,5-dimethyl-N-[3-(1H-tetrazol-5-yl)phenyl]-1-benzothiophene-2-sulfonamide;
5-bromo-3-methyl-N-[3-(1H-tetrazol-5-yl)phenyl]-1-benzothiophene-2-sulfonamide;
7-methoxy-3-methyl-N-[3-(1H-tetrazol-5-yl)phenyl]-1-benzothiophene-2-sulfonamide;
7-chloro-3-methyl-N-[3-(1H-tetrazol-5-yl)phenyl]-1-benzothiophene-2-sulfonamide;
5-methoxy-3-methyl-N-[3-(1H-tetrazol-5-yl)phenyl]-1-benzothiophene-2-sulfonamide;
3-{[(5-chloro-3-methyl-1-benzothien-2-yl)sulfonyl]amino}benzoic acid;
3-methyl-N-[3-(1H-tetrazol-5-yl)phenyl]-1-benzothiophene-2-sulfonamide;
5-methyl-N-[3-(1H-tetrazol-5-yl)phenyl]-1-benzothiophene-2-sulfonamide;
3-{[(5-bromo-3-methyl-1-benzothien-2-yl)sulfonyl]amino}benzoic acid;
3-{[(7-methoxy-3-methyl-1-benzothien-2-yl)sulfonyl]amino}benzoic acid;
5-fluoro-3-methyl-N-[3-(1H-tetrazol-5-yl)phenyl]-1-benzothiophene-2-sulfonamide;
3-{[(7-chloro-3-methyl-1-benzothien-2-yl)sulfonyl]amino}benzoic acid;
3-methyl-5-pyrrolidin-1-yl-N-[3-(1H-tetrazol-5-yl)phenyl]-1-benzothiophene-2-sulfonamide;
3-{[(3-methyl-5-pyrrolidin-1-yl-1-benzothien-2-yl)sulfonyl]amino}benzoic acid;
3-{[(5-amino-3-methyl-1-benzothien-2-yl)sulfonyl]amino}benzoic acid;

5-amino-3-methyl-N-[3-(1H-tetrazol-5-yl)phenyl]-1-benzothiophene-2-sulfonamide;
3-({[5-(acetylamino)-3-methyl-1-benzothien-2-yl]sulfonyl}amino)benzoic acid;
3-(p-tolyl)-N-[3-(1H-tetrazol-5-yl)phenyl]benzenesulfonamide;
2,4-dichloro-5-methyl-N-[3-(1H-tetrazol-5-yl)phenyl]benzenesulfonamide;
3-(3,5-Dichlorophenyl)-N-[3-(1H-tetrazol-5-yl)phenyl]benzenesulfonamide;
2,4-dichloro-6-methyl-N-[3-(1H-tetrazol-5-yl)phenyl]benzenesulfonamide;
3-[[3-(3,5-dichlorophenyl)phenyl]sulfonylamino]benzoic acid;
N-[3-(1H-tetrazol-5-yl)phenyl]-3-[4-(trifluoromethyl)phenyl]benzenesulfonamide;
4-bromo-N-[3-(1H-tetrazol-5-yl)phenyl]-2-(trifluoromethyl)benzenesulfonamide;
4-bromo-2-fluoro-N-[3-(1H-tetrazol-5-yl)phenyl]benzenesulfonamide;
3-[5-[[3-(1H-tetrazol-5-yl)phenyl]sulfamoyl]-2-thienyl]benzamide;
5-(5-chloro-1,2,4-thiadiazol-3-yl)-N-[3-(1H-tetrazol-5-yl)phenyl]thiophene-2-sulfonamide;
5-phenyl-N-[3-(1H-tetrazol-5-yl)phenyl]thiophene-2-sulfonamide;
3-[[5-(2-methylsulfanylpyrimidin-4-yl)-2-thienyl]sulfonylamino]benzoic acid;
3-[[5-(2-methyl-1,3-thiazol-4-yl)-2-thienyl]sulfonylamino]benzoic acid;
N-[3-(1H-tetrazol-5-yl)phenyl]-5-[5-(trifluoromethyl)isoxazol-3-yl]thiophene-2-sulfonamide;
N-[3-(1H-tetrazol-5-yl)phenyl]benzofuran-2-sulfonamide;
5-isoxazol-3-yl-N-[3-(1H-tetrazol-5-yl)phenyl]thiophene-2-sulfonamide;
2,4,6-trichloro-N-[3-(1H-tetrazol-5-yl)phenyl]benzenesulfonamide;
2,3-dichloro-N-[3-(1H-tetrazol-5-yl)phenyl]benzenesulfonamide;
2,5-dichloro-N-[3-(1H-tetrazol-5-yl)phenyl]benzenesulfonamide;
2,4-dichloro-N-[3-(1H-tetrazol-5-yl)phenyl]benzenesulfonamide;
2,4-difluoro-N-[3-(1H-tetrazol-5-yl)phenyl]benzenesulfonamide;
methyl 3-{[(5-chloro-3-methyl-1-benzothien-2-yl)sulfonyl]amino}benzoate
3-{[(3-methyl-1-benzothiophen-2-yl)sulfonyl]amino}benzoic acid;
3-{[(5-fluoro-3-methyl-1-benzothiophen-2-yl)sulfonyl]amino}benzoic acid;
3-{[(5-methoxy-3-methyl-1-benzothiophen-2-yl)sulfonyl]amino}benzoic acid;
3-{[(5-pyridin-2-yl-2-thienyl)sulfonyl]amino}benzoic acid;
3-{[(5-isoxazol-3-yl-2-thienyl)sulfonyl]amino}benzoic acid;
3-[(biphenyl-3-ylsulfonyl)amino]benzoic acid;
2-chloro-4-fluoro-N-[3-(1H-tetrazol-5-yl)phenyl]benzenesulfonamide;
N-[3-(1H-tetrazol-5-yl)phenyl]-1-benzothiophene-2-sulfonamide;
3-[(1-benzothien-2-ylsulfonyl)amino]benzoic acid;
5-isoxazol-5-yl-N-[3-(1H-tetrazol-5-yl)phenyl]thiophene-2-sulfonamide;
methyl 3-({[5-(2-methyl-1,3-thiazol-4-yl)-2-thienyl]sulfonyl}amino)benzoate
3-{[(5-methyl-1-benzothiophen-2-yl)sulfonyl]amino}benzoic acid;
4'-chloro-N-[3-(1H-tetrazol-5-yl)phenyl]biphenyl-3-sulfonamide;
3',4'-dichloro-N-[3-(1H-tetrazol-5-yl)phenyl]biphenyl-3-sulfonamide;
methyl 3-({[3-methyl-5-(1-methylethyl)-1-benzothiophen-2-yl]sulfonyl}amino)benzoate
3-{[(4'-chlorobiphenyl-3-yl)sulfonyl]amino}benzoic acid;
3-{[(4'-fluorobiphenyl-3-yl)sulfonyl]amino}benzoic acid;
3-{[(4'-methoxybiphenyl-3-yl)sulfonyl]amino}benzoic acid;
3-{[(3',4'-dichlorobiphenyl-3-yl)sulfonyl]amino}benzoic acid;
5-(3-methoxyphenyl)-N-[3-(1H-tetrazol-5-yl)phenyl]thiophene-2-sulfonamide;
5-(3,4-dichlorophenyl)-N-[3-(1H-tetrazol-5-yl)phenyl]thiophene-2-sulfonamide;
N-[3-(1H-tetrazol-5-yl)phenyl]-5-[3-(trifluoromethyl)phenyl]thiophene-2-sulfonamide;
5-(2-methylphenyl)-N-[3-(1H-tetrazol-5-yl)phenyl]thiophene-2-sulfonamide
5-(2,4-difluorophenyl)-N-[3-(1H-tetrazol-5-yl)phenyl]thiophene-2-sulfonamide;
5-(3-chloro-4-fluorophenyl)-N-[3-(1H-tetrazol-5-yl)phenyl]thiophene-2-sulfonamide;
5-(3-chlorophenyl)-N-[3-(1H-tetrazol-5-yl)phenyl]thiophene-2-sulfonamide;
5-pyridin-4-yl-N-[3-(1H-tetrazol-5-yl)phenyl]thiophene-2-sulfonamide;
3-{[(3-methyl-5-morpholin-4-yl-1-benzothiophen-2-yl)sulfonyl]amino}benzoic acid;
2-(1H-pyrrol-1-yl)ethyl 3-{[(5-chloro-3-methyl-1-benzothien-2-yl)sulfonyl]amino}benzoate;
ethyl 3-{[(5-chloro-3-methyl-1-benzothien-2-yl)sulfonyl]amino}benzoate;
isopropyl 3-{[(5-chloro-3-methyl-1-benzothien-2-yl)sulfonyl]amino}benzoate;
2-methoxyethyl 3-{[(5-chloro-3-methyl-1-benzothiophen-2-yl)sulfonyl]amino}benzoate;
butyl 3-{[(5-chloro-3-methyl-1-benzothiophen-2-yl)sulfonyl]amino}benzoate;
benzyl 3-{[(5-chloro-3-methyl-1-benzothiophen-2-yl)sulfonyl]amino}benzoate;
propyl 3-{[(5-chloro-3-methyl-1-benzothien-2-yl)sulfonyl]amino}benzoate;
pentyl 3-{[(5-chloro-3-methyl-1-benzothiophen-2-yl)sulfonyl]amino}benzoate;
hexyl 3-{[(5-chloro-3-methyl-1-benzothiophen-2-yl)sulfonyl]amino}benzoate;
phenyl 3-{[(5-chloro-3-methyl-1-benzothiophen-2-yl)sulfonyl]amino}benzoate;
tetrahydrofuran-3-yl 3-{[(5-chloro-3-methyl-1-benzothiophen-2-yl)sulfonyl]amino}benzoate;
tetrahydrofuran-3-ylmethyl 3-{[(5-chloro-3-methyl-1-benzothiophen-2-yl)sulfonyl]amino}-benzoate;
3-(dimethylamino)propyl 3-{[(5-chloro-3-methyl-1-benzothiophen-2-yl)sulfonyl]amino}-benzoate;
methyl {5-[3-({[3-methyl-5-(1-methylethyl)-1-benzothiophen-2-yl]sulfonyl}amino)phenyl]-2H-tetrazol-2-yl}acetate;
methyl 3-{[(5-bromo-3-methyl-1-benzothiophen-2-yl)sulfonyl]amino}benzoate;

methyl 3-{[(7-methoxy-3-methyl-1-benzothiophen-2-yl)sulfonyl]amino}benzoate;
methyl 3-{[(7-chloro-3-methyl-1-benzothiophen-2-yl)sulfonyl]amino}benzoate;
methyl 3-({[3-methyl-5-(1-methylethyl)-1-benzofuran-2-yl]sulfonyl}amino)benzoate;
methyl 2-({[3-methyl-5-(1-methylethyl)-1-benzothiophen-2-yl]sulfonyl}amino)-1,3-thiazole-5-carboxylate;
ethyl 4-methyl-2-({[3-methyl-5-(1-methylethyl)-1-benzothiophen-2-yl]sulfonyl}amino)-1,3-thiazole-5-carboxylate;
ethyl 2-{[(5-chloro-3-methyl-1-benzothiophen-2-yl)sulfonyl]amino}-4-methyl-1,3-thiazole-5-carboxylate;
ethyl 2-({[5-chloro-4-(2,5-difluorophenyl)thiophen-2-yl]sulfonyl}amino)-4-methyl-1,3-thiazole-5-carboxylate;
2-{[(5-chloro-3-methyl-1-benzothiophen-2-yl)sulfonyl]amino}-4-methyl-1,3-thiazole-5-carboxylic acid;
2-({[5-chloro-4-(2,5-difluorophenyl)thiophen-2-yl]sulfonyl}amino)-4-methyl-1,3-thiazole-5-carboxylic acid;
2-{[(5-chloro-3-methyl-1-benzothiophen-2-yl)sulfonyl]amino}-1,3-thiazole-5-carboxylic acid;
2-({[5-(3,5-difluorophenyl)thiophen-2-yl]sulfonyl}amino)-5-methyl-1,3-thiazole-4-carboxylic acid;
2-({[5-chloro-4-(2,5-difluorophenyl)thiophen-2-yl]sulfonyl}amino)-5-methyl-1,3-thiazole-4-carboxylic acid;
5-methyl-2-({[3-methyl-5-(1-methylethyl)-1-benzothiophen-2-yl]sulfonyl}amino)-1,3-thiazole-4-carboxylic acid;
3-{[(5-chloro-3-methyl-1-benzothiophen-2-yl)sulfonyl]amino}-2-hydroxybenzoic acid;
3-({[5-chloro-4-(2,5-difluorophenyl)thiophen-2-yl]sulfonyl}amino)-2-hydroxybenzoic acid;
3-({[5-chloro-4-(2,3-dihydro-1-benzofuran-5-yl)thiophen-2-yl]sulfonyl}amino)-2-hydroxybenzoic acid;
3-({[5-chloro-4-(2-hydroxyphenyl)thiophen-2-yl]sulfonyl}amino)-2-hydroxybenzoic acid;
5-{[(5-chloro-3-methyl-1-benzothiophen-2-yl)sulfonyl]amino}-2-hydroxybenzoic acid;
5-{[(4'-chlorobiphenyl-3-yl)sulfonyl]amino}-2-hydroxybenzoic acid;
methyl 5-{[(5-chloro-3-methyl-1-benzothiophen-2-yl)sulfonyl]amino}-2-hydroxybenzoate;
5-(phenylsulfonyl)-N-[3-(1H-tetrazol-5-yl)phenyl]thiophene-2-sulfonamide;
or a pharmaceutically acceptable salt, hydrate, solvate, or N-oxide thereof.

12. A pharmaceutical composition, comprising a compound of formula (I)

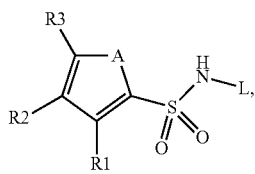

(I)

and a pharmaceutically acceptable carrier, wherein:
(i) A is O or S; and
R$^1$ is selected from H, halogen, and C1-C6 alkyl optionally substituted with at least one halogen; and
R$^2$ and R$^3$ are independently selected from H, halogen, C1-C6 alkyl optionally substituted with at least one halogen; phenyl optionally substituted with at least one R$^6$, 5- or 6-membered heteroaryl optionally substituted with at least one R$^6$, and 5- or 6-membered arylsulfonyl or heteroarylsulfonyl, optionally substituted with at least one R$^6$;
provided that
at least one of R$^2$ and R$^3$ is selected from said phenyl, heteroaryl, arylsulfonyl and heteroarylsulfonyl, and
when L is (a), neither R$^2$ nor R$^3$ is unsubstituted phenyl;
or
R$^2$ and R$^3$ form, together with the carbon atoms to which they are attached, a benzene ring optionally substituted with at least one R$^6$; or a 5- or 6-membered heteroaromatic or heterocyclic ring, optionally substituted with at least one R$^6$;
or
R$^1$ and R$^2$ form, together with the carbon atoms to which they are attached, a benzene ring optionally substituted with at least one R$^6$, or a 5- or 6-membered heteroaromatic or heterocyclic ring, optionally substituted with at least one R$^6$; and
R$^3$ is selected from H, halogen, C1-C6 alkyl optionally substituted with at least one halogen; or
(ii) A is CR'=CR';
each R' is independently selected from H, halogen, and C1-C6 alkyl optionally substituted with at least one halogen;
R$^1$ is selected from H, halogen, and C1-C6 alkyl optionally substituted with at least one halogen;
R$^2$ is selected from H, halogen, C1-C6 alkyl optionally substituted with at least one halogen; and phenyl optionally substituted with at least one R$^6$; and
R$^3$ is selected from H, halogen, and C1-C6 alkyl optionally substituted with at least one halogen;
provided that:
when R$^2$ is selected from H, halogen and C1-C6 alkyl optionally substituted with at least one halogen, the ring containing A is substituted in ortho position relative to the sulphonamide bond with at least one substituent selected from halogen and C1-C6 alkyl optionally substituted with at least one halogen;
when L is (a), R$^2$ is not unsubstituted phenyl; and
when L is (c), R$^2$ is unsubstituted phenyl only when R$^4$ is not hydroxy;
L is

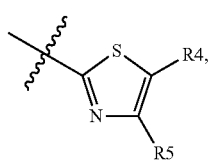

(a)

wherein
R$^4$ is COOR$^{12}$, and R$^5$ is selected from H and C1-C6 alkyl;
or $R^4$ is selected from H and C1-C6 alkyl, and $R^5$ is COOR$^{12}$;
or
L is

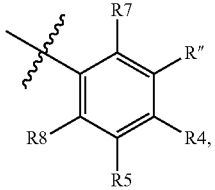
(c)

wherein
- $R^4$ is selected from H, hydroxy and C1-C6 alkyl, and
- $R^5$ is selected from H, C1-C6 alkyl, and R" is selected from C0-C1 alkyl-COOR$^{12}$, or
- $R^5$ is selected from COOR$^{12}$ and tetrazol-5-yl, said tetrazol-5-yl optionally being substituted by $R^9$, and R" is selected from H, C1-C6 alkyl, and nitro;
- $R^7$ is selected from H, C1-C6 alkyl, and nitro; and
- $R^8$ is selected from H, hydroxy, and C1-C6 alkyl;
- provided that:
  - L is (a) only when at least one of $R^2$ or $R^3$ is optionally substituted phenyl or optionally substituted heteroaryl, or when $R^2$ and $R^3$ together with the carbon atoms to which they are attached form a benzene ring optionally substituted by at least one $R^6$; and
  - when L is (c), $R^5$ is COOR$^{12}$ or R" is C0-C1 alkyl-COOR$^{12}$ only when at least one of $R^2$ or $R^3$ is optionally substituted phenyl or optionally substituted heteroaryl, or when $R^2$ and $R^3$ together with the carbon atoms to which they are attached form a benzene ring optionally substituted by at least one $R^6$;
- $R^6$ is selected from C1-C6 alkyl, cyano, halogen, hydroxy, C1-C6 alkoxy, C1-C6 alkylthio, tetrahydropyrrolyl, $R^{10}R^{11}N$, carbamoyl, and C1-C6 alkylcarbonylamino, or is an ethyleneoxy biradical forming, together with the atoms to which it is attached, a five-membered oxygen containing cycle; wherein any alkyl is optionally substituted with at least one halogen;
- $R^9$ is selected from C0-C1 alkyl-COOR$^{12}$;
- $R^{10}$ and $R^{11}$ are independently selected from H and C1-C6 alkyl or form, together with the nitrogen to which they are attached, a 5- or 6-membered cyclic amino optionally containing one other cyclic heteroatom;
- $R^{12}$ is selected from H, C1-C6 alkyl; heteroaryl-C0-C2 alkyl, (C1-C3 alkoxy)$_p$C1-C3 alkyl-, aryl-C0-C2 alkyl, heterocyclyl-C0-C2 alkyl, and C1-C6 dialkylamino-C1-C6 alkyl, wherein any cyclic moiety is optionally substituted with C1-C6 alkyl; and
- p is 1 or 2;
- or a pharmaceutically acceptable salt, hydrate, solvate, or N-oxide thereof;
- provided that the compound is not
  - ethyl 3-(5-(4,5-dimethyl-1H-pyrazol-3-yl)thiophene-2-sulfonamido)benzoate, or
  - ethyl 3-(5-(5-methyl-1H-pyrazol-3-yl)thiophene-2-sulfonamido)benzoate.

13. The compound of claim 1, wherein when L is (c):
- $R^4$ is selected from H, hydroxyl, and C1-C6 alkyl;
- $R^5$ is selected from H, C1-C6 alkyl, and R" is COOR$^{12}$, or
- $R^5$ is selected from COOR$^{12}$ and tetrazol-5-yl, said tetrazol-5-yl optionally being substituted by $R^9$, and R" is selected from H, C1-C6 alkyl, and nitro;
- $R^7$ is selected from H, C1-C6 alkyl, and nitro; and
- $R^8$ is selected from H, hydroxy, and C1-C6 alkyl.

14. The compound of claim 2, wherein when L is (c):
- $R^4$ is selected from H, hydroxy and C1-C6 alkyl;
- $R^5$ is selected from H, C1-C6 alkyl, and R" is COOR$^{12}$, or
- $R^5$ is selected from COOR$^{12}$ and tetrazol-5-yl, said tetrazol-5-yl optionally being substituted by $R^9$, and R" is selected from H, C1-C6 alkyl, and nitro;
- $R^7$ is selected from H, C1-C6 alkyl, and nitro; and
- $R^8$ is selected from H, hydroxy, and C1-C6 alkyl.

15. The compound of claim 1, wherein when A is CR'=CR', $R^2$ is phenyl optionally substituted with at least one $R^6$.

16. The compound of claim 13, wherein when A is CR'=CR', $R^2$ is phenyl optionally substituted with at least one $R^6$.

* * * * *